US008791094B2

(12) United States Patent
Morrison et al.

(10) Patent No.: US 8,791,094 B2
(45) Date of Patent: Jul. 29, 2014

(54) TREATMENT OF PROSTATE CANCER

(75) Inventors: Jodie Pope Morrison, Wakefield, MA (US); Cy Aaron Stein, New City, NY (US); David Scott Casebier, Carlisle, MA (US)

(73) Assignee: Tokai Pharmaceuticals, Inc., Cambridge, MA (US)

( * ) Notice: Subject to any disclaimer, the term of this patent is extended or adjusted under 35 U.S.C. 154(b) by 439 days.

(21) Appl. No.: 12/851,070

(22) Filed: Aug. 5, 2010

(65) Prior Publication Data

US 2011/0034428 A1 Feb. 10, 2011

Related U.S. Application Data

(60) Provisional application No. 61/232,257, filed on Aug. 7, 2009, provisional application No. 61/261,265, filed on Nov. 13, 2009.

(51) Int. Cl.
*A61K 31/58* (2006.01)
*C07J 43/00* (2006.01)

(52) U.S. Cl.
CPC .............. *C07J 43/003* (2013.01); *A61K 31/58* (2013.01)
USPC ........................................... 514/176; 540/95

(58) Field of Classification Search
CPC .............................. A61K 31/58; C07J 43/003
See application file for complete search history.

(56) References Cited

U.S. PATENT DOCUMENTS

| | | | |
|---|---|---|---|
| 4,000,125 | A | 12/1976 | Casagrande et al. |
| 5,601,981 | A | 2/1997 | Malins |
| 5,604,213 | A | 2/1997 | Barrie et al. |
| 5,994,335 | A | 11/1999 | Brodie et al. |
| 6,200,965 | B1 | 3/2001 | Brodie et al. |
| 6,444,683 | B2 | 9/2002 | Brodie et al. |
| 7,875,599 | B2 | 1/2011 | Brodie |
| 2001/0001099 | A1 | 5/2001 | Brodie et al. |
| 2003/0054053 | A1 | 3/2003 | Young et al. |
| 2008/0280864 | A1 | 11/2008 | Brodie et al. |
| 2010/0047338 | A1 | 2/2010 | Brodie et al. |
| 2010/0048524 | A1 | 2/2010 | Brodie et al. |
| 2010/0048912 | A1 | 2/2010 | Brodie et al. |
| 2010/0048913 | A1 | 2/2010 | Brodie et al. |
| 2010/0048914 | A1 | 2/2010 | Brodie et al. |
| 2010/0137269 | A1 | 6/2010 | Brodie et al. |

FOREIGN PATENT DOCUMENTS

| | | |
|---|---|---|
| WO | WO 2005/014023 A1 | 2/2005 |
| WO | WO 2006/093993 A1 | 9/2006 |
| WO | WO-2008-154382 A1 | 12/2008 |

OTHER PUBLICATIONS

Garrett et al. [Editors]. Chapter 8: Lipids. Biochemistry (Second Edition). Saunders College Publishing. 1999. pp. 238-258.*

Chaumeil. "Micronization: A Method of Improving the Bioavailability of Poorly Soluble Drugs", Meth Find Exp Clin Pharmacol, 1998; 20(3):211-215.*
PCT/US10/044570 Search Report and Written Opinion mailed Apr. 29, 2011.
Moreira, Vania et al. "Synthesis and evaluation of novel 17-indazole androstene derivatives desig ned as CYP17 inhibitors" Steroids 72(14): 939-948 (2007).
Vasaitis, Tadas et al. "Androgen Receptor Inactivation Contributes to Anti-tumor Efficacy of CYP17 Inhibitor VN/124-1 in Prostate Cancer" Mol Cancer Ther 7(8): 2348-2357 (2008).
European search report dated Nov. 6, 2012 for EP Application No. 10807167.1.
Office Action dated Apr. 4, 2012 for U.S. Appl. No. 12/577,090.
Office Action dated Oct. 17, 2012 for U.S. Appl. No. 12/577,090.
Abstract ANIH Grant Project Reference No. 5RO1 CA27440-24, approximate date Feb. 20, 2003; approximate award date Jun. 3, 2003.
Abstract of NIH Grant Project Reference No. 2R01 CA27440-25A1, approximate submission date Feb. 18, 2004; approximate award date Sep. 23, 2004.
Abstract of NIH Grant Project Reference No. 3RO1 CA27440-22S1, approximate date Jun. 21, 2001; approximate award date Aug. 17, 2001.
Abstract of NIH Grant Project Reference No. 3RO1 CA27440-23S1, approximate date May 3, 2002; approximate award date Jun. 21, 2002.
Abstract of NIH Grant Project Reference No. 5RO1 CA27440-23, approximate date Jan. 21, 2002; approximate award date Apr. 29, 2002.
Abstract of NIH Grant Project Reference No. 5RO1 CA27440-24S1, approximate date Apr. 1, 2003; approximate award date Jun. 3, 2003.
Abstract of NIH Grant Project Reference No. 5RO1 CA27440-26, approximate submission date Jul. 1, 2005; approximate award date Aug. 2, 2005.
Abstract of NIH Grant Project Reference No. 5RO1CA27440-27, approximate submission date Apr. 26, 2006.
Barrie, et al. Pharmacology of novel steroidal inhibitors of cytochrome P450(17) alpha (17 alpha-hydroxylase/C17-20 lyase). J Steroid Biochem Mol Biol. Sep. 1994;50(5-6):267-73.
Bruchovsky, et al. The conversion of testosterone to 5-alpha-androstan-17-beta-ol-3-one by rat prostate in vivo and in vitro. J Biol Chem. Apr. 25, 1968;243(8):2012-21.
Chen, et al. Molecular determinants of resistance to antiandrogen therapy. Nat Med. Jan. 2004;10(1):33-9.

(Continued)

*Primary Examiner* — Leslie A. Royds Draper
(74) *Attorney, Agent, or Firm* — Wilson Sonsini Goodrich & Rosati

(57) ABSTRACT

Described herein are compounds, methods of making such compounds, pharmaceutical compositions, and medicaments comprising such compounds, and methods of using such compounds to treat androgen receptor mediated diseases or conditions. Such compounds include inhibitors of cytochrome $C17_\alpha$-hydroxylase/$C_{17,20}$-lyase such as 3-β-Hydroxy-17-(1H-benzimidazol-1-yl)androsta-5,16-diene.

26 Claims, 13 Drawing Sheets

(56) References Cited

OTHER PUBLICATIONS

Chengjie, et al. Synthesis of pharmacological activity of some 17-[(2'-substituted)-4'-pyramidyl] androstene derivatives as inhibitors of human 17alpha-hydroxylase/C17,20-layse. J. Chinese Pharm. Sci. 2001; 10(1):3-8.
Choshi, et al. Total synthesis of grossularines-1 and -2. J. Org. Chem. 1995; 60:5899-5904.
Clement, et al. Three dimensional pharmacophore modeling of human CYP17 inhibitors. Potential agents for prostate cancer therapy. J Med Chem. Jun. 5, 2003;46(12):2345-51.
Crawford, et al. A controlled trial of leuprolide with and without flutamide in prostatic carcinoma. New Eng J Med. 1989; 321:419-424.
Crawford, et al. Treatment of newly diagnosed stage D2 prostate cancer with leuprolide and flutamide or leuprolide alone, phase III: prognostic significance of minimal disease. J. Urol. 1992; 147:417A.
Denis. Role of maximal androgen bloackade in advanced prostate cancer. The Prostate Supplement. 1994; 5:17-22.
Denmeade, et al. A history of prostate cancer treatment. Nat Rev Cancer. 2002; 2(5):389-96.
Evans, et al. methods for drug discovery: development of potent, selective, orally effective cholecystokinin antagonists. J Med Chem 1988; 31(12):2235-46.
Grigoryev, et al. Cytochrome P450c17-expressing *Escherichia coli* as a first-step screening system for 17alpha-hydroxylase-C17,20-lyase inhibitors. Anal Biochem. Feb. 15, 1999;267(2):319-30.
Grigoryev, et al. Effects of new 17alpha-hydroxylase/C(17,20)-lyase inhibitors on LNCaP prostate cancer cell growth in vitro and in vivo. Br J Cancer. Oct. 1999;81(4):622-30.
Haidar, et al. Effects of novel 17alpha-hydroxylase/C17, 20-lyase (P450 17, CYP 17) inhibitors on androgen biosynthesis in vitro and in vivo. J Steroid Biochem Mol Biol. Apr. 2003;84(5):555-62.
Haidar, et al. Novel steroidal pyrimidyl inhibitors of P450 17 (17 alpha-hydroxylase/C17-20-lyase). Arch Pharm (Weinheim). Dec. 2001;334(12):373-4.
Hall. Cytochrome P-450 C21scc: one enzyme with two actions: hydroxylase and lyase. J Steroid Biochem Mol Biol. 1991;40(4-6):527-32.
Handratta, et al. Novel C-17-heteroaryl steroidal CYP17 inhibitors/antiandrogens: synthesis, in vitro biological activity, pharmacokinetics, and antitumor activity in the LAPC4 human prostate cancer xenograft model. J Med Chem. Apr. 21, 2005;48(8):2972-84.
Handratta, et al. Potent CYP17 inhibitors: improved syntheses, pharmacokinetics and anti-tumor activity in the LNCaP human prostate cancer model. J Steroid Biochem Mol Biol. Oct. 2004;92(3):155-65.
Hartmann, et al. Synthesis and evaluation of novel steroidal oxime inhibitors of P450 17 (17 alpha-hydroxylase/C17-20-lyase) and 5 alpha-reductase types 1 and 2. J Med Chem. Nov. 2, 2000;43(22):4266-77.
Huggins, et al. Studies in prostate cancer: The effects of castration on advanced carcinoma of the prostate gland. Arch Surg. 1941; 43(2):209-223.
Humber, et al. Synthesis and biological activity of some cardiotonic compounds related to digitoxigenin. Steroids. Aug. 1983;42(2):189-202.
International search report dated Oct. 7, 2009 for PCT/US2009/036891.
Jarman, et al. The 16,17-double bond is needed for irreversible inhibition of human cytochrome p45017alpha by abiraterone (17-(3-pyridyl)androsta-5, 16-dien-3beta-ol) and related steroidal inhibitors. J Med Chem. Dec. 31, 1998;41(27):5375-81.
Jefcoate. Measurement of substrate and inhibitor binding to microsomal cytochrome P-450 by optical-difference spectroscopy. Methods Enzymol. 1978;52:258-79.
Jemal, et al. Cancer statistics, 2004. CA cancer J. Clin. 2004; 54(1):8-29.
Kadar, et al. Technical and safety aspects of blood and marrow transplantation using G-CSF mobilized family donors. Transfus Sci. Dec. 1996;17(4):611-8.

Kim, et al. Synergism of cytoplasmic kinases in IL6-induced ligand-independent activation of androgen receptor in prostate cancer cells. Oncogene. Mar. 11, 2004;23(10):1838-44.
Klein, et al. Progression of metastatic human prostate cancer to androgen independence in immunodeficient SCID mice. Nat Med. Apr. 1997;3(4):402-8.
Ling, et al. 17-Imidazolyl, pyrazolyl, and isoxazolyl androstene derivatives. Novel steroidal inhibitors of human cytochrome C17,20-lyase (P450(17 alpha). J Med Chem. Sep. 26, 1997;40(20):3297-304.
Long, et al. Antiandrogenic effects of novel androgen synthesis inhibitors on hormone-dependent prostate cancer. Cancer Res. Dec. 1, 2000;60(23):6630-40.
Matsunaga, et al. C17,20-lyase inhibitors I. Structure-based de novo design and SAR study of C17,20-lyase inhibitors. Bioorg Med. Chem. May 1, 2004;12(9):2251-73.
Matsunaga, et al. Synthetic studies on (1S)-1-(6,7-dimethoxy-2-naphthyl)-1-(1H-imidazol-4-yl)-2-methylpropan-1-ol as a selective C17,20-lyase inhibitor. Tetrahedron: Asymmetry. 2004; 15:2021-2028.
Matsunaga, et al. C(17,20)-lyase inhibitors. Part 2: design, synthesis and structure-activity relationships of (2-naphthylmethyl)-1H-imidazoles as novel C(17,20)-lyase inhibitors. Bioorg Med Chem. Aug. 15, 2004;12(16):4313-36.
McConnell. Physiologic basis of endocrine therapy for prostatic cancer. Urol Clin North Am. Feb. 1991;18(1):1-13.
Mohler, et al. The androgen axis in recurrent prostate cancer. Clin Cancer Res. Jan. 15, 2004;10(2):440-8.
Muscato, et al. Optimal dosing of ketoconazole (KETO) and hydrocortisone (HC) leads to long responses in hormone refractory prostate cancer. Proc ASCO. 1994; 229:701.
Nicolaou, et al. Natural Product-like Combinatorial Libraries Based on Privileged Structures. 1. General Principles and Solid-Phase Synthesis of Benzopyrans. J. Am. Chem. Soc. 2000; 122(41):9939-9953.
NIH Grant Project Reference No. 2RO1 CA27440-24A1, 2R01 CA27440-25A1 Revised Grant Renewal Application, approximate submission date Feb. 18, 2004; approximate award date Sep. 23, 2004.
NIH Grant Project Reference No. 3R)1 CA27440-22S1 Grant Application for Supplemental Funding, approximate date Jun. 21, 2001; approximate award date Aug. 17, 2001.
NIH Grant Project Reference No. 3RO1 CA27440-22S1 Grant Application for Supplemental Funding, approximate date Jun. 21, 2001; approximate award date Aug. 17, 2001.
NIH Grant Project Reference No. 3RO1 CA27440-23S1 Grant Continuation Application and Progress Report, approximate date May 3, 2002; approximate award date Jun. 21, 2002.
NIH Grant Project Reference No. 5R)1 CA27440-24S1 Grant Continuation Application and Progress Report, approximate date Apr. 1, 2003; approximate award date Jun. 3, 2003.
NIH Grant Project Reference No. 5RO1 CA27440-23 Grant Continuation Application and Progress Report, approximate date Jan. 21, 2002; approximate award date Apr. 29, 2002.
NIH Grant Project Reference No. 5RO1 CA27440-24 Grant Continuation Application and Progress Report, approximate date Feb. 20, 2003; approximate award date Jun. 3, 2003.
NIH Grant Project Reference No. 5RO1 CA27440-24S1 Grant Continuation Application and Progress Report, approximate date Apr. 1, 2003; approximate award date Jun. 3, 2003.
NIH Grant Project Reference No. 5RO1 CA27440-25 Grant Renewal Application, approximate submission date Jun. 26, 2003—Unfunded.
NIH Grant Project Reference No. 5RO1 CA27440-26 Grant Continuation Application and Progress Report, approximate submission date Jul. 1, 2005; approximate award date Aug. 2, 2005.
NIH Grant Project Reference No. 5RO1 CA27440-27 Grant Continuation Application and Progress Report, approximate submission date Apr. 26, 2006.
NIH Grant Project Reference No. 5RO1CA27440-27 ESNAP Report, approximate submission date May 8, 2006.
Njar, et al. Inhibitors of 17alpha-hydroxylase/17,20-lyase (CYP17): potential agents for the treatment of prostate cancer. Curr Pharm Des. Mar. 1999;5(3):163-80.

(56) References Cited

OTHER PUBLICATIONS

Njar, et al. Novel 17-azolyl steroids, potent inhibitors of human cytochrome 17 alpha-hydroxylase-C17,20-lyase (P450(17) alpha): potential agents for the treatment of prostate cancer. J Med Chem. Mar. 12, 1998;41(6):902-12.

Njar, et al. Nucleophilic vinylic 'Addition-Elimination' Substitution Reaction of 3B-Acetoxy-17-Chloro-16-Formylandrosta-5,16-Diene: A Novel and General Route to 17-Substituted Steroids Bioorganic and Medical Chemistry Letters 1996; 6(22):2777-27820.

Nnane, et al. Effects of novel 17-azolyl compounds on androgen synthesis in vitro and in vivo. J Steroid Biochem Mol Biol. Dec. 15, 1999;71(3-4):145-52.

O'Donnell, et al. Hormonal impact of the 17alpha-hydroxylase/C(17,20)-lyase inhibitor abiraterone acetate (CB7630) in patients with prostate cancer. Br J Cancer. Jun. 14, 2004;90(12):2317-25.

Office Action dated Jan. 31, 2011 for U.S. Appl. No. 12/577,094.
Office Action dated Mar. 12, 2010 for U.S. Appl. No. 11/817,550.
Office Action dated May 5, 2010 for U.S. Appl. No. 12/577,091.
Office Action dated May 7, 2010 for U.S. Appl. No. 12/577,092.
Office Action dated May 23, 2011 for U.S. Appl. No. 12/577,094.
Office Action dated May 25, 2010 for U.S. Appl. No. 12/577,096.
Office Action dated Jun. 1, 2010 for U.S. Appl. No. 12/577,090.
Office Action dated Jun. 1, 2011 for U.S. Appl. No. 12/623,257.
Office Action dated Jun. 2, 2010 for U.S. Appl. No. 11/817,550.
Office Action dated Sep. 8, 2011 for U.S. Appl. No. 12/577,096.
Office Action dated Sep. 9, 2011 for U.S. Appl. No. 12/577,090.
Office Action dated Oct. 20, 2010 for U.S. Appl. No. 12/623,257.
Office Action dated Oct. 28, 2010 for U.S. Appl. No. 12/577,091.
Office Action dated Oct. 28, 2010 for U.S. Appl. No. 12/577,092.
Office Action dated Oct. 29, 2010 for U.S. Appl. No. 12/577,090.
Office Action dated Nov. 1, 2010 for U.S. Appl. No. 12/577,096.

Ojida, et al. Stereocontrolled synthesis of (1S)-1-(1H-imidazol-4-yl)-1-(6-methoxy-2-naphthyl)-2-methylpropan-1-ol as a potent C17,20-lyase inhibitor. Tetrahedron: Asymmetry. 2004; 15L1555-1559.

Picard, et al. Synthesis and evaluation of 2'-substituted 4-(4'-carboxy- or 4'-carboxymethylbenzylidene)-N-acylpiperidines: highly potent and in vivo active steroid 5alpha-reductase type 2 inhibitors. J Med Chem. Aug. 1, 2002;45(16):3406-17.

Potter, et al. A convenient, large-scale synthesis of abiraterone acetate [3B-acetoxy-17-(3-pryidyl)androsta-5,16-diene], a potential new drug for the treatment of prostate cancer. Organic Preparations and Procedures Int. 1997; 29(1):123-134.

Potter, et al. Novel steroidal inhibitors of human cytochrome P45017 alpha (17 alpha-hydroxylase-C17,20-lyase): potential agents for the treatment of prostatic cancer. J Med Chem. Jun. 23, 1995;38(13):2463-71.

Randimbivololona, et al. Metabolism and excretion in bile of SC4453, a new semi-synthetic derivative of digoxin following an i.v. bolus injection in the guinea-pig. J Pharmacol. Jan.-Mar. 1984;15(1):53-64.

Recanatini, et al. A new class of nonsteroidal aromatase inhibitors: design and synthesis of chromone and xanthone derivatives and inhibition of the P450 enzymes aromatase and 17 alpha-hydroxylase/C17,20-lyase. Med Chem. Mar. 1, 2001;44(5):672-80.

Small, et al. Ketoconazole retains activity in advanced prostate cancer patients with progression despite flutamide withdrawal. J Urol. Apr. 1997;157(4):1204-7.

Supplementary European Search Report dated Jul. 29, 2009 for European Application No. EP 06736460.

Thompson, et al. Androgen antagonist activity by the antioxidant moiety of vitamin E, 2,2,5,7,8-pentamethyl-6-chromanol in human prostate carcinoma cells. Mol Cancer Ther. Aug. 2003;2(8):797-803.

Tindall, et al: Symposium on androgen action in prostate cancer. Cancer Res. Oct. 1, 2004;64(19):7178-80.

Trachtenberg, et al. Ketoconazole: a novel and rapid treatment for advanced prostatic cancer. J Urol. Jul. 1983;130(1):152-3.

Vasaitis, et al. The Effects of Novel Anti-Androgens on Androgen Receptor Action and Expression. Proceedings of the American Association for Cancer Research. 2006; 47:Abstract 5340. http://aacrmeetingabstracts.org/cgi/content/abstract/2006/1/252-d.

Vippagunta, et al. Crystalline solids. Adv Drug Deliv Rev. May 16, 2001;48(1):3-26.

Zhang, et al. A small composite probasin promoter confers high levels of prostate-specific gene expression through regulation by androgens and glucocorticoids in vitro and in vivo. Endocrinology. Dec. 2000;141(12):4698-710.

Office Action dated Oct. 5, 2011 for U.S. Appl. No. 12/577,094.

* cited by examiner

FIGURE 8

CYP17 and 5α-Reductase Activities and Androgen Receptor Binding of Novel 17-Heteroaryl Compounds

| compound[a] | CYP17 IC$_{50}$ (nM)[b] | 5α-reductase % inhibition at 10 μM (IC$_{50}$ (nM))[c] | | AR binding IC$_{50}$ (nM)[c] | |
|---|---|---|---|---|---|
| | | type 1[d] | type 2[e] | LNCaP | PC3-AR |
| 5 | 300.0 | 4 | 53 | 845 | 384 |
| 6 | 915.0 | [770] | [480] | 1200 | 242 |
| 9 | 1250.0 | nj[f] | 17 | - | - |
| 10 | 5817.4 | 21 | 56 | - | 366 |
| 14 | 3810.0 | - | - | - | 574 |
| 15 | 500.0 | - | - | - | - |
| for comparison: | | | | | |
| 16 | 50.0 | - | - | - | - |
| abiraterone | 800.0 | - | - | - | - |
| ketoconazole | 1100.0 | - | - | - | - |
| finasteride | - | [60.0] | [2.0] | - | - |
| casodex | - | - | - | 940 | - |
| flutamide | - | - | - | 12600 | 10985 |

FIGURE 12

Table 5.

| | | | Phases 1 and 2 | | | | | | | | | | | | Extension |
|---|---|---|---|---|---|---|---|---|---|---|---|---|---|---|---|
| | Screening | Enrollment | Post Treatment Visits every 2 weeks (±3 days) [plus off-week lab assessments (±3 days)[1]] | | | | | | | | | | | Trial Conclusion Visit/ET[d] 12 weeks (±5 days) | Extension Visits every 4 weeks |
| Day | -28 through 1 | 1[3] | 8 | 15 | 22 | 29 | 36 | 43 | 50 | 57 | 64 | 71 | 78 | 85 | |
| Assessment/Visit | 1 | 2 | 3 | 4 | 5 | 6 | 7 | 8 | 9 | 10 | 11 | 12 | 13 | 14 | |
| ICF | X | | | | | | | | | | | | | | |
| Inclusion/exclusion screen | X | | | | | | | | | | | | | | |
| Demographics | X | | | | | | | | | | | | | | |
| Medical/oncological history | X | | | | | | | | | | | | | | |
| Physical exam and vital signs | X | | | X | | X | | X | | X | | X | | X | X |
| 12-lead ECG (local) | X | X[4] | | X | | X | | X | | X | | X | | X | |
| CT/MRI and bone scans (local)[5] | X | | | | | | | | | | | | | X | X |
| Biopsy (PCF grant sites only)[6] | Optional | | | | | | | | | | | | | Optional | |
| Safety laboratories, urinalysis[7] | X | (X)[5] | X[9] | X | X[9] | X | X[9] | X | X[9] | X | X[9] | X | X[9] | X | X |
| Special laboratory tests | | X[6] | | X | | X | | X | | X | | X | | X | X[2] |
| PSA | | X | | X | | X | | X | | X | | X | | X | X |
| PK samples[11] | | X | | X | | X | | X | | X | | X | | X | |
| Train on use of Trial Drug | | X | | | | | | | | | | | | | |
| Accountability procedures | | | | X | | X | | X | | X | | X | | X | X |
| Dispense Trial Drug | | X | | X | | X | | X | | X | | X | | X[2] | X |
| Compliance diary-train/issue | | X | | X | | X | | X | | X | | X | | X[13] | X |
| Compliance diary- collect/monitor | | | | X | | X | | X | | X | | X | | X | |
| Adverse events[13] | X | X | | X | | X | | X | | X | | X | | X | X |
| Concomitant medication | X | X | | X | | X | | X | | X | | X | | X | X |

TREATMENT OF PROSTATE CANCER

This application claims the benefit of U.S. Provisional Application No. 61/232,257, filed Aug. 7, 2009, and U.S. Provisional Application No. 61/261,265, filed Nov. 13, 2009, each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Prostate cancer is the most common cancer in men. The majority of prostate cancer deaths are due to the development of metastatic disease that is unresponsive to conventional androgen deprivation therapy. Androgen deprivation therapy has been the standard of care in subjects with prostate cancer since the 1940s. Despite androgen deprivation, most subjects ultimately experience disease progression. For many years this later phase of the disease was called "hormone insensitive prostate cancer" or "androgen independent prostate cancer." It has since become clear that the prostate cancer that emerges after years of androgen deprivation therapy remains dependent upon androgen. The prostate cancer cells that have survived have gained the ability to import low levels of circulating androgens (expressed from adrenal glands), become much more sensitive to these low levels of testosterone, and actually synthesize testosterone within the prostate cancer cell itself. This stage of prostate cancer is now termed "castration resistant prostate cancer" or CRPC.

SUMMARY OF THE INVENTION

In some embodiments, the invention contemplates a pharmaceutical composition comprising Compound (1):

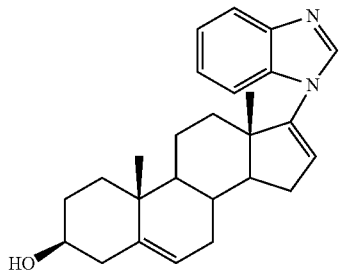

Compound (1)

wherein Compound (1) is in a micronized crystalline form characterized by a powder X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°, or a pharmaceutically acceptable salt, N-oxide, active metabolite, prodrug, or solvate thereof.

In some embodiments, the invention contemplates a method of providing treatment for prostate cancer in a subject, the method comprising administering to a subject in need or want thereof a pharmaceutical composition comprising Compound (1):

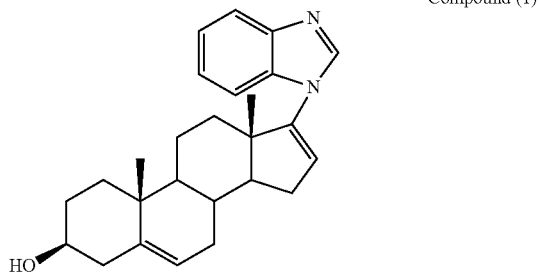

Compound (1)

wherein Compound (1) is in a micronized crystalline form characterized by a powder. X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°, or a pharmaceutically acceptable salt, N-oxide, active metabolite, prodrug, or solvate thereof.

BRIEF DESCRIPTION OF THE DRAWINGS

FIG. 8 is a table illustrating Compound (1) (described as compound 5) binding to androgen receptor.

FIG. 12 tabulates the schedule of procedures for the subjects of the study.

DETAILED DESCRIPTION OF THE INVENTION

Definitions

Figure 1:
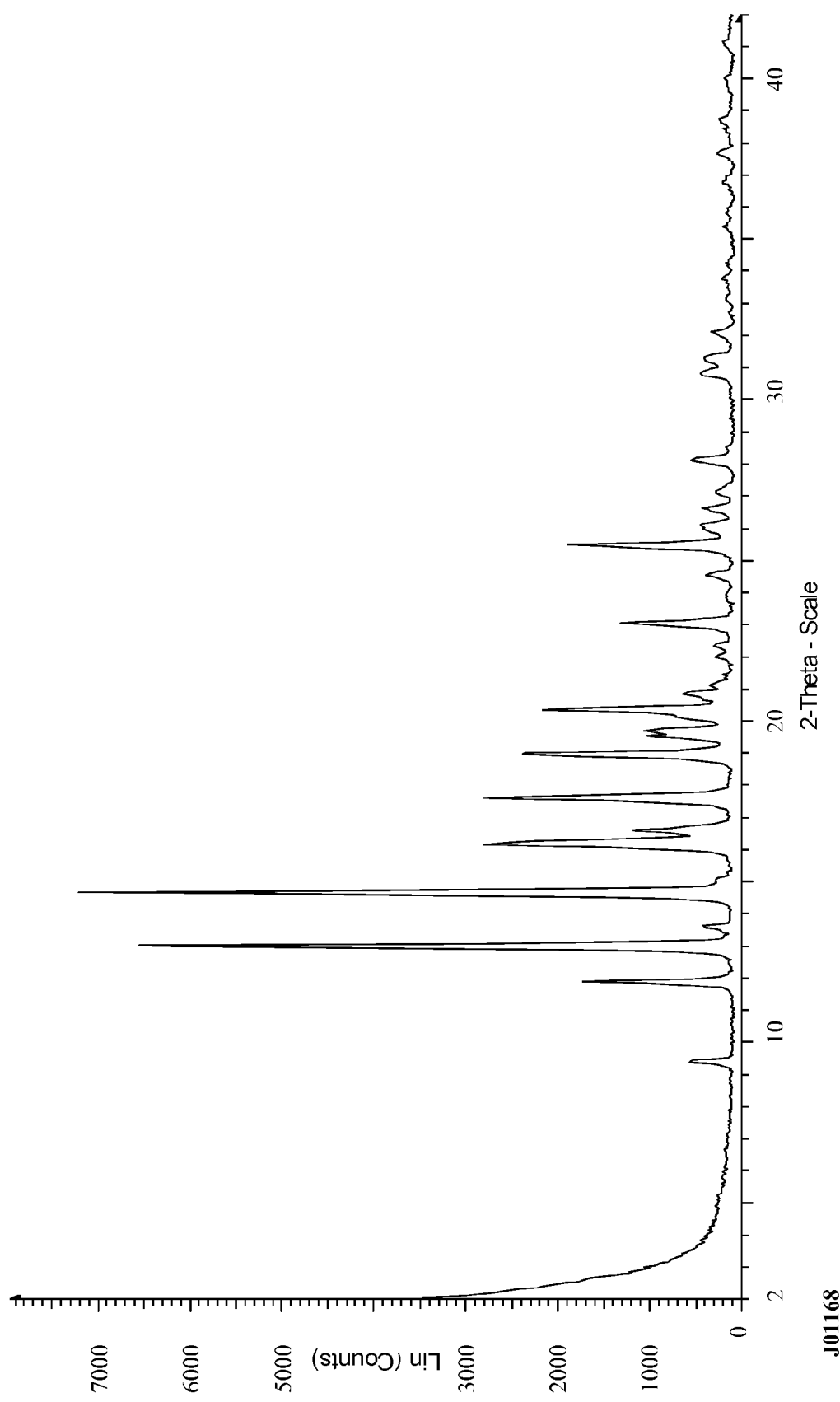
FIG. 1 is a representative powder X-ray diffraction diagram (XRPD) of Compound (1) Form I.

Adverse event: The term "adverse event" as used herein has its art understood meaning and refers to any untoward medical occurrence in a subject or clinical investigation subject administered a pharmaceutical product. An adverse event does not necessarily have to have a causal relationship with the treatment administered.

Adverse reaction: The term "adverse reaction" as used herein had its art understood meaning and refers to any noxious and unintended responses to a medicinal product related to any dose.

Combination Therapy: The term "combination therapy", as used herein, refers to those situations in which two or more different pharmaceutical agents are administered in overlapping regimens so that the subject is simultaneously exposed to both agents.

Dosing Regimen: A "dosing regimen", as that term is used herein, refers to a set of unit doses (typically more than one) that are administered individually separated by periods of time. The recommended set of doses (i.e., amounts, timing, route of administration, etc.) for a particular pharmaceutical agent constitutes its dosing regimen.

Initiation: As used herein, the term "initiation" when applied to a dosing regimen can be used to refer to a first administration of a pharmaceutical agent to a subject who has not previously received the pharmaceutical agent. Alternatively or additionally, the term "initiation" can be used to refer to administration of a particular unit dose of a pharmaceutical agent during therapy of a subject.

Pharmaceutical agent: As used herein, the phrase "pharmaceutical agent" refers to any agent that, when administered to a subject, has a therapeutic effect and/or elicits a desired biological and/or pharmacological effect.

Pharmaceutically acceptable ester: As used herein, the term "pharmaceutically acceptable ester" refers to esters which hydrolyze in vivo and include those that break down readily in the human body to leave the parent compound or a salt thereof.

Serious adverse event: The term "serious adverse event", as used herein, has its art-understood meaning and refers to any untoward medical occurrence that at any dose, for example, results in death, is life threatening, requires insubject hospitalization (or prolongation of existing hospitalization), results in persistent or significant disability or incapacity (defined as a substantial disruption of a subject's ability to carry out normal life functions), etc. In some embodiments, a serious adverse event is a "serious adverse drug experience", as that term is used by the United States Food and Drug Administration, for example as defined in 21 CFR §310.305(b), which says that a serious adverse event is any adverse drug experience occurring at any dose that results in any of the following outcomes: death, a life-threatening adverse drug experience, insubject hospitalization or prolongation of existing hospitalization, a persistent or significant disability/incapacity, or a congenital anomaly/birth defect. Important medical events that may not result in death, be life-threatening, or require hospitalization may be considered a serious adverse drug experience when, based upon appropriate medical judgment, they may jeopardize the subject or subject and may require medical or surgical intervention to prevent one of the outcomes listed in this definition. Examples of such medical events include allergic bronchospasm requiring intensive treatment in an emergency room or at home, blood dyscrasias or convulsions that do not result in insubject hospitalization, or the development of drug dependency or drug abuse.

Susceptible to: The term "susceptible to" is used herein to refer to an individual having higher risk (typically based on genetic predisposition, environmental factors, personal history, or combinations thereof) of developing a particular disease or disorder, or symptoms thereof, than is observed in the general population.

Therapeutically effective amount: The term "therapeutically effective amount" of a pharmaceutical agent or combination of agents is intended to refer to an amount of agent(s) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific pharmaceutical agent employed; the duration of the treatment; and like factors as is well known in the medical arts.

Treatment: As used herein, the term "treatment" (also "treat" or "treating") refers to any administration of a pharmaceutical agent that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Unit dose: The term "unit dose" or "dose", as used herein, refers to a discrete administration of a pharmaceutical agent, typically in the context of a dosing regimen.

Definitions of standard chemistry terms may be found in reference works, including Carey and Sundberg "ADVANCED ORGANIC CHEMISTRY $4^{TH}$ ED." Vols. A (2000) and B (2001), Plenum Press, New York, hereby incorporated by reference in its entirety. Unless otherwise indicated, conventional methods of mass spectroscopy, NMR, HPLC, protein chemistry, biochemistry, recombinant DNA techniques and pharmacology, within the skill of the art are employed.

Illustrative Biological Activity

Androgen Receptor (AR)

Androgens bind to a specific receptor, the androgen receptor (AR), inside the cells of target tissues. The AR is expressed in numerous tissues of the body and is the receptor through which the physiological as well as the pathophysiological effects of endogenous androgen ligands, such as testosterone (T) and dihydrotestosterone (DHT), are expressed. Structurally, the AR is composed of three main functional domains: the ligand binding domain (LBD), the DNA-binding domain, and amino-terminal domain. A compound that binds to the AR and mimics the effects of an endogenous AR ligand is referred to as an AR agonist, whereas a compound that inhibits the effects of an endogenous AR ligand is termed an AR antagonist. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue. In the prostate, androgens stimulate the growth of prostate tissue and prostate cancer cells by binding to the AR that is present within the cytoplasm of androgen sensitive tissue.

Compounds which selectively modulate AR are of clinical importance in the treatment of or prevention of a variety of diseases, conditions, and cancers, including, but not limited to, prostate cancer, benign prostatic hyperplasia, hirsutism in women, alopecia, anorexia nervosa, breast cancer, acne, musculoskeletal conditions, such as bone disease, hematopoietic conditions, neuromuscular disease, rheumatological disease, cancer, AIDS, cachexia, for hormone replacement therapy (HRT), employed in male contraception, for male performance enhancement, for male reproductive conditions, and primary or secondary male hypogonadism.

Castration Resistant Prostate Cancer

Agents that block the action (antiandrogens) of endogenous hormones (e.g., testosterone) are highly effective and routinely used for the treatment of prostate cancer (androgen ablation therapy). While initially effective at suppressing tumor growth, these androgen ablation therapies eventually fail in almost all subjects, leading to "castration resistant prostate cancer" ("CRPC"). Most, but not all, prostate cancer cells initially respond to androgen withdrawal therapy. However, with time, surviving populations of prostate cancer cells emerge because they have responded to the selective pressure created by androgen ablation therapy and are now refractory to it. Not only is the primary cancer refractory to available therapies, but cancer cells may also break away from the primary tumor and travel in the bloodstream, spreading the disease to distant sites (especially bone). Among other effects, this causes significant pain and further bone fragility.

It is contemplated that CRPC cells survive in an environment characterized by low levels of circulating androgens by amplifying at least three different pathways to enhance the response to the intracellular androgens that remain available. These include: (1) Up-regulation of the expression of the AR, which increases AR copy number and hence the sensitivity of the cells to low levels of circulating androgen induced by medical castration therapy; (2) Increase in the expression of enzymes involved in the importation of androgens that remain in cells after androgen deprivation therapy; (3) Increase in the expression of genes that regulate steroidogenesis, permitting the CRPC cells to synthesize their own androgens. A critical enzyme in the steroidogenic pathway is cytochrome $C_{17\alpha}$-hydroxylase/$C_{17,20}$-lyase (CYP17), the enzyme that controls androgen production in the adrenals, testes, and prostate.

Described herein, in certain embodiments, are compounds, methods of making such compounds, pharmaceutical compositions and medicaments comprising such compounds, and methods of using such compounds to treat androgen receptor mediated diseases or conditions including, but not limited to, prostate cancer, benign prostatic hyperplasia, hirsutism in women, alopecia, anorexia nervosa, breast cancer, acne, musculoskeletal conditions, such as bone disease, hematopoietic conditions, neuromuscular disease, rheumatological disease, cancer, AIDS, cachexia, for hormone replacement therapy (HRT), employed in male contraception, for male performance enhancement, for male reproductive conditions, and primary or secondary male hypogonadism. In some embodiments, the androgen receptor mediated disease or condition is prostate cancer. In some embodiments, the prostate cancer is castration resistant prostate cancer.

In some embodiments, the invention provides compounds, pharmaceutical compositions, and medicaments comprising such compounds, and methods of using such compounds that decrease androgen biosynthesis, decrease androgen receptor signaling and decrease androgen receptor sensitivity.

In one aspect, the compounds, pharmaceutical compositions and medicaments comprising such compounds, and methods of using such compounds decrease androgen biosynthesis. In some embodiments, the compounds disclosed herein inhibit the activity of enzymes that controls androgen production. In certain embodiments, the compounds disclosed herein inhibit the activity of cytochrome $C_{17\alpha}$-hydroxylase/$C_{17,20}$-lyase (CYP17).

In one aspect, the compounds, pharmaceutical compositions and medicaments comprising such compounds, and methods of using such compounds decrease androgen receptor signaling. In some embodiments, the compounds disclosed herein bind to the AR and are a competitive inhibitor of testosterone binding.

In one aspect, the compounds, pharmaceutical compositions and medicaments comprising such compounds, and methods of using such compounds decrease androgen receptor sensitivity. In some embodiments, the compounds disclosed herein reduce the content of AR protein within the cell and diminish the ability of the cell to be sustained by low levels of androgenic growth signals.

Exemplary Compounds

The compound of Formula (1), also described as Compound (1), pharmaceutically acceptable salts, pharmaceutically acceptable N-oxides, pharmaceutically active metabolites, pharmaceutically acceptable prodrugs, pharmaceutically acceptable polymorphs and pharmaceutically acceptable solvates thereof, modulate the activity of steroid hormone nuclear receptors and, as such, are useful for treating androgen receptor mediated diseases or conditions.

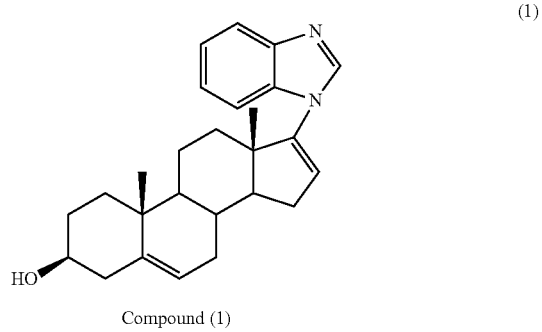 [SMILES: C[C@]12CC[C@H](O)CC1=CCC1C2CC[C@]2(C)C(n3cnc4ccccc43)=CCC12]

Compound (1)

(1)

Exemplary Synthesis of the Compounds

Compounds of Formula (1) (also described as Compound (1) or 3-β-Hydroxy-17-(1H-benzimidazol-1-yl)androsta-5,16-diene) may be synthesized using standard synthetic techniques known to those of skill in the art or using methods known in the art in combination with methods described herein. As one of skill in the art would understand, the solvents, temperatures and reaction conditions presented herein may vary according to the practice and knowledge of those of skill in the art.

The starting material used for the synthesis of the Compound (1) can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999) (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulae as provided herein.

Compound (1) can be prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid, metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Compound (1) can be prepared as a prodrug. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. Prodrugs may, for instance, be bioavailable by oral administration whereas the parent is not. The prodrug may also have improved solubility in pharmaceutical compositions over the parent drug. An example, without limitation, of a prodrug would be a derivative of Formula (1), which is administered as a hydrophilic ester (the "prodrug") to facilitate absorption in the gastrointestinal tract where improved water solubility is beneficial, but which then is metabolically hydrolyzed to a carboxylic acid and the active entity, Compound (1). A further example of a prodrug is a short peptide bonded to the hydroxyl group of Compound (1), wherein the peptide is metabolized to provide Compound (1).

Prodrugs may be designed as reversible drug derivatives for use as modifiers to enhance drug transport to site-specific tissues. The design of prodrugs to date has been to increase the effective water solubility of the therapeutic compound for targeting to regions where water is the principal solvent. See, e.g., Fedorak et al., Am. J. Physiol., 269:G210-218 (1995); McLoed et al., Gastroenterol, 106:405-413 (1994); Hochhaus et al., Biomed Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

Additionally, prodrug derivatives of Compound (1) can be prepared by methods known to those of ordinary skill in the art (e.g., for further details see Saulnier et al., (1994), Bioorganic and Medicinal Chemistry Letters, Vol. 4, p. 1985). Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

Sites on the aromatic ring portion of Compound (1) can be susceptible to various metabolic reactions, therefore incorporation of appropriate substituents on the aromatic ring structures, for example, halogens, can reduce, minimize or eliminate this metabolic pathway.

Various methods of making Compound (1) are contemplated and the following descriptions are provided as non-limiting examples. In some embodiments, one or more of the following chemical reactions is performed in an inert atmosphere, for example, nitrogen or argon. In some embodiments, the temperature of the reaction is monitored. In some embodiments, the reaction is monitored by HPLC or TLC. In some embodiments, the pH of the reaction is monitored. In some embodiments, the temperature of the reaction is controlled. In some embodiments, the purity of the product is determined by HPLC. In some embodiments, the experiments are run on small scale, medium scale, large scale, analytical scale, or manufacturing scale. In some embodiments, the product is clarified by filtration through a pad comprising one or more of silica gel and celite.

In some embodiments, the synthesis is performed on large scale. In some embodiments, large scale comprises a scale of about 1 to about 10 kg. In some embodiments, the synthesis is performed on manufacturing scale. In some embodiments, manufacturing scale comprises a scale of greater than about 10 kg. In some embodiments, manufacturing scale comprises a scale of about 10 to about 1,000 kg. In some embodiments, manufacturing scale comprises a scale of about 10 to about 100 kg. In some embodiments, manufacturing scale comprises a scale of about 10 to about 50 kg. In some embodiments, manufacturing scale comprises a scale of about 33.4 kg.

In some embodiments, an experiment is performed on a smaller scale to gather information to be used to plan or perform synthesis on a manufacturing scale. In some embodiments, the results obtained on the smaller scales are expected to be reproducible on manufacturing scale. In some embodiments, the results obtained on smaller scales are not expected to be reproducible on manufacturing scale. In some embodiments, the yields obtained on manufacturing scale are greater than the yields obtained on smaller scales. In some embodiments, the yields obtained on manufacturing scale are lesser than the yields obtained on smaller scales.

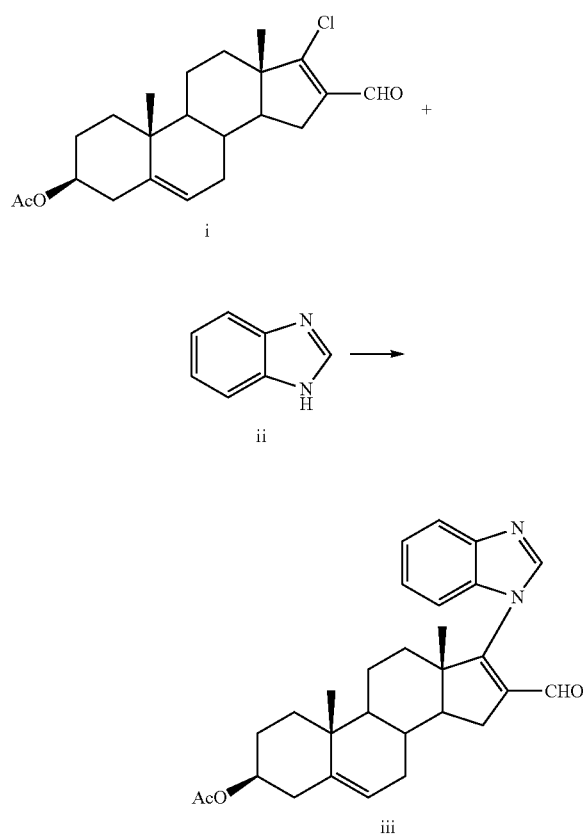

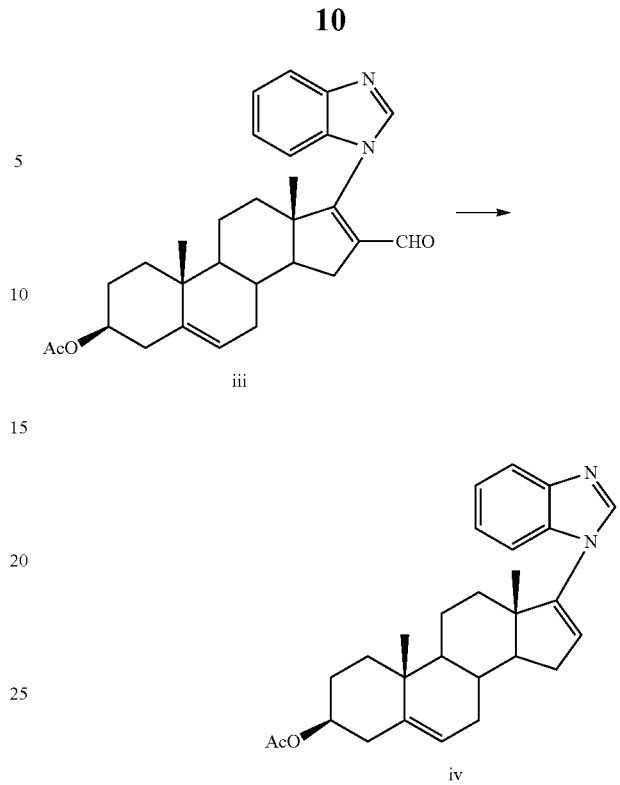

In one embodiment, a solution of a compound of Formula i in a solvent is prepared. A compound of Formula ii is then contacted to the solution, and the resultant mixture is heated in the presence of a base for a period of time sufficient to provide a compound of Formula iii. In some embodiments, the period of time is about 1 hour, about 2 hours, about 4 hours, about 8 hours, about 12 hours, or about 24 hours. In some embodiments, the time is from about 1 hour to about 24 hours. In some embodiments, the base comprises lithium carbonate, sodium carbonate, potassium carbonate, sodium bicarbonate, a sodium phosphate, or a potassium phosphate. In some embodiments, the solvent comprises DMF. In some embodiments, the temperature is about 50° C., about 70° C., about 100° C., about 150° C., or a temperature effective to sustain reflux conditions. In some embodiments, the temperature is from about 50° C. to about 200° C. The compound of Formula iii can be isolated from the reaction mixture and purified by any method known to one of skill in the art. Such methods include, but are not limited to, pouring an aqueous mixture into the reaction mixture, thereby effecting the precipitation of compound iii as a solid. The isolated compound of Formula iii may optionally be purified by any method known to one of skill in the art. Such methods include, but are not limited to, trituration with water.

In one embodiment, a solution of a compound of Formula iii in a solvent is prepared, and the solution is contacted with a catalyst for a period of time sufficient to provide a compound of Formula iv. In some embodiments, the period of time is about 1 hour, about 2 hours, about 4 hours, about 8 hours, about 12 hours, or about 24 hours. In some embodiments, the time is from about 1 hour to about 24 hours. In some embodiments, the catalyst comprises palladium on carbon, platinum on carbon, a transition metal salt, or a transition metal complex. In some embodiments, the solvent comprises N-methylpyrrolidone. In some embodiments, the temperature is about 50° C., about 70° C., about 100° C., about 150° C., about 190° C., about 200° C., or a temperature effective to sustain reflux conditions. In some embodiments, the temperature is from about 50° C. to about 250° C. The compound of Formula iv can be isolated from the reaction mixture and purified by any method known to one of skill in the art. Such methods include, but are not limited to, in-line filtration. The isolated compound of Formula iv may optionally be purified by any method known to one of skill in the art.

-continued

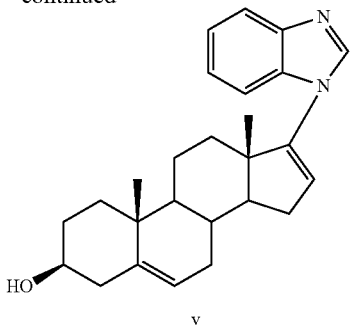

v

In one embodiment, a solution of a compound of Formula iv in a solvent is prepared, and the solution is contacted with a base for a period of time sufficient to provide a compound of Formula v (i.e., Compound (1)). In some embodiments, the period of time is about 1 hour, about 2 hours, about 4 hours, about 8 hours, about 12 hours, or about 24 hours. In some embodiments, the time is from about 1 hour to about 24 hours. In some embodiments, the base comprises lithium hydroxide, sodium hydroxide, potassium hydroxide, sodium methoxide, potassium methoxide, sodium ethoxide, potassium ethoxide, lithium carbonate, sodium carbonate, potassium carbonate, sodium bicarbonate, a sodium phosphate, or a potassium phosphate. In some embodiments, the solvent comprises water, methanol, ethanol, 2-propanol, t-butanol, or mixtures thereof. In some embodiments, the solvent comprises methanol and the base comprises sodium methoxide. In some embodiments, the temperature is about 35° C., about 50° C., about 70° C., about 100° C., or a temperature effective to sustain reflux conditions. In some embodiments, the temperature is from about 25° C. to about 100° C. The compound of Formula v can be isolated from the reaction mixture and purified by any method known to one of skill in the art. Such methods include, but are not limited to, extraction. The isolated compound of Formula v may optionally be purified by any method known to one of skill in the art. Such methods include, but are not limited to, trituration.

Exemplary Forms of Compound (1)

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of Compound (1) can be conveniently prepared or formed during the processes described herein. By way of example only, hydrates of Compound (1) can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Compound (1) includes crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

In one embodiment, Compound (1) is in a crystalline form denoted as Form I, characterized by powder X-ray reflections at about 13.0°, 14.6°, 16.3°, 17.6°, and 19.0°±0.2° 2θ. In some embodiments, Form I is characterized by additional peak powder X-ray reflections at about 11.8°, 20.2°, 22.9°, and 25.4°±0.2° 2θ. FIG. 1 is a representative powder X-ray diffraction diagram (XRPD) of Compound (1) Form I. In some embodiments, Form I is obtained, by way of example, from dissolving amorphous Compound (1) in a solvent and allowing the solvent to evaporate. In some embodiments, amorphous Compound (1) is suspended in the solvent and incubated alternatively at about 50°/room temperature in 8 hour cycles. The resulting solids in the suspension are filtered and analyzed. Solvents include but are not limited to heptane, dioxane, tert-butyl methyl ether, butyl acetate, isopropyl acetate, propanol, tetrahydrofuran, dichloromethane, methanol, nitromethane, and water.

Figure 2:
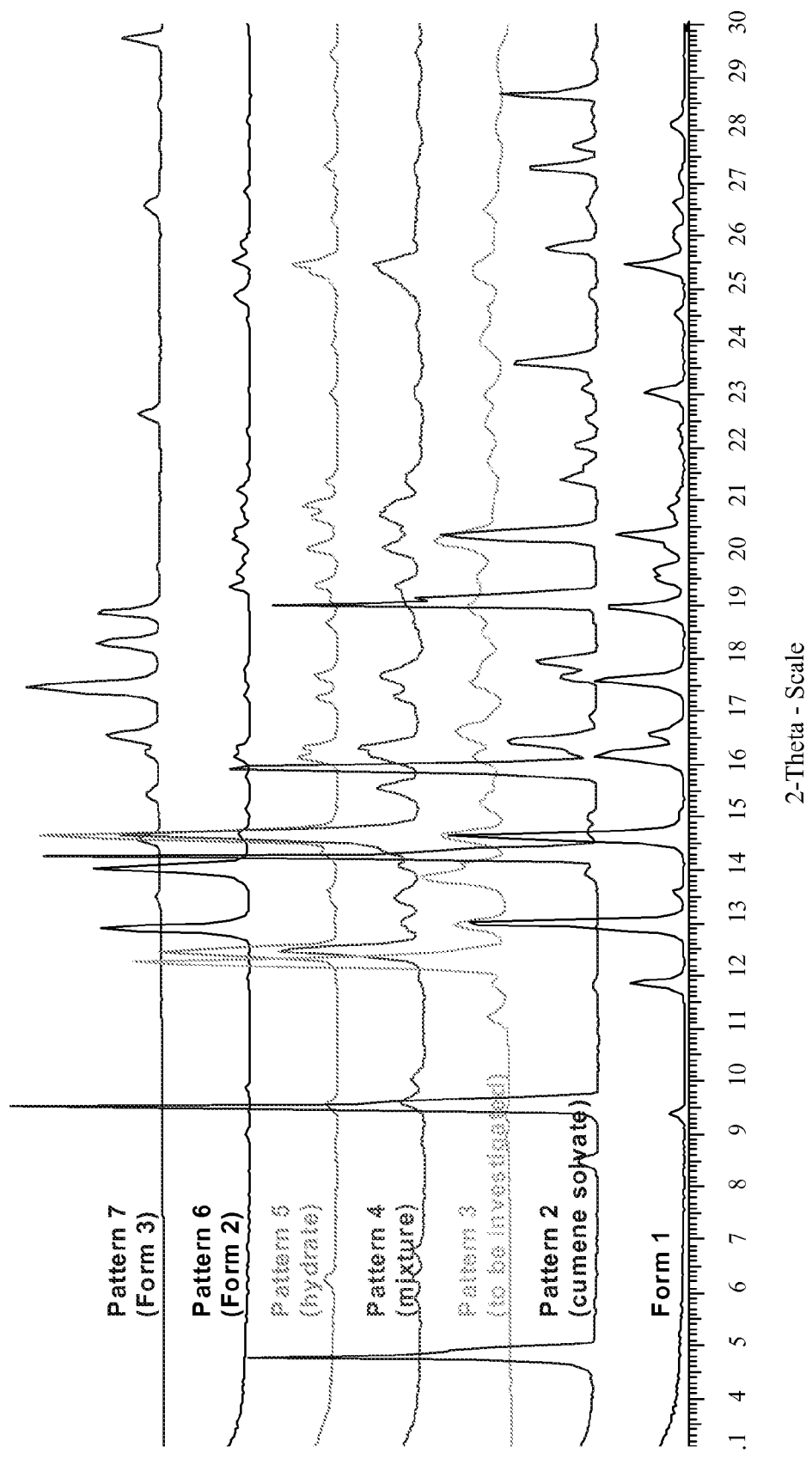
FIG. 2 is a representative powder X-ray diffraction diagram (XRPD) of several forms of Compound (1) including Form II.

In one aspect, Compound (1) is in a crystalline form denoted as Form II, characterized by powder X-ray reflections at about 13.1° and 14.1°±0.2° 2θ. FIG. 2 contains a representative powder X-ray diffraction diagram (XRPD) of Compound (1) Form II.

Figure 3:
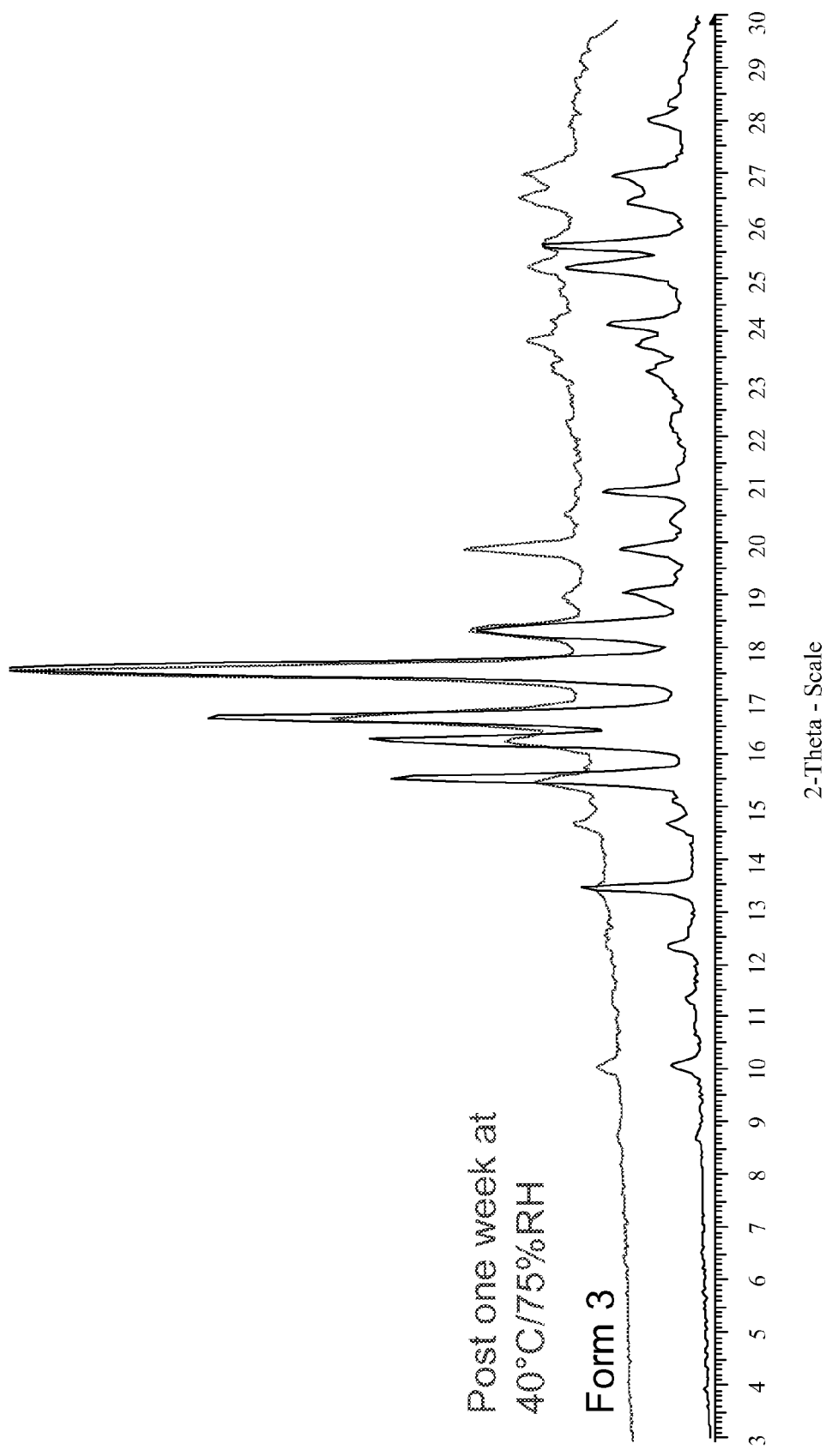
FIG. 3 is a representative powder X-ray diffraction diagram (XRPD) of Compound (1) Form III, both under standard conditions and after one week at 40° C.

In one aspect, Compound (1) is in a crystalline form denoted as Form III, characterized by powder X-ray reflections at about 17.2°, 18.5°, and 19.1°±0.2° 2θ. In some embodiments, Form III is characterized by additional peak powder X-ray reflections at about 16.2° and 29.6°±0.2° 2θ. FIG. 3 is a representative powder X-ray diffraction diagram (XRPD) of Compound (1) Form III.

Figure 4:
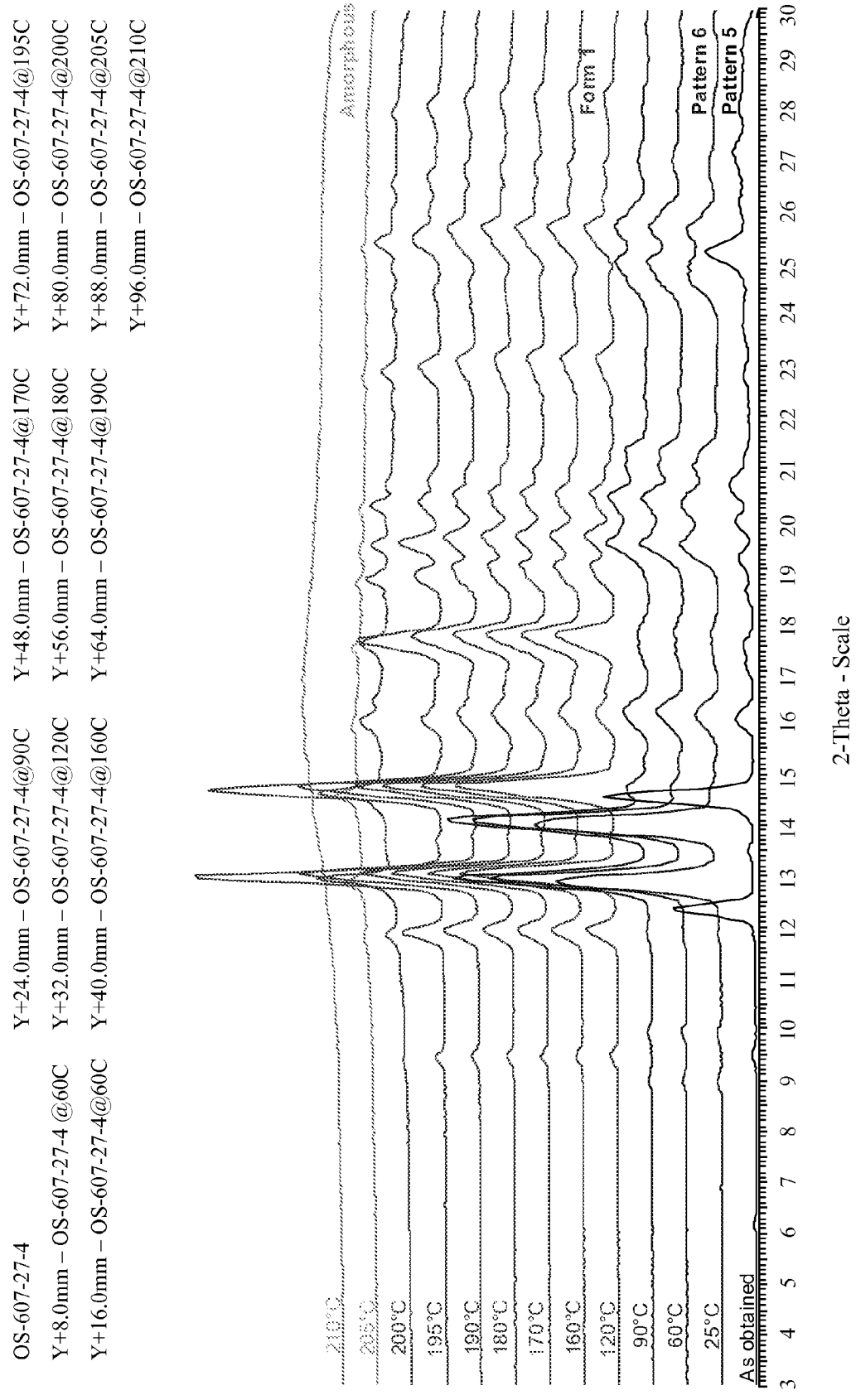
FIG. 4 is a representative powder X-ray diffraction diagram (XRPD) of Compound (1) Pattern 5, illustrating the conversion of Pattern 5 to other Patterns with increasing temperature.

In one aspect, Compound (1) is in a crystalline hydrate denoted as Pattern 5, characterized by powder X-ray reflections at about 12.5°, 14.8°, and 25.5°±0.2° 2θ. In some embodiments, Pattern 5 has a water content of relative humidity between about 40% to about 90%. FIG. 4 is a representative powder X-ray diffraction diagram (XRPD) of Compound (1) Pattern 5.

Figure 5:
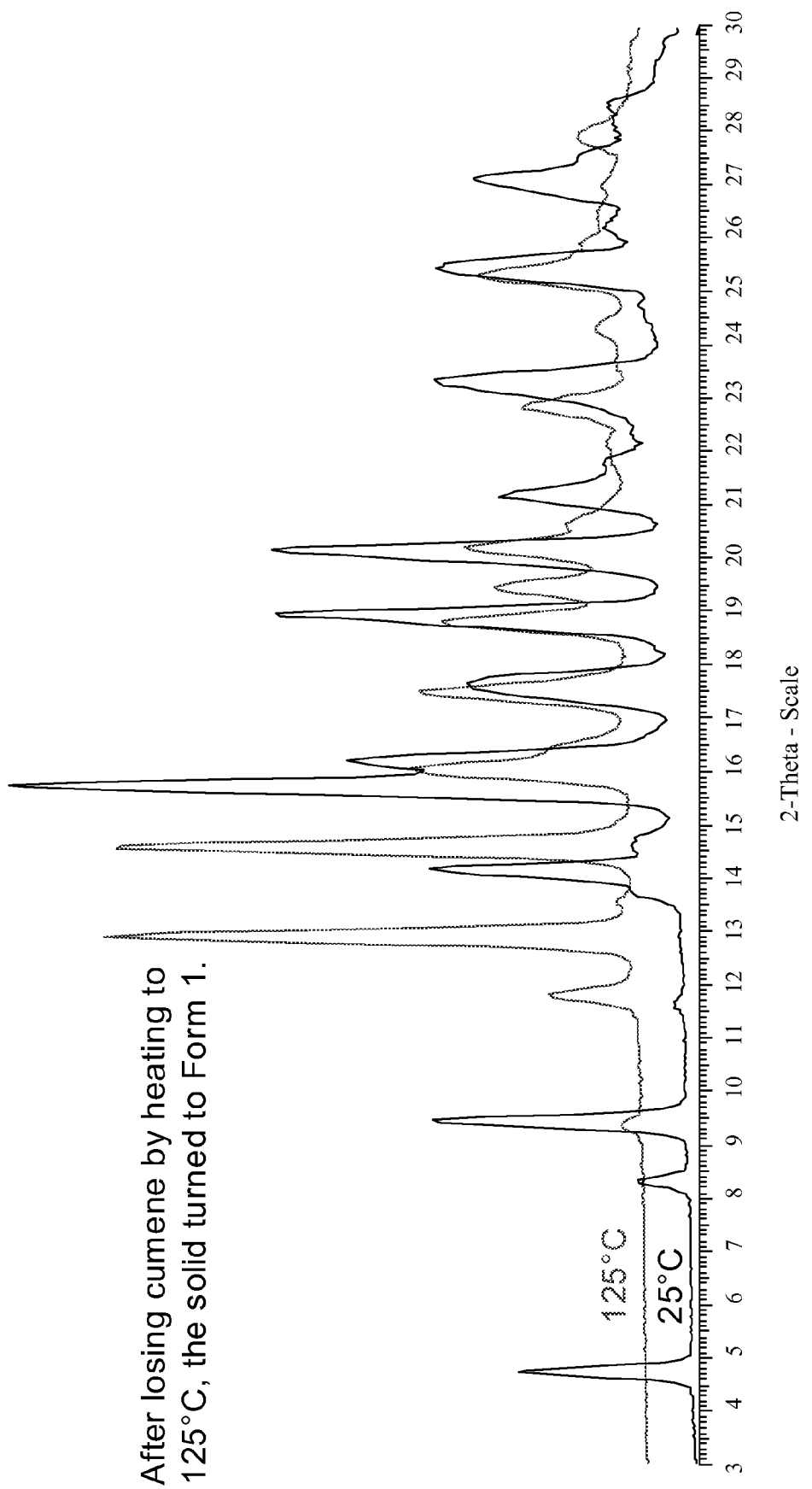
FIG. 5 is a representative powder X-ray diffraction diagram (XRPD) of Compound (1) Pattern 2, illustrating the return to Form 1 upon heating.

In one aspect, Compound (1) is in a crystalline cumene solvate denoted as Pattern 2, characterized by powder X-ray reflections at about 14.4°, 16.1°, 19.1° and 19.3°±0.2° 2θ. In some embodiments, Pattern 2 is characterized by additional peak powder X-ray reflections at about 20.4°, 23.6° and 28.7°±0.2° 2θ. In some embodiments, Pattern 2 has a cumene solvent content between about 20% to about 40%. In other embodiments, Pattern 2 has a cumene solvent content of about 25%. FIG. 5 is a representative powder X-ray diffraction diagram (XRPD) of Compound (1) Pattern 2.

In some embodiments, Compound (1) is substantially in one crystalline form or pattern. "Substantially" as used herein refers to greater than 80%. In some embodiments, Compound (1) is a mixture of two forms or patterns. In some embodiments, Compound (1) is a mixture of two or more forms or patterns. In the examples with mixtures of two forms or patterns, the mixture ratio can be about 1:100 to 100:1. In other embodiments, Compound (1) further includes amorphous forms. In certain embodiments, Compound (1) is substantially amorphous.

Exemplary Pharmaceutical Compositions/Formulations

A pharmaceutical composition, as used herein, refers to a mixture of Compound (1) with other chemical components, such as carriers, stabilizers, diluents, dispersing agents, suspending agents, thickening agents, and/or excipients. The pharmaceutical composition facilitates administration of the compound to an organism. Pharmaceutical composition containing Compound (1) can be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing Compound (1) in a targeted drug delivery system, for example, in a liposome coated with organ-specific antibody. The liposomes will be targeted to and taken up selectively by the organ. In addition, the pharmaceutical composition containing Compound (1) may be provided in the form of a rapid release formulation, in the form of an extended release formulation, or in the form of an intermediate release formulation.

For oral administration, Compound (1) can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a subject to be treated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. In certain instances, a gelatin is alkaline processed. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner. Parental injections may involve for bolus injection or continuous infusion. The pharmaceutical composition of Compound (1) may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Compound (1) can be administered topically and can be formulated into a variety of topically administrable compositions, such as solutions, suspensions, lotions, gels, pastes, medicated sticks, balms, creams or ointments. Such pharmaceutical composition can contain solubilizers, stabilizers, tonicity enhancing agents, buffers and preservatives.

Formulations suitable for transdermal administration of compounds having the structure of Formula (1) may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of Compound (1) can be accomplished by means of iontophoretic patches and the like. Additionally, transdermal patches can provide controlled delivery of Compound (1). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, Compound (1) may be in a form as an aerosol, a mist or a powder. Pharmaceutical compositions of Formula (1) are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

Compound (1) may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In practicing the methods of treatment or use provided herein, therapeutically effective amounts of Compound (1) provided herein are administered in a pharmaceutical composition to a mammal having a disease or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions comprising a compound of Formula (1) may be manufactured in a conventional manner, such as, by way of example only, by means of conventional mixing, dissolving, granulating, dragee-making, levigating, emulsifying, encapsulating, entrapping or compression processes.

The pharmaceutical compositions can include at least one pharmaceutically acceptable carrier, diluent or excipient and a compound of Formula (1) described herein as an active ingredient in free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A summary of types of pharmaceutical compositions may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference herein in its entirety.

Exemplary Methods of Administration and Treatment Methods

Compound (1) can be used in the preparation of medicaments for the treatment of diseases or conditions in which steroid hormone nuclear receptor activity contributes to the pathology and/or symptoms of the disease. In addition, a method for treating any of the diseases or conditions described herein in a subject in need of such treatment, involves administration of pharmaceutical compositions containing at least one compound of Formula (1), or a pharmaceutically acceptable salt, pharmaceutically acceptable N-oxide, pharmaceutically active metabolite, pharmaceutically-acceptable prodrug, or pharmaceutically acceptable solvate thereof, in therapeutically-effective amounts to said subject.

The compositions containing the compound(s) described herein can be administered for prophylactic and/or therapeutic treatments. In therapeutic applications, the compositions are administered to a subject already suffering from a disease or condition, in an amount sufficient to cure or at least partially arrest the symptoms of the disease or condition, or to cure, heal, improve, or ameliorate the condition itself. Amounts effective for this use will depend on the severity and course of the disease or condition, previous therapy, the subject's health status, weight, and response to the drugs, and the judgment of the treating physician.

Once improvement of the subject's conditions has occurred, a maintenance dose is administered if necessary. Subsequently, the dosage or the frequency of administration, or both, can be reduced, as a function of the symptoms, to a level at which the improved disease or condition is retained. Subjects can, however, require intermittent treatment on a long-term basis upon any recurrence of symptoms.

In certain instances, it may be appropriate to administer therapeutically effective amounts of at least one of the compounds described herein (or a pharmaceutically acceptable salts, pharmaceutically-acceptable N-oxides, pharmaceutically active metabolites, pharmaceutically-acceptable prodrugs, and pharmaceutically acceptable solvates thereof) in combination with another therapeutic agent. By way of example only, if one of the side effects experienced by a subject upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the subject is enhanced). Or, by way of example only, the benefit of experienced by a subject may be increased by administering one of the compounds described herein with another therapeutic agent (which also includes a therapeutic regimen) that also has therapeutic benefit. In any case, regardless of the disease or condition being treated, the overall benefit experienced by the subject may simply be additive of the two therapeutic agents or the subject may experience a synergistic benefit. Where the compounds described herein are administered in conjunction with other therapies, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents. Multiple therapeutic combinations are envisioned.

In addition, Compound (1) may also be used in combination with procedures that may provide additional or synergistic benefit to the subject. By way of example only, subjects are expected to find therapeutic and/or prophylactic benefit in the methods described herein, wherein pharmaceutical composition of Formula (1) and/or combinations with other therapeutics are combined with genetic testing to determine whether that individual is a carrier of a mutant gene that is known to be correlated with certain diseases or conditions.

Compound (1) and combination therapies can be administered before, during or after the occurrence of a disease or condition, and the timing of administering the composition containing a compound can vary. Thus, for example, the compounds can be used as a prophylactic and can be administered continuously to subjects with a propensity to conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 3 years and in some embodiments from about 1 month to about 10 years. In other embodiments, the compound is administered once a day from 90 days to 2 years.

The pharmaceutical composition described herein may be in unit dosage forms suitable for single administration of precise dosages. In unit dosage form, the formulation is divided into unit doses containing appropriate quantities of one or more compounds. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for Compound (1) described herein are from about 0.03 to 60 mg/kg per body weight. An indicated daily dosage in a larger mammal, including, but not limited to, humans, is in the range from about 1 mg to about 4000 mg, conveniently administered in one or more doses, including, but not limited to, up to four times a day or in retard form. Suitable unit dosage forms for oral administration comprise from about 1 mg to about 4000 mg active ingredient. In some embodiments, a single dose of compounds of Formula (1) is within the range of about 50 mg to about 2,000 mg. In some embodiments, a single dose of compounds of Formula (1) is about 90 mg, about 200 mg, about 250 mg, about 325 mg, about 650 mg, about 975 mg, about 1300 mg, about 1625 mg, or about 1950 mg. In some embodiments, an administration of compounds of Formula (1) of about 90 mg, about 325 mg, about 650 mg, about 975 mg, about 1300 mg, about 1625 mg, or about 1950 mg is given as multiple doses.

In some embodiments, the single dose of compounds of Formula (a) is between 90 to 2500 mgs and the compound is administered to a subject for between 90 days to two years.

Such dosages may be altered depending on a number of variables, not limited to the activity of the compound used, the disease or condition to be treated, the mode of administration, the requirements of the individual subject, the severity of the disease or condition being treated, and the judgment of the practitioner.

Pharmacokinetic and Pharmacodynamic Measurements

Pharmacokinetic and pharmacodynamic data can be obtained by known techniques in the art. Due to the inherent variation in pharmacokinetic and pharmacodynamic parameters of drug metabolism in human subjects, appropriate pharmacokinetic and pharmacodynamic profile components describing a particular composition can vary. Typically, pharmacokinetic and pharmacodynamic profiles are based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

The pharmacokinetic parameters can be any parameters suitable for describing the present composition. For example, the $C_{max}$ can be not less than about 500 ng/ml; not less than about 550 ng/ml; not less than about 600 ng/ml; not less than about 700 ng/ml; not less than about 800 ng/ml; not less than about 880 ng/ml, not less than about 900 ng/ml; not less than about 100 ng/ml; not less than about 1250 ng/ml; not less than about 1500 ng/ml, not less than about 1700 ng/ml, or any other $C_{max}$ appropriate for describing a pharmacokinetic profile of Compound (1). In some embodiments wherein the active metabolite is formed in vivo after administration of a drug to a subject; the $C_{max}$ can be not less than about 500 pg/ml; not less than about 550 pg/ml; not less than about 600 pg/ml; not less than about 700 pg/ml; not less than about 800 pg/ml; not less than about 880 pg/ml, not less than about 900 pg/ml; not less than about 1000 pg/ml; not less than about 1250 pg/ml; not less than about 1500 pg/ml, not less than about 1700 pg/ml, or any other $C_{max}$ appropriate for describing a pharmacokinetic profile of a compound formed in vivo after administration of Compound (1) to a subject.

The $T_{max}$ can be, for example, not greater than about 0.5 hours, not greater than about 1.0 hours, not greater than about 1.5 hours, not greater than about 2.0 hours, not greater than about 2.5 hours, or not greater than about 3.0 hours, or any other $T_{max}$ appropriate for describing a pharmacokinetic profile of Compound (1).

The $AUC_{(0-inf)}$ can be, for example, not less than about 590 ng·hr/mL, not less than about 1500 ng·hr/mL, not less than about 2000 ng·hr/mL, not less than about 3000 ng.times.hr/ml, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, or any other $AUC_{(0-inf)}$ appropriate for describing a pharmacokinetic profile of Compound (1). In some embodiments wherein an active metabolite is formed in vivo after administration of Compound (1) to a subject; the $AUC_{(0-inf)}$ can be, for example, not less than about 590 pg·hr/ mL, not less than about 1500 pg·hr/mL, not less than about 2000 pg·hr/mL, not less than about 3000 pg·hr/mL, not less than about 3500 pg·hr/mL, not less than about 4000 pg·hr/mL, not less than about 5000 pg·hr/mL, not less than about 6000 pg·hr/mL, not less than about 7000 pg·hr/mL, not less than about 8000 pg·hr/mL, not less than about 9000 pg·hr/mL, or any other $AUC_{(0-inf)}$ appropriate for describing a pharmacokinetic profile of a compound formed in vivo after administration of Compound (1) to a subject.

The plasma concentration of Compound (1) about one hour after administration can be, for example, not less than about 140 ng/ml, not less than about 425 ng/ml, not less than about 550 ng/ml, not less than about 640 ng/ml, not less than about 720 ng/ml, not less than about 750 ng/ml, not less than about 800 ng/ml, not less than about 900 ng/ml, not less than about 1000 ng/ml, not less than about 1200 ng/ml, or any other plasma concentration of Compound (1).

The pharmacodynamic parameters can be any parameters suitable for describing the present composition. For example, the pharmacodynamic profile can exhibit decreases in AR protein or endogenous androgens for, by way of example only, at least about 2 hours, at least about 4 hours, at least about 8 hours, at least about 12 hours or at least about 24 hours. The pharmacodynamic profile can exhibit an inhibition of androgen synthesizing enzymes, including CYP17, for, by way of example only, at least about 2 hours, at least about 4 hours, at least about 8 hours, at least about 12 hours or at least about 24 hours. The pharmacodynamic profile can exhibit reduction of androgen signaling, for, by way of example only, at least about 2 hours, at least about 4 hours, at least about 8 hours, at least about 12 hours or at least about 24 hours.

Exemplary Methods of Providing Therapy

The present invention provides therapeutic strategies for the treatment of prostate cancer in humans.

In some embodiments, the present invention provides preparations and regimens for the use of Compound 1 in the treatment of prostate cancer. In some embodiments, the prostate cancer is castration resistance prostate cancer. In some embodiments, the prostate cancer is chemotherapy naïve prostate cancer.

In some embodiments, the present invention provides therapeutic regimens that involve oral administration of Compound 1.

In some embodiments, the present invention provides therapeutic regimens that involve administration of multiple doses of Compound 1. In some embodiments, different doses are spaced apart in time. In some embodiments, all doses contain the same amount of Compound 1. In some embodiments, different doses contain different amounts of Compound 1. In some embodiments, different doses that are separated in time are separated from one another by the same amount of time; in some embodiments, different doses that are separated in time are separated from one another by different amounts of time. In some embodiments, the present invention provides dosing regimens that include administration of a plurality of doses separated by a regular time interval (or intervals), followed by a rest period, optionally followed by a second plurality of doses separated by a regular time interval (or intervals).

In some embodiments, at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168 or more doses of Compound 1 are administered. In some embodiments, at least 7, 14, 21, 28, 35, 42, 49, 56, 63, 70, 77, 84, 91, 98, 105, 112, 119, 126, 133, 140, 147, 154, 161, 168, or more doses of Compound 1 are administered.

In some embodiments, the invention contemplates a pharmaceutical composition comprising Compound (1):

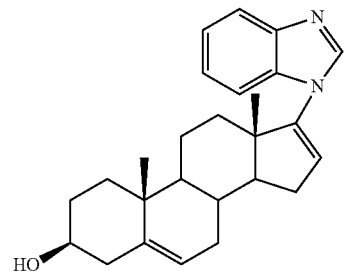

Compound (1)

as a micronized crystalline powder.

In some embodiments, the invention contemplates a pharmaceutical composition comprising Compound (1):

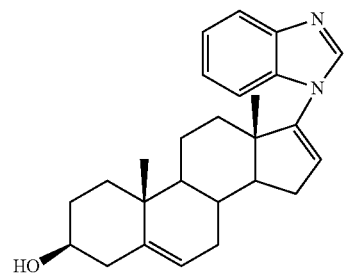

Compound (1)

wherein Compound (1) is a crystalline form characterized by a powder X-ray diffraction pattern having characteristic peaks expressed in angle 2-theta at approximately: a. 13.0°, 14.6°, 16.3°, 17.6°, and 19.0°, and optionally at approximately 11.8°, 20.2°, 22.9°, and 25.4°; b. 13.1° and 14.1°; c. 17.2°, 18.5°, and 19.1°, and optionally at approximately 16.2°, and 29.6°; d. 12.5°, 14.8°, and 25.5°; or e. 14.4°, 16.1°, 19.1° and 19.3°.

In some embodiments, the invention contemplates a pharmaceutical composition comprising Compound (1):

Compound (1)

wherein Compound (1) is in a micronized crystalline form characterized by a powder X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°, or a pharmaceutically acceptable salt, N-oxide, active metabolite, prodrug, or solvate thereof.

In some embodiments, the invention contemplates a pharmaceutical composition comprising Compound (1):

Compound (1)

wherein Compound (1) is in a micronized crystalline form characterized by a powder X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°.

In some embodiments, Compound (1) is present in an amount effective to treat an androgen receptor mediated disease or condition after administration to a subject.

In some embodiments, the androgen receptor mediated disease or condition is selected from the group consisting of prostate cancer, benign prostatic hyperplasia, hirsutism, alopecia, anorexia nervosa, breast cancer, and male hypergonadism.

In some embodiments, the androgen receptor mediated disease or condition is prostate cancer.

In some embodiments, the prostate cancer is castration resistant prostate cancer.

In some embodiments, Compound (1) is present in an amount effective to inhibit androgen biosynthesis, inhibit androgen receptor signaling and decrease androgen receptor sensitivity after administration to a subject.

In some embodiments, the compound inhibits androgen receptor signaling or decreases androgen receptor sensitivity.

In some embodiments, the androgen biosynthesis inhibition comprises inhibiting the activity of cytochrome $C_{17\alpha}$-hydroxylase/C17, 20-lyase (CYP17).

In some embodiments, the androgen receptor signaling inhibition comprises competitive inhibition of testosterone binding.

In some embodiments, the decrease in androgen receptor sensitivity comprises a reduction of the content of androgen receptor protein within the cell, and a diminished ability of the cell to be sustained by low levels of androgenic growth signals.

In some embodiments, the composition is formulated for administration to a subject parenterally, intravenously, intramuscularly, intradermally, subcutaneously, intraperitoneally, orally, buccally, sublingually, mucosally, rectally, transcutaneously, transdermally, ocularly, or by inhalation.

In some embodiments, the composition is formulated for administration to a subject as a tablet, a capsule, a cream, a lotion, an oil, an ointment, a gel, a paste, a powder, a suspension, an emulsion, or a solution.

In some embodiments, the composition is formulated for administration to a subject as a capsule.

The pharmaceutical composition of any of the preceding claims, wherein the composition is formulated for administration to a subject as a tablet.

In some embodiments, the capsule comprises Compound (1) as a powder.

In some embodiments, the powder is micronized.

In some embodiments, the composition comprises about 50 mg to about 500 mg of Compound (1).

In some embodiments, the composition comprises about 90 mg of Compound (1).

In some embodiments, the composition comprises about 325 mg of Compound (1).

In some embodiments, the composition is formulated for administration to a subject, one, two, three, four, five, six, seven, eight, nine, or ten times per day.

In some embodiments, the composition is formulated to be administered to a subject for the treatment of prostate cancer.

In some embodiments, the composition is formulated to be administered to a subject for the treatment of castration resistant prostate cancer.

In some embodiments, the composition further comprises one or more pharmaceutically acceptable excipients.

In some embodiments, the pharmaceutically acceptable excipient comprises a filler, a disintegrant, a lubricant, a surfactant, a glidant, a binder, a sugar, a starch, a varnish, or a wax.

In some embodiments, compound (1) is a pharmaceutically acceptable salt, N-oxide, active metabolite, prodrug, crystalline polymorph, or solvate.

In some embodiments, the solvate comprises a cumene solvate or a hydrate.

In some embodiments, the crystalline polymorph comprises Form I, Form II, or Form III of Compound (1).

In some embodiments, the invention contemplates a crystalline form of Compound (1) (Form I)

Compound (1)

characterized by a powder X-ray diffraction pattern having characteristic peaks expressed in angle 2-theta at approximately 13.0°, 14.6°, 16.3°, 17.6°, and 19.0°.

In some embodiments, the crystalline form is further characterized by characteristic peaks expressed in angle 2-theta at approximately 11.8°, 20.2°, 22.9°, and 25.4°.

In some embodiments, the invention contemplates a crystalline form of Compound (1)

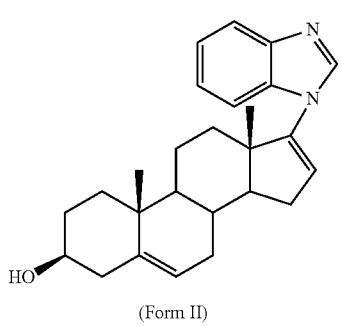

Compound (1)

(Form II)

characterized by a powder X-ray diffraction pattern having characteristic peaks expressed in angle 2-theta at approximately 13.1° and 14.1°.

In some embodiments, the invention contemplates a crystalline form of Compound (1)

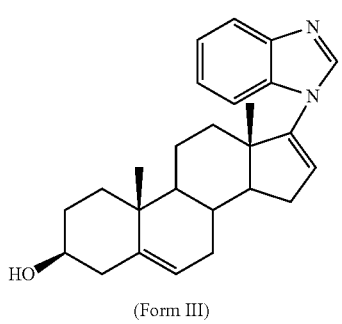

Compound (1)

(Form III)

characterized by a powder X-ray diffraction pattern having characteristic peaks expressed in angle 2-theta at approximately 17.2°, 18.5°, and 19.1°.

In some embodiments, the crystalline form is further characterized by characteristic peaks expressed in angle 2-theta at approximately 16.2°, and 29.6°.

In some embodiments, the invention contemplates a crystalline form of Compound (1)

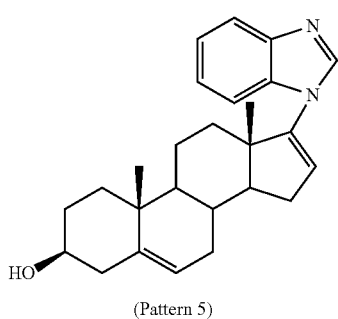

Compound (1)

(Pattern 5)

characterized by a powder X-ray diffraction pattern having characteristic peaks expressed in angle 2-theta at approximately 12.5°, 14.8°, and 25.5°.

In some embodiments, the invention contemplates a crystalline form of Compound (1)

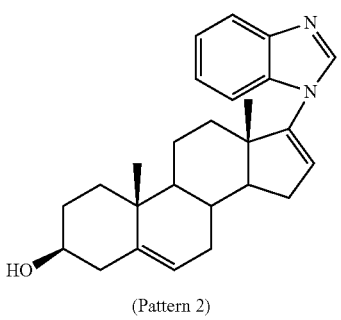

Compound (1)

(Pattern 2)

characterized by a powder X-ray diffraction pattern having characteristic peaks expressed in angle 2-theta at approximately 14.4°, 16.1°, 19.1° and 19.3°.

In some embodiments, the invention contemplates a method comprising contacting dimethylformamide, potassium carbonate, a compound of the formula:

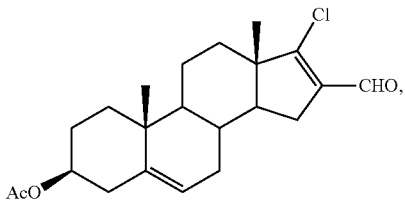 [SMILES: CC(=O)O[C@H]1CC[C@@]2(C)C(=CCC3C2CC[C@]2(C)C(Cl)=C(C=O)CC32)C1]

or analogue thereof, and a compound of the formula:

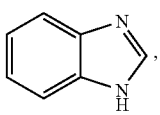

to make a compound of the formula:

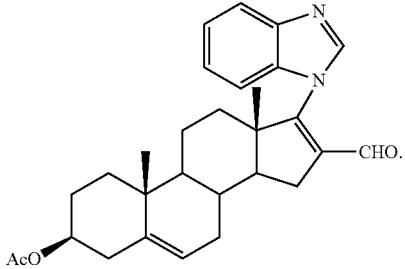 [SMILES: CC(=O)O[C@H]1CC[C@@]2(C)C(=CCC3C2CC[C@]2(C)C(n4cnc5ccccc54)=C(C=O)CC32)C1]

In some embodiments, the method further comprises contacting a compound of the formula:

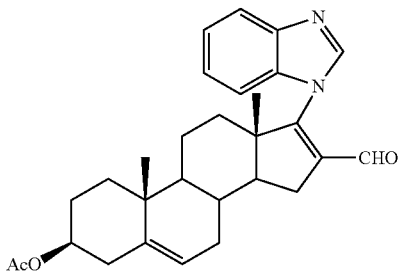 [SMILES: CC(=O)O[C@H]1CC[C@@]2(C)C(=CCC3C2CC[C@]2(C)C(n4cnc5ccccc54)=C(C=O)CC32)C1]

with 10% palladium on charcoal in N-methylpyrrolidone to produce a compound of the formula:

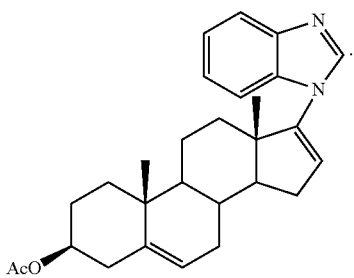 [SMILES: CC(=O)O[C@H]1CC[C@@]2(C)C(=CCC3C2CC[C@]2(C)C(n4cnc5ccccc54)=CCC32)C1]

In some embodiments, the method further comprises contacting a compound of the formula:

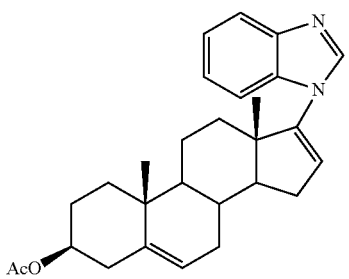 [SMILES: CC(=O)O[C@H]1CC[C@@]2(C)C(=CCC3C2CC[C@]2(C)C(n4cnc5ccccc54)=CCC32)C1]

with methanolic sodium methoxide to produce a compound of formula (I):

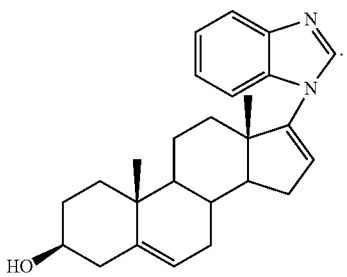

In some embodiments, the method is performed at a large scale or a manufacturing scale. In some embodiments, large scale is a scale of about 1 to about 10 kg. In some embodiments, manufacturing scale is a scale of greater than about 10 kg. In some embodiments, manufacturing scale is a scale of about 10 to about 1,000 kg. In some embodiments, manufacturing scale is a scale of about 10 to about 100 kg. In some embodiments, manufacturing scale is a scale of about 10 to about 50 kg. In some embodiments, manufacturing scale is a scale of about 33.4 kg.

In some embodiments, the invention contemplates a method of providing treatment for prostate cancer in a subject, the method comprising administering to the subject a pharmaceutical composition comprising a therapeutically-effective amount of Compound (1):

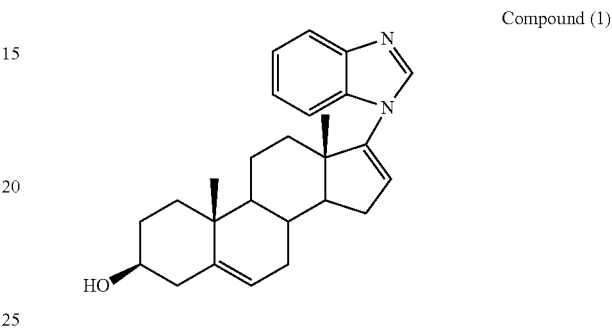

wherein Compound (1) is in a micronized crystalline form characterized by a powder X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°, or a pharmaceutically acceptable salt, N-oxide, active metabolite, prodrug, or solvate thereof.

In some embodiments, the invention contemplates a method of providing treatment for prostate cancer in a subject, the method comprising administering to the subject a pharmaceutical composition comprising a therapeutically-effective amount of Compound (1):

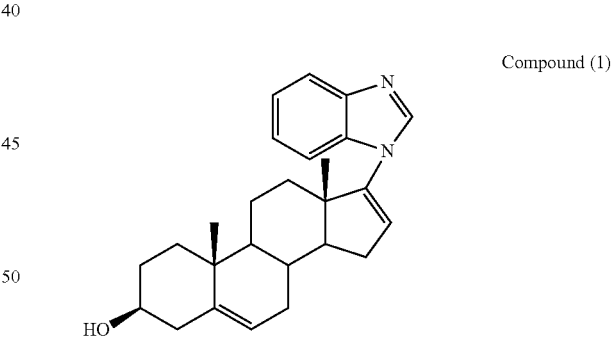

wherein Compound (1) is a crystalline form characterized by a powder X-ray diffraction pattern having characteristic peaks expressed in angle 2-theta at approximately: a. 13.0°, 14.6°, 16.3°, 17.6°, and 19.0°, and optionally at approximately 11.8°, 20.2°, 22.9°, and 25.4°; b. 13.1° and 14.1°; c. 17.2°, 18.5°, and 19.1°, and optionally at approximately 16.2°, and 29.6°; d. 12.5°, 14.8°, and 25.5°; or e. 14.4°, 16.1°, 19.1° and 19.3°.

In some embodiments, the invention contemplates a method of providing treatment for prostate cancer in a subject, the method comprising administering to the subject a pharmaceutical composition comprising a therapeutically-effective amount of Compound (1):

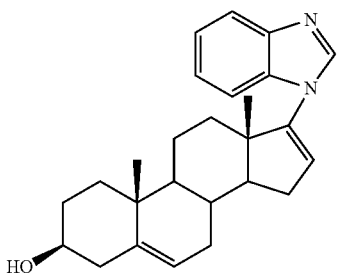

Compound (1)

wherein Compound (1) is in a micronized crystalline form characterized by a powder X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°.

In some embodiments, the invention contemplates a use of Compound (1) in formulating a medicament for the treatment of prostate cancer in a subject, the medicament comprising a therapeutically-effective amount of Compound (1):

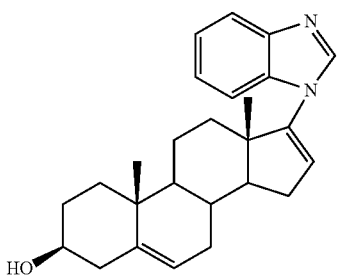

Compound (1)

wherein Compound (1) is in a micronized crystalline form characterized by a powder X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°, or a pharmaceutically acceptable salt, N-oxide, active metabolite, prodrug, or solvate thereof.

In some embodiments, the invention contemplates a use of Compound (1) in formulating a medicament for the treatment of prostate cancer in a subject, the medicament comprising a therapeutically-effective amount of Compound (1):

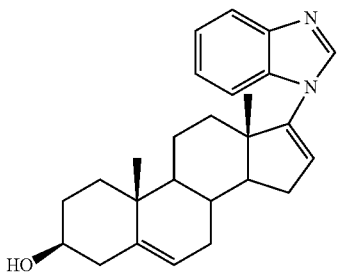

Compound (1)

wherein Compound (1) is a crystalline form characterized by a powder X-ray diffraction pattern having characteristic peaks expressed in angle 2-theta at approximately: a. 13.0°, 14.6°, 16.3°, 17.6°, and 19.0°, and optionally at approximately 11.8°, 20.2°, 22.9°, and 25.4°; b. 13.1° and 14.1°; c. 17.2°, 18.5°, and 19.1°, and optionally at approximately 16.2°, and 29.6°; d. 12.5°, 14.8°, and 25.5°; or e. 14.4°, 16.1°, 19.1° and 19.3°.

In some embodiments, the invention contemplates a use of Compound (1) in formulating a medicament for the treatment of prostate cancer in a subject, the medicament comprising a therapeutically-effective amount of Compound (1):

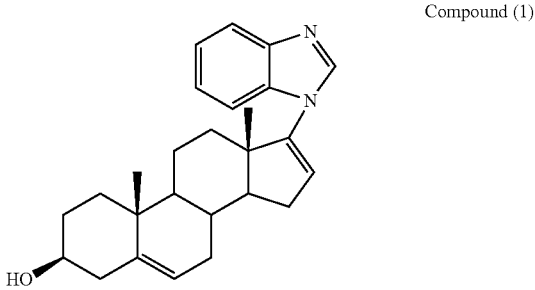 [SMILES: C[C@]12CC[C@H](O)CC1=CCC1C2CC[C@]2(C)C(n3cnc4ccccc43)=CCC12]

Compound (1)

wherein Compound (1) is in a micronized crystalline form characterized by a powder X-ray diffraction pattern having characteristic peaks expressed in angle 2-theta at approximately: a. 13.1° and 14.1°; b. 17.2°, 18.5°, and 19.1°, and optionally at approximately 16.2°, and 29.6°; c. 12.5°, 14.8°, and 25.5°; or d. 14.4°, 16.1°, 19.1° and 19.3°.

ILLUSTRATIVE EXAMPLES

The following examples provide illustrative methods for making and testing the effectiveness and safety of the Compound (1). These examples are provided for illustrative purposes only and not to limit the scope of the claims provided herein. All of the methods disclosed and claimed herein can be made and executed without undue experimentation in light of the present disclosure.

It will be apparent to those of skill in the art that variations may be applied to the methods and in the steps or in the sequence of steps of the method described herein without departing from the concept, spirit and scope of the claims. All such similar substitutes and modifications apparent to those skilled in the art are deemed to be within the spirit, scope and concept of the appended claims.

Example 1

Synthesis of Compounds of Formula (1)

Example 1A

Synthesis of 3-β-Acetoxy-17-(1H-benzimidazol-1-yl)-16-formyl-androsta-5,16-diene

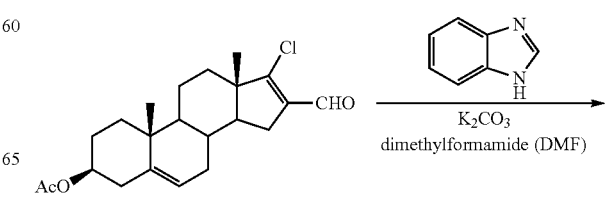

-continued

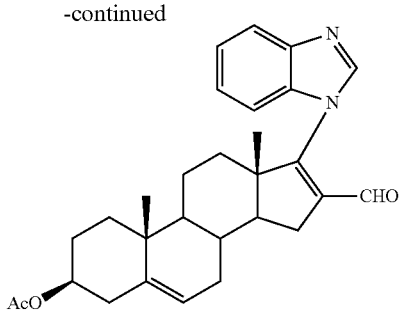

33.4 kg of 3-β-acetoxy-17-chloro-16-formylandrosta-5,16-diene was mixed with benzimidazole and potassium carbonate in dimethylformamide (DMF) and heated until the reaction was complete as determined by the amount of starting material remaining. After the reaction was complete, the reaction mixture was cooled and mixed with cooled water to quench the reaction. The solid was isolated from the quenched reaction mixture and washed sequentially with a mixture of DMF and water, water, dilute aqueous hydrochloric acid, water, dilute aqueous sodium hydrogen carbonate, and water. The intermediate product, 3-β-Acetoxy-17-(1H-benzimidazol-1-yl)-16-formylandrosta-5,16-diene, was subsequently dried.

Example 1B

Synthesis and Purification of 3-β-Acetoxy-17-(1H-benzimidazol-1-yl)androsta-5,16-diene

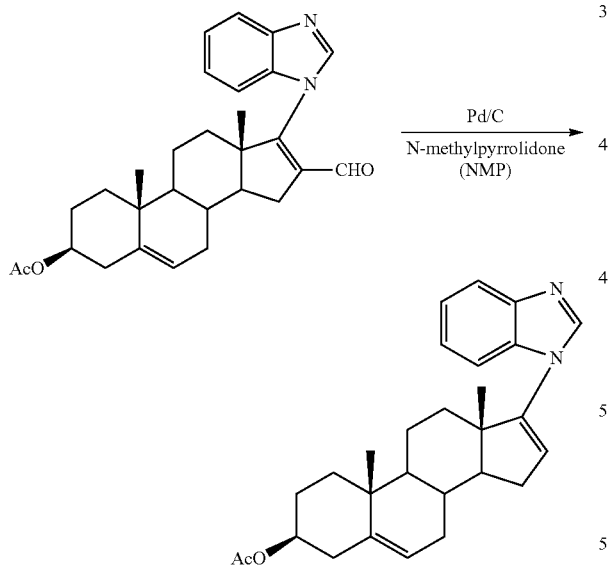

3-β-Acetoxy-17-(1H-benzimidazol-1-yl)-16-formylandrosta-5,16-diene was mixed with about 10% palladium on carbon (Pd/C) in N-methylpyrrolidone (NMP) and heated until the reaction was complete as determined by the 3-β-Acetoxy-17-(1H-benzimidazol-1-yl)-16-formyl-androsta-5,16-diene/3-β-Acetoxy-17-(1H-benzimidazol-1-yl)androsta-5,16-diene ratio in the reaction mixture. After the reaction was complete, the reaction mixture was cooled. Magnesium sulfate was added, and the resulting mixture was filtered. Water was added to the filtrate and the resulting mixture was stirred. The solid, crude 3-β-Acetoxy-17-(1H-benzimidazol-1-yl)androsta-5,16-diene was isolated from the water/NMP mixture, washed with a mixture of water and methanol, dried, and packaged.

The crude 3-β-Acetoxy-17-(1H-benzimidazol-1-yl)androsta-5,16-diene was dissolved in ethyl acetate and clarified. The volume of this mixture was reduced by vacuum distillation. The resulting mixture was cooled, and the solid was isolated, washed with cold ethyl acetate, and dried under vacuum. In some embodiments, a sample was subjected to an in-process test to determine impurity levels. If the impurity levels were not acceptable, a recrystallization process was repeated.

Example 1C

Synthesis and Purification of 3-β-Hydroxy-17-(1H-benzimidazol-1-yl)androsta-5,16-diene

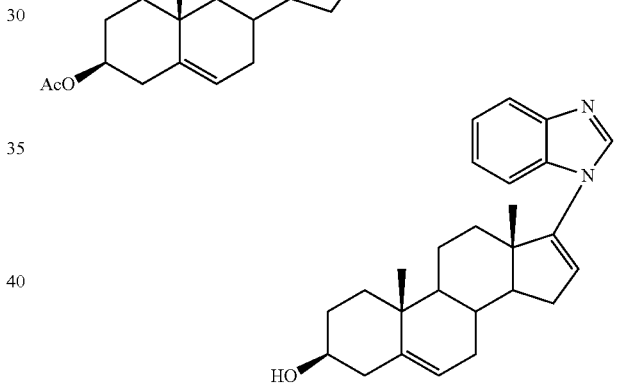

3-β-Acetoxy-17-(1H-benzimidazol-1-yl)androsta-5,16-diene was mixed with sodium methoxide in methanol and heated until the reaction was complete as determined by the amount of 3-β-Acetoxy-17-(1H-benzimidazol-1-yl)androsta-5,16-diene remaining. After the reaction was complete, the reaction mixture was cooled and mixed with water to quench the reaction. The resulting slurry was stirred and cooled further. The solid, crude 3-β-Hydroxy-17-(1H-benzimidazol-1-yl)androsta-5,16-diene was isolated from the quenched reaction mixture and washed with a mixture of methanol and water and then with water until the wash liquid was neutral, dried, and packaged.

The crude 3-β-Hydroxy-17-(1H-benzimidazol-1-yl)androsta-5,16-diene was dissolved in a mixture of methanol and ethyl acetate and clarified. The product was transferred from the methanol/ethyl acetate solution to ethyl acetate alone by solvent exchange. The resulting mixture was cooled, and the solid was isolated, washed with cold ethyl acetate, and dried under vacuum. In some embodiments, a sample was subjected to an in-process test to determine impurity levels. If the impurity levels were not acceptable, a recrystallization process was repeated.

Example 2

Crystalline Polymorphic Forms of Compound (1)

Example 2A

Instruments and Methodology

X-Ray Powder Diffraction (XRPD):

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consisted of a single Gael multilayer mirror coupled with a pinhole collimator of 0.3 mm.

The beam divergence, i.e. the effective size of the X-ray beam on the sample was approximately 4 mm. A θ-θ continuous scan mode was employed with a sample—detector distance of 20 cm which gave an effective 2θ range of 3-30° 2θ. Typically the sample was exposed to the X-ray beam for 120 seconds. The software used for data collection was GADDS for WNT 4.1.16 and the data were analyzed and presented using Diffrac Plus EVA v 9.0.0.2 or v 13.0.0.2. Samples run under ambient conditions were prepared as flat plate specimens using powder as received without grinding. Samples run under non-ambient conditions were mounted on a silicon wafer with heat-conducting compound.

Nuclear Magnetic Resonance ($^1$H-NMR): NMR spectra were collected on a Bruker 400 MHz instrument equipped with an auto-sampler and controlled by a DRX400 console. Automated experiments were acquired using ICON-NMR v4.0.4 (build 1) running with Topspin v 1.3 (patch level 8) using the standard Bruker loaded experiments. For non-routine spectroscopy, data were acquired through the use of Topspin alone. Samples were prepared in $d_6$-DMSO, unless otherwise stated. Off-line analysis was carried out using ACD SpecManager v 12.00 (build 29094).

Differential Scanning Calorimetry (DSC):

DSC data were collected on a TA Instruments Q2000 equipped with a 50 position auto-sampler. The instrument was calibrated for energy and temperature calibration using certified indium. Typically 0.5-3 mg of each sample, in a pin-holed aluminum pan, was heated at 10° C.min$^{-1}$ from 25° C. to 250° C. A nitrogen purge at 50 mL/min was maintained over the sample.

Thermo-Gravimetric Analysis (TGA):

TGA data were collected on a TA Instruments Q500 TGA, equipped with a 16 position auto-sampler. The instrument was temperature calibrated using certified Alumel. Typically 5-30 mg of each sample was loaded onto a tared platinum crucible and aluminum DSC pan, and heated at 10° C./min from ambient temperature to 300° C. A nitrogen purge at 60 mL/min was maintained over the sample.

Gravimetric Vapor Sorption (GVS):

Sorption isotherms were obtained using a SMS DVS Intrinsic moisture sorption analyzer, controlled by SMS Analysis Suite software. The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). 5-20 mg of sample was placed in a tared mesh stainless steel basket under ambient conditions. The sample was loaded and unloaded at 40% RH and 25° C. (typical room conditions). A moisture sorption isotherm was performed below:

| Parameters | Values |
|---|---|
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml · min$^{-1}$) | 200 |
| Temperature (° C.) | 25 |
| Stability (° C. · min$^{-1}$) | 0.2 |
| Sorption Time (hours) | 6 hour time out |

Chemical Purity Determination by HPLC:

Purity analysis was performed on an Agilent HP1100 series system equipped with a diode array detector and using ChemStation software vB.02.01-SR1 using one of the two methods detailed below.

| Sample Preparation | 0.5 mg/ml in acetonitrile:water 1:1 (unless otherwise stated) | | |
|---|---|---|---|
| Column: | Supelco Ascentis Express C18, 100 × 4.6 mm, 2.7 µm | | |
| Column Temperature (° C.): | 25 | | |
| Injection (µl): | 5 (unless otherwise stated) | | |
| Wavelength, Bandwidth (nm): | 255, 90 nm | | |
| Flow Rate (mL/min): | 2.0 | | |
| Phase A: | 0.1% TFA in water | | |
| Phase B: | 0.085% TFA in acetonitrile | | |
| | Time (min) | % Phase A | % Phase B |
| Timetable: | 0 | 95 | 5 |
| | 6 | 5 | 95 |
| | 6.2 | 95 | 5 |
| | 8 | 95 | 5 |

Polarized Light Microscopy (PLM):

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a X false-color filter.

Example 2B

Preparation of Amorphous Compound (1)

Figure 6:
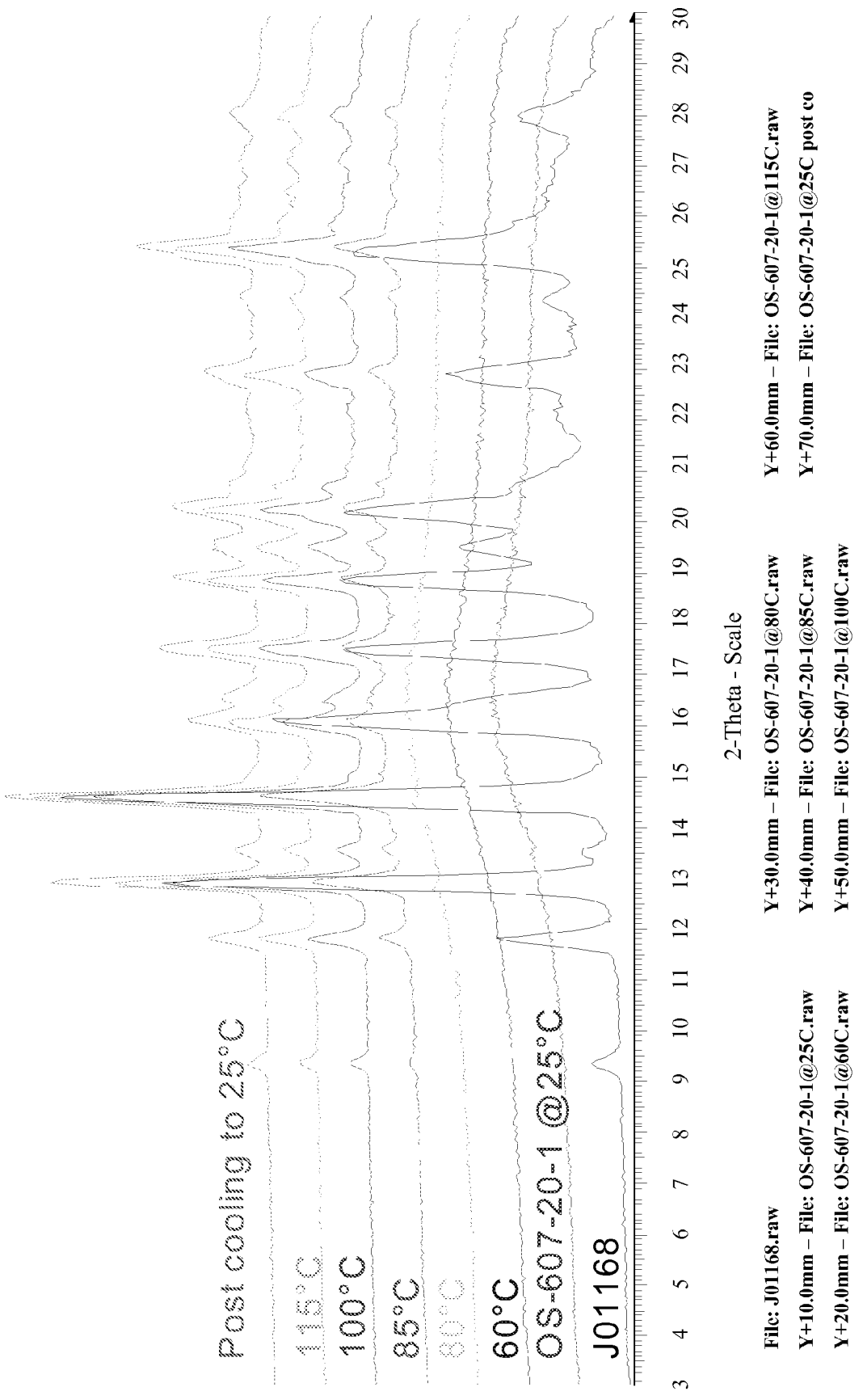
FIG. 6 is a representative powder X-ray diffraction diagram (XRPD) of amorphous Compound (1) at various temperatures.

Compound (1) was dissolved in tert-butanol. The sample was subjected to a lyophilization process where the sample was filtered, frozen, and freeze dried. A solid was collected and characterized by XRPD, $^1$H-NMR, modulated DSC, HPLC purity and optical microscopy. The preparation of the amorphous material was repeated to check reproducibility. FIG. 6 is an XRPD of the solids obtained by lyophilization.

Example 2C

Preparation and Analysis of Compound (1) Form I

Figure 7:
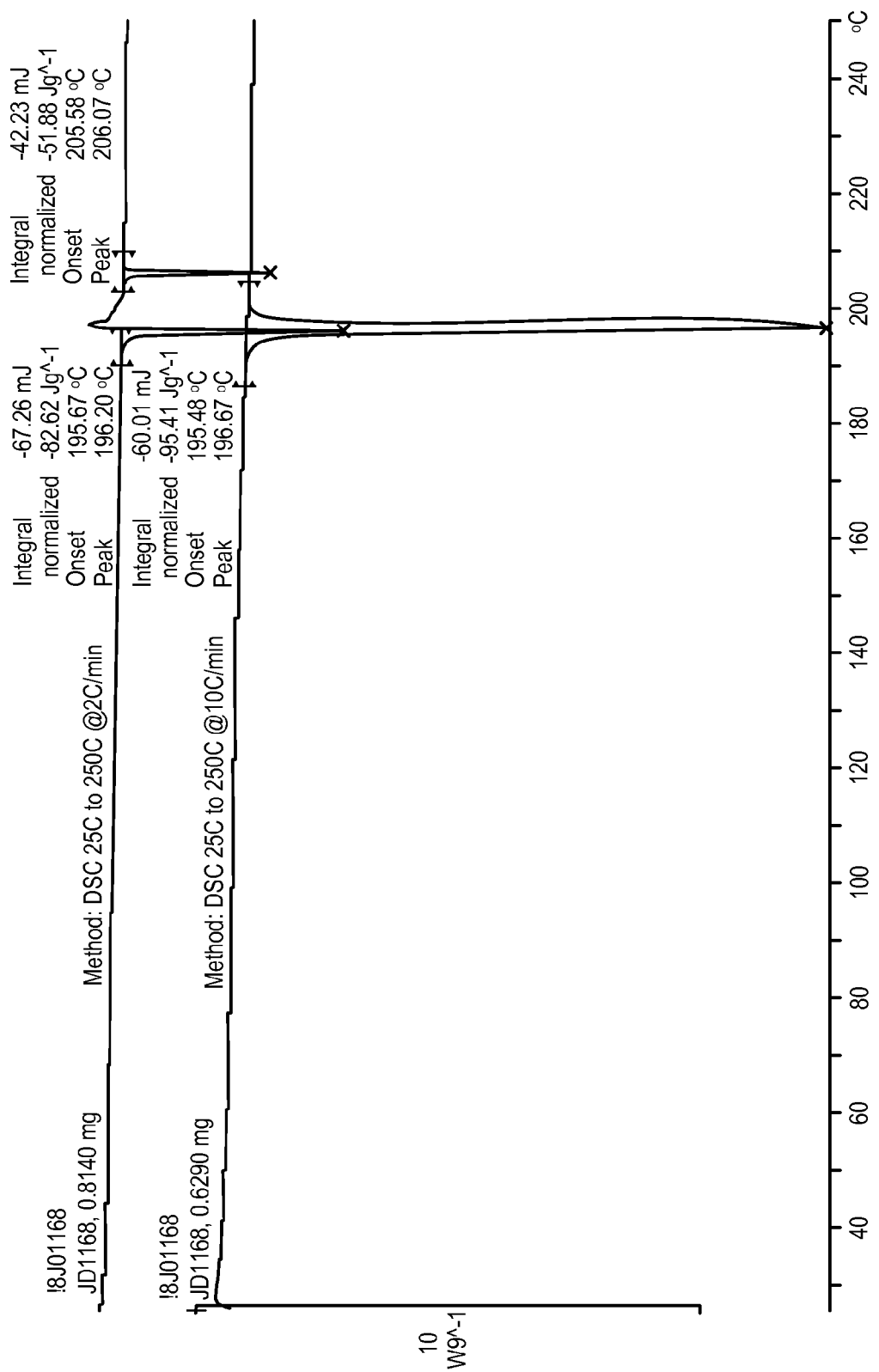
FIG. 7 is a representative thermogram of Compound (1) Form I.

Compound (1) was dissolved in methanol. The methanol in the solution is allowed to evaporate and the resulting solid was collected and characterized by XRPD, $^1$H-NMR, DSC, HPLC purity and optical microscopy. FIG. 1 is an XRPD of Form I. Thermal analysis of Form I by TGA was carried out at a heating rate of 10° C./min. No weight loss was observed in the TGA thermogram (FIG. 7), indicating that the material was a non-solvated crystalline form. Degradation of the sample began at ~230° C. DSC analysis (FIG. 7) showed a sharp endotherm at 196° C. (91.7 J/g) indicating the melting point of Compound (1) (Form 1).

Example 2D

Preparation and Analysis of Compound (1) Pattern 2

Form I Compound (1) was slurried in cumene at ambient conditions. The mixture was maturated at 50° C./room temperature heat-cool cycles (8 h cycle) for 70 h. The solids were filtered and analyzed by XRPD. Another XRPD analysis was taken after the solids were dried in a vacuum oven at about 35° C. for 24 hours. $^1$H-NMR analysis of the solids (Pattern 2) showed a cumene content of ~0.2 eq.

Example 2E

Preparation and Analysis of Compound (1) Pattern 5

Amorphous Compound (1) was slurried in water at ambient conditions. The mixture was maturated at 50° C./room temperature. heat-cool cycles (8 h cycle) for 70 h. The solids were filtered and analyzed by XRPD. Another XRPD analysis was taken after the solids were dried in a vacuum oven at about 35° C. for 24 hours. $^1$H-NMR analysis of the solids showed no residual solvent. GVS experiments showed a presence of a hydrate (Pattern 5) at about 50% relative humidity.

Example 2F

Preparation and Analysis of Compound (1) Form II

Pattern 5 Compound (1) was dehydrated by GVS to about below 40% relative humidity. XRPD analysis was performed on the non-solvated crystal to indicate Form II.

Example 2G

Preparation and Analysis of Compound (1) Form III

Pattern 5 Compound (1) was melted by heating the sample of the hydrate to about 200° C. at 10° C./min for about 5 min at the temperature endpoint. The sample was then allowed to cool down. $^1$H-NMR analysis was performed to confirm the chemical integrity of the sample had not been affected by the temperature. XRPD analysis was performed on the non-solvated crystal to indicate Form III.

Example 3

Pharmaceutical Compositions

Example 3A

Oral Composition

To prepare a pharmaceutical composition for oral delivery, a compound of Formula (1) was micronized to have a bulk density of about 0.20 g/mL and a tap density of about 0.31 g/mL. 90 mg of micronized compound was pack-filled into size "3" capsules suitable for oral administration.

Example 3B

Oral Composition

To prepare a pharmaceutical composition for oral delivery, a compound of Formula (1) was micronized to have a bulk density of about 0.20 g/mL and a tap density of about 0.31 ng/mL. 325 mg of micronized compound was pack-filled into size "00" capsules suitable for oral administration.

Example 3C

Oral Composition

To prepare a pharmaceutical composition for oral delivery, 90 mg of a compound of Formula (1) is mixed with 200 mg of lactose and 1% magnesium stearate. The mixture is blended and directly compressed into a tablet suitable for oral administration.

Example 3D

Parenteral Composition

To prepare a parenteral pharmaceutical composition suitable for administration by injection, 100 mg of a water-soluble salt of a compound of Formula (1) is dissolved in DMSO and then mixed with 10 mL of 0.9% sterile saline. The mixture is incorporated into a dosage unit form suitable for administration by injection.

Example 4

In Vitro Pharmacological Studies

Example 4A

Androgen Receptor Binding Assay

Androgen receptor competition binding was determined using labeled R1881 (an androgen agonist) in androgen sensitive human prostate cancer cell line (LNCaP) cells that express the mutated AR ($IC_{50}$ of 384 nM), and in cells that express the wild-type AR ($IC_{50}$ of 845 nM). FIG. 8 demonstrates that Compound (1) (described as compound 5) competed effectively with labeled R1881 for binding to both types of the AR in a dose-dependent manner.

Example 4B

Inhibition of Lyase Activity

Intact CYP17 expressed by transfected *E. coli* was isolated and purified as an enzyme source. Radiolabelled 17α-hydroxypregnenolone as the substrate. CYP17 activity was measured by the amount of tritiated acetic acid formed during the cleavage of the C-21 side chain of the substrate. FIG. 8 demonstrates that Compound (1) (described as compound 5) exhibited an IC50 value of 300.0 nM for CYP17.

Example 4C

Inhibition of Testosterone-Induced Proliferation of Prostate Cancer Cell Lines

Human prostate cancer cell lines (LNCaP and LAPC-4) were grown in culture and stimulated with 1 nM dihydrotestosterone (DHT). This concentration of DHT stimulated the proliferation of prostate cancer cells. The addition of Compound (1) elicited a dose-dependent inhibition of testosterone induced proliferation, in a fashion similar to Casodex®, which was used as a positive control in this experiment.

Example 4D

Degradation of Androgen Receptor (AR) Protein in Prostate Cancer Cell Lines

Figure 9:
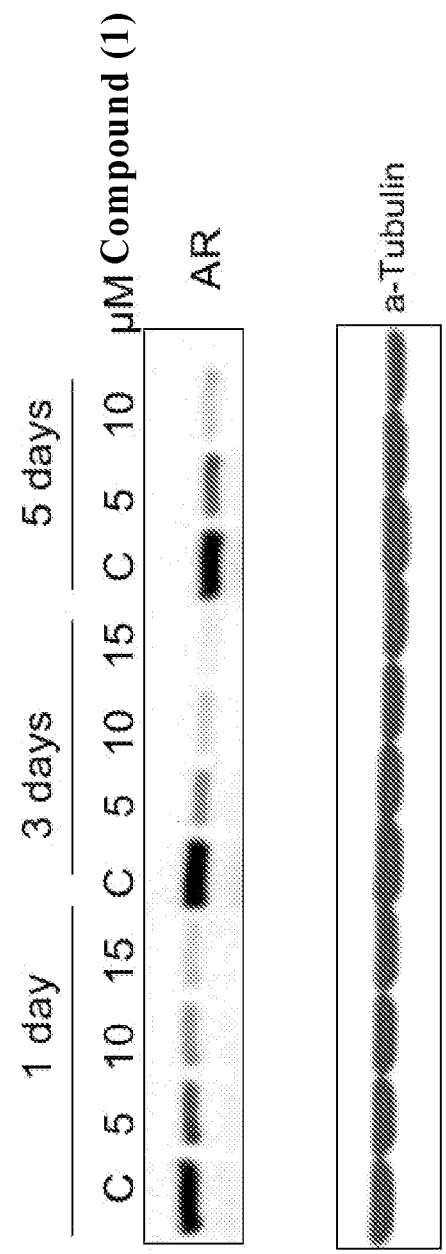
FIG. 9 is a western blot illustrating levels of androgen receptor protein.

Cycloheximide was added to human prostate cancer cell lines (LNCaP) to inhibit all protein synthesis in the cultured cells. Cycloheximide treatment alone reduced AR levels in a time-dependent fashion when protein extracts were probed with monoclonal antibodies directed against the AR protein. In FIG. 9, the addition of Compound (1) to these cultures resulted in a significantly greater rate of decrease of AR protein with time in culture.

Example 5

In Vivo Pharmacological Studies

Example 5A

Figure 10:
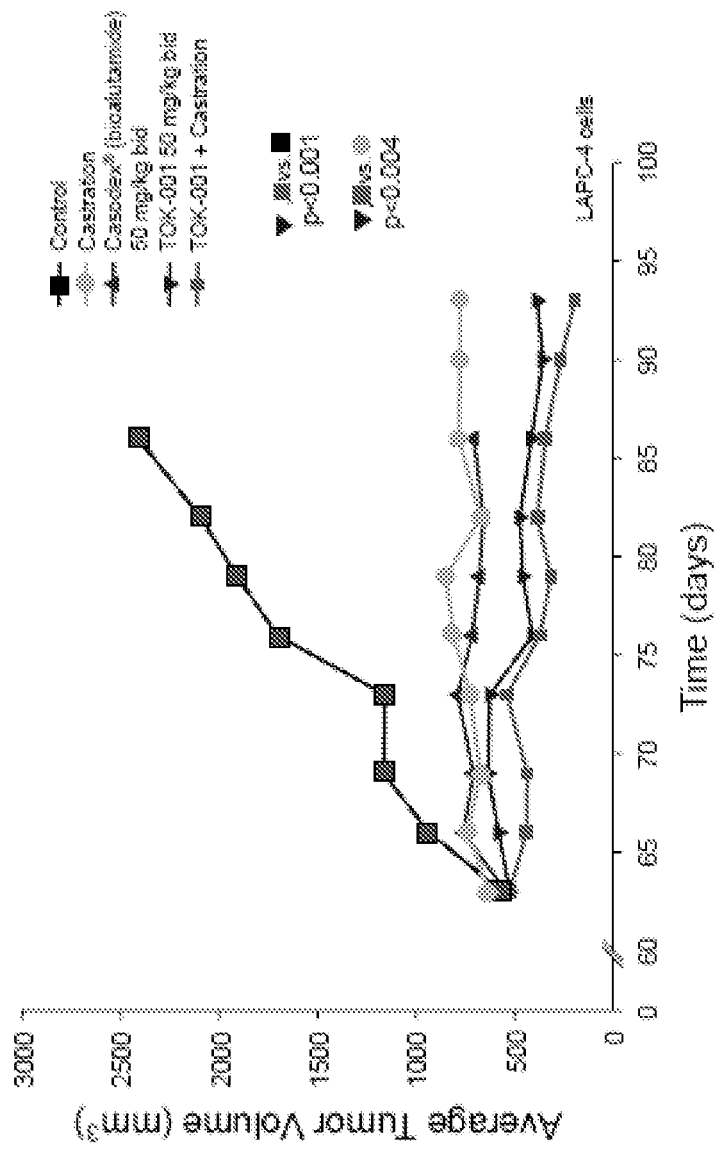
FIG. 10 is a line graph illustrating tumor xenograft sizes.

Inhibition of Growth of Human Prostate Cancer Xenografts in Severely Compromised Immunodeficient (SCID) Mice Xenografts of LAPC4 prostate cancer cell tumors were implanted in SCID mice. Tumor-bearing mice received twice daily subcutaneous (SC) administration of 50 mg/kg body weight (BW) Compound (1). Tumor size was measured weekly and compared with control mice that received vehicle, Casodex® or castration only. FIG. 10 shows that castration led to a significant reduction in final tumor volume as compared with control. Mice treated with Compound (1) showed a comparable or more pronounced decrease in tumor growth compared to castration.

Example 6

Use of Compound 1 to Treat Humans Suffering From Chemotherapy Naïve Castration Resistant Prostate Cancer Synopsis Name of Sponsor/Company: Tokai Pharmaceuticals, Inc.
Name of Investigational Product: Compound 1
Name of Active Ingredient: Compound 1
Title of Trial: Phase ½, Dose Escalation, Selected Dose Comparison Trial of Compound 1 for the Treatment of Chemotherapy Naive Castration Resistant Prostate Cancer
Study Acronym: ARMORI: Androgen Receptor Modulation Optimized For Response
Clinical Sites: Approximately five sites in the United States
Primary Investigators: Dr. Montgomery and          Phase of development: ½
Dr. Taplin
Trial Duration: Up to 117 days per subject
[including up to 28 days for screening and up to 89 days treatment (Phase 1 or 2)]
Objectives:

Phase 1
The objective of the Phase 1 stage is to find the dose(s) of TOK-001 that provides an acceptable safety profile. An acceptable safety profile is defined as a dose with a true dose limiting toxicity (DLT) rate of <35%.
Phase 2
The objectives of the Phase 2 stage are to: a. Assess biological signal for each of the dose(s) that are carried forward. b. Confirm an acceptable safety profile.
Methodology:

This trial is split into two stages: Phase 1 (dose escalation), followed by Phase 2 (selected dose comparison); for eligible subjects there is an optional Extension Phase following the completion of the Phase 1 and/or Phase 2 part of the trial. Screening takes place within 28 days of the first treatment visit. Subjects take Compound 1 once daily, with dinner, for 12 weeks. Trial visits occur bi-weekly (additional visits for safety laboratory tests occur in between the bi-weekly visits), and subjects return for the Trial Conclusion Visit at the end of the 12 week dosing period. Eligible subjects may then be permitted to enter an Extension Phase for continued therapy.
Phase 1
This is a dose escalation scheme, wherein three dose groups are enrolled with a target of up to six (no less than three) subjects per dose. Groups are treated with escalating doses (650, 1300, and 1950 mg Compound 1). Subsequent dose groups can be opened for enrollment (new subjects), provided criteria for escalation after the initial three subjects are met in the lower dose group. A true DLT rate of ≤35% is considered acceptable. The dose-finding rules are based on this, and the goal of the Phase 1 stage of the trial is to identify the highest dose that has an acceptable true DLT rate. A DLT is defined as any Grade 3 or higher adverse event (AE), considered to be possibly, probably, or definitely related to Compound 1. A Phase 1 data review is completed to select doses for Phase 2. Up to 12 weeks of data supporting safety and biological signal are utilized to select the dose(s) for the Phase 2.
Phase 2
Up to two doses are chosen for study in Phase 2. Twenty (20) new subjects are enrolled in each arm. If two arms are taken forward, subjects are randomized to the two arms (a maximum of 40 subjects). See the Statistical Methods section of this synopsis for a rationale for this sample -continued size. As within Phase 1, a DLT is defined as any Grade 3 or higher AE, considered to be possibly, probably, or definitely related to the Compound 1.
Extension Dosing
Extended dosing may be offered to subjects following completion of 12 weeks in the trial. Subjects must tolerate the Trial Drug and show no signs of progression to be eligible. Three months of extension dosing is available for eligible subjects.
Clinical Sites: Five sites in the United States
Number of subjects (planned): Approximately 50
Main criteria for inclusion:

1. Signed informed consent form (ICF) providing agreement to adhere to the dosing schedule, report for all trial visits and authorization, use, and release of health and research trial information.
2. Male age ≥18 years.
3. Histologically or cytologically confirmed adenocarcinoma of the prostate (excluding neuroendocrine differentiation or small cell histology).
4. Progressing disease in spite of androgen ablation therapy, defined as prostate specific antigen (PSA) levels which have risen on at least two successive occasions, at least 1 week apart, with the most recent PSA level ≥5 ng/mL.
5. Ongoing gonadal androgen deprivation therapy with gonadotropin-releasing hormone (GnRH) analogues or orchiectomy. Subjects who have not had an orchiectomy must be maintained on effective GnRH analogue therapy.
6. Eastern Cooperative Oncology Group (ECOG) Performance Status 0 or I.
7. Life expectancy of >12 weeks.
8. Able to swallow multiple capsules.

Main criteria for exclusions:

1. Participation in another clinical trial involving experimental therapy <4 weeks prior to enrollment.
2. Metastatic subjects with one or more of the following:
   a. Hepatic involvement
   b. Bone pain associated with confirmed radiological evidence of metastases that requires active pain management
   c. Non hepatic visceral metastases (excluding lung nodules and contiguous extra nodal disease, unless there is clear documented evidence of visceral metastases)
3. The following medications:
   d. Prior treatment with MDV3100, abiraterone, or TAK700
   e. Prior treatment with ketoconazole
   f. Prior treatment with chemotherapy
   g. Prior radiation therapy completed ≤4 weeks prior to enrollment
   h. Treatment with other therapies known to decrease PSA levels ≤4 weeks prior to enrollment [includes any dose of Megace ® (megestrol acetate), Proscar ® (finasteride), Propecia ® (finasteride), Avodart ® (dutasteride), Eulexin ® (flutamide), Casodex ® (bicalutamide), Nilandron ® (nilutamide), Aldactone ® (spironolactone), Cytadren ® (aminoglutethimide), estrogen, any herbal product known to decrease PSA levels (e.g., Saw Palmetto, etc), or any systemic corticosteroid (at Tokai Medical Advisor or designee and Medical Monitor discretion)]
   i. Treatment with anti-arrhythmia therapy for ventricular arrhythmia ≤4 weeks prior to enrollment
   j. Treatment with Coumadin ® (warfarin sodium) therapy ≤4 weeks prior to enrollment
   k. Treatment with Lasix ® (furosemide) or Zaroxolyn ® (metolazone) ≤1 week prior to enrollment
   l. Treatment with statins ≤1 week prior to enrollment [Note: Zetia ™ (ezetimibe) is not excluded]
   m. Treatment with tricyclic antidepressants (TCAs) ≤4 weeks prior to enrollment
4. The following laboratory findings:
   n. Testosterone >50 ng/dL
   o. Serum creatinine >1.5x the upper limit of normal (ULN)
   p. Bilirubin >1.5x ULN (Note: Subjects with elevated bilirubin due to Gilbert's syndrome are not excluded)
   q. Aspartate aminotransferase (AST) and/or alanine aminotransferase (ALT) >1.5x the ULN
   r. Hemoglobin ≤9.0 g/dL
   s. Absolute neutrophil count (ANC) ≤1.5 × $10^9$/L
   t. Platelets ≤100 × $10^9$/L
   u. Serum potassium ($K^+$) <3.5 mmol/L
5. The following medical conditions:
   v. New York Heart Association Class III or IV Congestive Heart Failure
   w. Myocardial infarction (within the 6 months prior to enrollment)
   x. Active angina pectoris
   y. History of Hepatitis B or Hepatitis C
   z. Known human immunodeficiency virus (HIV) infection
   aa. Uncontrolled hypertension (defined as systolic blood pressure >150 mmHg or diastolic blood pressure of >95 mmHg measured on at least two occasions)
   bb. History of adrenal insufficiency or hyperaldosteronism
   cc. History of apparent mineralocorticoid excess (AME) or history of black licorice hypersensitivity
   dd. Gastrointestinal disorders or gastric bypass surgery that could interfere with the absorption of Compound 1

-continued

| | | |
|---|---|---|
| | ee. | Serious active infections requiring systemic treatment or nonmalignant medical illnesses that are uncontrolled |
| | ff. | Any history of (in the past 5 years) second malignancy, other than treated non-melanoma skin cancer |
| | gg. | Active or uncontrolled autoimmune disease |
| | hh. | Active biliary disorders |
| 6. | | Any physical or mental condition, or social situation that in the opinion of the Investigator may interfere with the subject's ability to comply with the trial procedures. |
| 7. | | Men who are unwilling to use an adequate method of birth control if engaging in sexual contact with women of child bearing potential. |

Trial Drug, dosage and mode of administration:

Phase 1
The three initially targeted dose groups are:
 650 mg Compound 1.
1300 mg Compound 1.
1950 mg Compound 1.
Following reviews to be completed by an Internal Monitoring Committee (IMC), these dose groups may be modified by dose escalation or de-escalation to a higher or lower dose group, or to an intermediate dose.
Phase 2
Up to two dose groups are selected.
Extension Phase
During Phase 1, extension dosing continues at the assigned dose. During Phase 2, extension dosing occurs at the selected Phase 2 doses. Following Phase 2, extension dose(s) are determined after review of data from Phases 1 and 2. All doses are to be taken orally once daily with food. First dose to be taken with food between 10:00 and 14:00, at the clinical site; all subsequent doses to be taken between 17:00 and 21:00 with dinner.
Duration of treatment:

12 weeks, plus extension dosing for those subjects eligible.
Visit Schedule:

Both Phase 1 and Phase 2 include identical schedules for the primary 12 weeks in the trial:
Screening/Enrollment.
Onset of treatment.
Visits every 2 weeks, with off week blood labs.
Trial Conclusion Visit (at 12 weeks).
Note: Extension visit schedule is every 4 weeks.
Criteria for evaluation:

Safety
Incidence of AEs.
Change from baseline in the following additional safety parameters: clinical laboratory assessments, physical examination, vital signs, and 12-lead electrocardiograms (ECGs).
Treatment Compliance.
Efficacy
Percent of subjects with 50% or greater decrease in PSA from baseline to 12 weeks, or PSA nadir (whichever comes first).
Changes in computed tomography (CT)/magnetic resonance imaging (MRI) and bone scans.
Progression by Response Evaluation Criteria in Solid Tumors (RECIST).
Changes from baseline in additional special laboratories.
Changes from baseline in intratumoral androgen receptor (AR) protein, testosterone, and dihydrotestosterone (DHT) (in biopsy subset).
Time to Progression (TTP), Progression-Free Survival (PFS), and Overall Survival (OS)
Statistical methods:

Unless otherwise stated, all statistical tests are performed using 2-sided tests at the 5% significance level. Multiple comparison adjustments for multiple endpoints and visits are not performed at the final analysis because this is a Phase 1/2 trial; analyses are primarily descriptive in nature. Trial variables are summarized by descriptive statistics (N, mean, standard deviation, median, minimum, and maximum for continuous variables and frequency and percentage for categorical variables). The frequency of subjects experiencing any AEs by body system, relatedness, and severity are summarized in each treatment group using counts and percentages. Changes from baseline in clinical laboratory, ECG, and vital sign parameters are calculated by treatment groups and visits. The primary efficacy endpoint is the percent of subjects with 50% or greater decrease in PSA from baseline to 12 weeks, or PSA nadir (whichever comes first). Frequency and percentage are calculated for each treatment group. The primary analysis is also repeated using the Per Protocol Population. Overall response rate is calculated using RECIST by each treatment group. Changes from baseline in CT/MRI and bone scans, additional special laboratories, and intratumoral parameters (intratumoral AR protein, testosterone, and DHT) in the biopsy subset is calculated by treatment group and visit. TTP, PFS, and OS is considered Extension endpoints. Plasma concentration of Compound 1 at 0 hours ($C_{0hrs}$) and 4 hours ($C_{4hrs}$) on Day 1 and at available timepoints at subsequent visits are determined.

LIST OF ABBREVIATIONS AND DEFINITIONS OF TERMS

The abbreviations listed in Table 1 are used in this trial protocol.

TABLE 1

| Abbreviation | Definition |
| --- | --- |
| ADL | Activities of daily living |
| AE | Adverse event |
| ALT | Alanine aminotransferase |
| AME | Apparent mineralocorticoid excess |
| ANC | Absolute neutrophil count |
| AR | Androgen receptor |
| AST | Aspartate aminotransferase |
| AUC | Area under the curve |
| CBC | Complete blood count |
| CLIA | Clinical Laboratory Improvement Amendments |
| $C_{0\,hrs}$ | Plasma concentration at 0 hours |
| $C_{4\,hrs}$ | Plasma concentration at 4 hours |
| Cmax | Maximum concentration |
| COPD | Chronic obstructive pulmonary disease |
| CR | Complete response |
| CRPC | Castration resistant prostate cancer |
| CT | Computed tomography |
| CTCAE | Common Terminology Criteria for Adverse Events |
| CYP 17 | C17α-hydroxylase/C17,20-lyase |
| DHEA | Dehydroepiandrosterone |
| DHT | Dihydrotestosterone |
| DLT | Dose limiting toxicity |
| ECG | Electrocardiogram |
| ECOG | Eastern Cooperative Oncology Group |
| eCRF | Electronic case report form |
| EDTA | Ethylenediaminetetraacetic acid |
| FDA | Food and Drug Administration |
| GCP | Good Clinical Practice |
| GGT | Gamma glutamyl transferase |
| GnRH | Gonadotropin-releasing hormone |
| HDPE | High density polyethylene |
| HIV | Human immunodeficiency virus |
| HTRE | Hepatic toxicity related event |
| ICH | International Conference on Harmonization |
| ICF | Informed consent form |
| IEC | Independent Ethics Committee |
| IMC | Internal Monitoring Committee |
| IND | Investigational New Drug |
| IRB | Institutional Review Board |
| ITT | Intent-to-treat |
| IWRS | Interactive Web Response System |
| K2EDTA | Dipotassium ethylenediaminetetraacetic acid |
| LH | Luteinizing hormone |
| MCH | Mean corpuscular hemoglobin |
| MCV | Mean corpuscular volume |
| MedDRA | Medical Dictionary of Regulatory Activities |
| MOA | Mechanism of action |
| MRI | Magnetic resonance imaging |
| NE | Not evaluated |

TABLE 1-continued

| Abbreviation | Definition |
| --- | --- |
| NOAEL | No-observable-adverse-effect-level |
| ORR | Overall response rate |
| OS | Overall survival |
| PCF | Prostate Cancer Foundation |
| PD | Progressive disease (RECIST response criteria) |
| PFS | Progression-free survival |
| PI | Principal Investigator |
| PK | Pharmacokinetics |
| PP | Per protocol |
| PR | Partial response |
| PSA | Prostate specific antigen |
| RECIST | Response Evaluation Criteria in Solid Tumors |
| SAE | Serious adverse event |
| SAP | Statistical Analysis Plan |
| SCID | Severe combined immunodeficiency |
| SD | Standard deviation |
| SD | Stable disease (RECIST response criteria) |
| SDV | Source Data Verification |
| SoC | Standard of care |
| TCA | Tricyclic antidepressants |
| TEAE | Treatment-emergent adverse event |
| TMF | Trial Master File |
| TTP | Time to progression |
| ULN | Upper limit of normal |
| WHO | World Health Organization |

INTRODUCTION

1.1 Scientific and Clinical Rationale for Use of Compound 1 for Treatment of Castration Resistant Prostate Cancer 1.1.1 Castration Resistant Prostate Cancer Prostate cancer is the most common cancer in men. The majority of prostate cancer deaths are due to the development of metastatic disease that is unresponsive to conventional androgen deprivation therapy. Androgen deprivation therapy has been the standard of care in subjects with prostate cancer since the 1940s. Despite androgen deprivation, most subjects ultimately experience disease progression (Mohler et al., 2004; Scher et al., 2004). For many years this later phase of the disease was called "hormone insensitive prostate cancer" or "androgen independent prostate cancer." It has since become clear that the prostate cancer that emerges after years of androgen deprivation therapy remains dependent upon androgen. The prostate cancer cells that have survived have gained the ability to import low levels of circulating androgens (expressed from adrenal glands), become much more sensitive to these low levels of testosterone, and actually synthesize testosterone within the prostate cancer cell itself. This stage of prostate cancer is now termed "castration resistant prostate cancer" or CRPC.

1.1.2 Overview of Androgen and the Androgen Receptors Role in Prostate Cancer 1.1.2.1 Role of Androgens and the Androgen Receptor in Prostate Cancer Androgens play an important role in the growth of the normal prostate and in prostate carcinoma. Since almost all early prostate cancers are androgen dependent, androgen withdrawal initially produces responses in subjects with prostate cancer (Canil et al., 2005; Catalona, 1994; Chodak, 2004; Mohler et al., 2004; Pienta and Bradley, 2006). Androgen ablation therapy [either surgical or medical castration with a gonadotropin-releasing hormone (GnRH) agonist an androgen receptor (AR) antagonist] is the standard of care for most prostate cancer subjects. Clinical outcomes are similar, irrespective of the nature and timing of androgen ablation therapy. There is an initial response, followed by a period of stability which terminates in biochemical, radiographic and ultimately clinical progression (Bubley and Balk, 1996; Scher et al., 2004; Scher et al., 2008). It has become clear that one important survival mechanism established by the prostate cancer cell is a dramatic increase in its sensitivity to low levels of circulating and/or intracellular androgen. This is induced by androgen withdrawal. The increase in sensitivity to low levels of androgens is afforded by the increased expression of AR protein (Gregory et al., 2001; Taplin and Ho, 2001; Gelman, 2002; Litvinov et al., 2003; Lee and Chang 2003; Heinlin and Chang, 2004; Chen et al., 2004). According to the present invention, effective therapies for the treatment of prostate cancer should include complete androgen blockade.

1.1.2.2 Mechanism and Perturbation of Androgen Action

Androgens stimulate the growth of prostate tissue and prostate cancer cells by binding to a receptor that is present within the cytoplasm of androgen sensitive tissue. The receptor is bound to a carrier protein such as heat shock protein 90 (Pratt, 1993). Once bound, the hormone-receptor complex translocates to the nucleus and affects gene transcription. The AR is a ligand inducible hormone receptor of the nuclear receptor superfamily that plays a role in development and regulation of male secondary sex characteristics: these include the induction of spermatogenesis and the maintenance of bone and muscle mass and of androgen sensitive tissues (e.g., the prostate; Heinlein and Chang, 2004; Gelman, 2002). Agents that block the action (antiandrogens) of endogenous hormones (e.g., testosterone) are highly effective and routinely used for the treatment of prostate cancer (androgen ablation therapy). The first nonsteroidal antiandrogen, flutamide was approved for prostate cancer therapy in 1989 (Shahinian et al., 2006). Subsequently, other nonsteroidal ligands have been developed, mostly because this class of compounds react only with the AR. Recently, more specific, non-steroidal AR modulators that inhibit androgen actions have been developed and marketed [e.g., Casodex® (bicalutamide); Bohl et al., 2005].

1.1.2.3 Available Therapies for Androgen-Dependent Prostate Cancer

Other therapies have been developed to decrease the synthesis and secretion of endogenous testosterone from the testes. Reduction of circulating levels of androgen is accomplished through the administration of a GnRH receptor agonist, such as Lupron® (leuprolide), which gained Food and Drug Administration (FDA) approval for the current depot version in 1997. When given continuously, Lupron® decreases the synthesis and release of luteinizing hormone (LH) from the anterior pituitary gland. Under normal circumstances, LH travels in the systemic circulation to the testes where it stimulates the synthesis and release of testosterone. As a result of the down regulation of the pituitary LH induced by GnRH, circulating levels of testosterone fall (Catalona, 1994). Due to the reduction in circulating levels of testosterone, most androgen dependent prostate cancer cells stop cell division and die.

The combination of a GnRH receptor agonist and an antiandrogen is used not only to decrease the release of androgens from the testes, but also to block the ability of the remaining low levels of androgens to bind to the corresponding receptor in androgen sensitive tissue, such as the prostate gland.

1.1.2.4 Castration Resistant Prostate Cancer; Increased Androgen Receptor and Androgen While initially effective at suppressing tumor growth, these androgen ablation therapies eventually fail in almost all subjects, leading to CRPC (Mohler et al., 2004). As mentioned above, most, but not all, prostate cancer cells initially respond to androgen withdrawal therapy. However, with time, new populations of prostate cancer cells emerge that have responded to the selective pressure created by androgen ablation therapy and are refractory to it. Not only is the primary cancer refractory to available therapies, but cancer cells may also break away from the primary tumor and travel in the bloodstream, spreading the disease to distant sites (especially bone). Among other effects, this causes significant pain and extreme bone fragility (Stoch et al., 2001; Greenspan et al., 2005; Ye et al., 2007).

Although GnRH therapy may cause greater than a 90 to 95% reduction in the concentrations of circulating testosterone, concentrations of the steroid hormone within the prostate cells are reduced by only 50%. This still provides adequate amounts of androgen to continue the stimulation of the androgen sensitive tumor (Mizokami et al., 2004; Mohler et al., 2004; Titus et al., 2005; Page et al., 2006; Mostaghel et al., 2007).

1.1.3 Increases in Androgen Receptor in Castration Resistant Prostate Cancer

Previously, it had been assumed that prostate cancer cell growth in the presence of castrate levels of testosterone, as induced by therapy, was due to the emergence of a hormone independent prostate cancer cell type. However, it is now believed that the CRPC cells compensate for low levels of circulating testicular androgens induced by androgen ablation therapy by increasing the intracellular AR density. It has recently been shown that the number of ARs is increased in the prostate tumor tissue that has survived the initial therapy and has become castration resistant (Chen et al., 2004; Litvinov et al., 2003; Scher et al., 2004; Heinlein and Chang, 2004).

In this way, the prostate cancer cell is able to respond to much lower levels of circulating testosterone and continues to receive adequate androgen support in spite of the reduced amounts of circulating androgen.

1.1.4 Elevations in Intratumoral Androgens: The Adrenal Gland and an Intratumoral Source One source of low but still measurable amounts of circulating androgen in men treated with GnRH antagonists and androgen antagonists is the adrenal gland (Mizokami et al., 2004; Labrie et al., 2005). Adrenal androgen production is not affected by most therapies that reduce testicular testosterone production. Several studies have shown that the prostate cancer cell increases intracellular adrenal androgen content by improving its ability to efficiently import and process circulating adrenal androgens (Bubley and Balk 1996; Mizokami et al., 2004; Labrie et al., 2005; Stanbrough et al., 2006).

Modest inhibition of adrenal androgen biosynthesis has been achieved by the administration of ketoconazole, an antifungal agent that has been shown to be somewhat effective in the treatment of CRPC (Nakabayashi et al., 2006). However, ketoconazole has not been approved for use in the treatment of prostate cancer. The present invention encompasses the recognition that potent and specific compounds that inhibit androgen synthesis in the testes and adrenal tissues may be more effective for treatment of this stage of prostate cancer.

In addition to importing adrenal androgens, prostate cancer cells that survive after prolonged exposure to androgen ablation therapy also possess up-regulated levels of enzymes required for the intraprostatic synthesis of androgens (Nakamura et al., 2005; Stigliano et al., 2007; Holzbeierlein et al., 2004). An intracrine hypothesis has been suggested as a survival mechanism employed by the CRPC cell to assure uninterrupted androgenic support (Loberg 2005; Mostaghel et al., 2007). This concept has gained significant support within the community of scientists and clinicians who study prostate cancer. As a result, this concept has stimulated an increased demand for therapeutic compounds that inhibit androgen synthesis in all steroidogenic tissue (testes, adrenals and, in the case of CRPC, the prostate cancer cell itself).

CRPC cells survive in an environment characterized by low levels of circulating androgens by amplifying three different pathways to enhance the response to the intracellular androgens that remain available. These include:

Up regulation of the expression of the AR, which increases AR copy number and hence the sensitivity of the cells to low levels of circulating androgen induced by medical castration therapy.

Increase in the expression of enzymes involved in the importation and processing of adrenal androgens that remain in circulation after androgen deprivation therapy.

Increase in the expression of genes that regulate steroidogenesis, thereby permitting the CRPC cells to synthesize their own androgens.

New therapies are needed to address these changes that have occurred in subjects with CRPC.

1.1.4.1 Compound 1 as a Treatment for Castration Resistant Prostate Cancer

Given the emerging understanding of the survival mechanisms of CRPC cells, new therapies are needed. Compound 1 exhibits all of the necessary characteristics as it has been shown to:

Decrease androgen biosynthesis: Compound 1 inhibits the activity of cytochrome C17α-hydroxylase/$C_{17,20}$-lyase (CYP17), the enzyme that controls androgen production in the adrenals, testes, and prostate.

Decrease AR signaling: Compound 1 binds to the AR and is a competitive inhibitor of testosterone binding.

Decrease androgen sensitivity: Compound 1 reduces the content of AR protein within the prostate cancer cells and diminishes the ability of the cell to be sustained by low levels of androgenic growth signals.

The present invention provides therapeutic methods and compositions for the use of Compound 1 in the treatment of prostate cancer, and particularly of CRPC.

1.2 Risk-Benefit Assessment

This is a first-in-man trial of Compound 1 and potential toxic effects in humans are not yet fully known. Evaluation of the nonclinical data indicates that Compound 1 has the biological properties consistent with being a novel and potentially active agent in the treatment of CRPC. The data supports the proposed MOA and shows minimal toxicity in cell-based and animal models. The only safety signal seen, hepatoxicity, is a known adverse reaction that can be potentially induced by antiandrogens (Thole et al., 2004). An additional known class effect, apparent mineralocorticoid excess (AME), was not seen in nonclinical studies. This trial has been designed with the adverse nonclinical findings, theoretical MOA, and consideration of known class effect issues in mind. The trial evaluates potential clinical benefit and provides proof of concept while minimizing risk to subjects.

The present invention particularly provides dosing schemes that considers both safety and potential for biological activity. In one embodiment, an initial dose of 650 mg is utilized. This dose is 18-fold lower than the dose in dogs where the safety signal was seen and is expected to be potentially biologically effective in the inhibition of the lyase enzyme expressed in steroidogenic tissue, inhibition of binding of androgenic steroids to the AR, and destabilization of the AR protein in androgen responsive tissue. Further, at levels corresponding to human subcutaneous doses of 140, 280, and 560 mg a dramatic reduction was shown in the size of androgen dependent human prostate tumors in severe combined immunodeficiency (SCID) mouse models.

Investigational Plan

This example describes a Phase 1 and 2, open-label, dose escalation, dose comparison trial of Compound 1 for the treatment of chemotherapy naïve CRPC. The trial population includes males aged≥18 years, with confirmed adenocarcinoma of the prostate and progressing disease in spite of androgen ablation therapy, which is defined as prostate specific antigen (PSA) levels, which have risen on at least two successive occasions, at least 1 week apart, with the most recent PSA level≥5 ng/mL.

This trial is split into 2 stages: Phase 1 (dose escalation), followed by Phase 2 (selected dose comparison); there is an optional Extension Phase for eligible subjects, following the completion of the Phase 1 and/or Phase 2 stage of the trial.

Screening takes place within 28 days of the first treatment visit. Subjects take Trial Drug (Compound 1) once daily, with dinner, for 12 weeks. Trial visits occur every 2 weeks, and subjects return for the Trial Conclusion Visit at the end of the 12-week dosing period. Eligible subjects may then be permitted to enter an extension arm for continued therapy. Treatment may continue until disease progression, subject withdrawal, unacceptable toxicity, or at the Investigator's discretion.

For an individual subject, the maximum duration of the Phase 1 or 2 stage of the trial is up to 117 days [including up to 28 days for screening and up to 89 days treatment (Phase 1 or 2)]. The treatment window calculation includes the maximum window for the Trial Conclusion Visit (+5 days). Additional extension dosing may be provided to eligible subjects.

Figure 11:
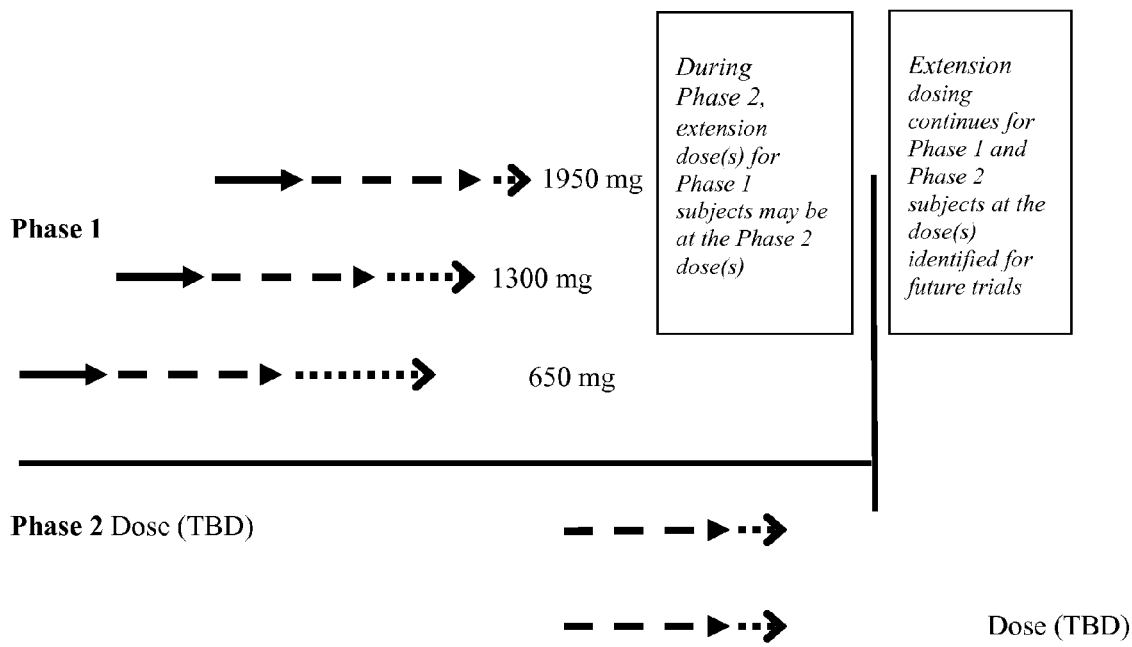
FIG. 11 graphically illustrates the process of the various phases of the clinical study described herein.

The details of each of these phases are described below and presented diagrammatically in FIG. 11. A data review of all Phase 1 data occurs to determine doses for subjects entering Phase 2. After the last subject in Phase 2 reaches 12 weeks, a data review of all trial data occurs to determine doses for future trials (and continued extension).

1.3 Phase 1 Design and Plan: Description

The objective of the Phase 1 stage is to find the dose(s) of Compound 1 that provides an acceptable safety profile. An acceptable safety profile is defined as a dose with a true DLT rate of ≤35%.

This is a dose escalation scheme where three dose groups are enrolled with a target of up to six (no less than three) subjects per dose. The targeted dose groups to be explored are 650 mg of Compound 1; 1300 mg Compound 1; and 1950 mg Compound 1.

Following reviews to be completed by an Internal Monitoring Committee (IMC), these dose groups may be modified by dose escalation or de-escalation to a higher or lower dose group, or to an intermediate dose. These modifications can occur only within the range of doses being explored.

TABLE 2

Identified Dose Groups and Available Dose Levels

| Identified Dose Groups | Available Dose Levels | Daily Dose | Dispensed As |
|---|---|---|---|
|   | −1 | 325 mg | 1 × 325 mg capsule |
| A | 0 (Starting Dose Level) | 650 mg | 2 × 325 mg capsule |
|   | +1 | 975 mg | 3 × 325 mg capsule |
| B | +2 | 1300 mg | 4 × 325 mg capsule |
|   | +3 | 1625 mg | 5 × 325 mg capsule |
| C | +4 | 1950 mg | 6 × 325 mg capsule |

Groups of subjects are treated with escalating doses, starting with 650 mg Compound 1. Subsequent dose groups can be opened for enrollment (new subjects), provided criteria for escalation after the initial three subjects are met in the lower dose group. A true DLT rate of ≤35% is considered acceptable. The dose-finding rules are based on this, and the goal of the Phase 1 stage of the trial is to identify the highest dose that has an acceptable true DLT rate. A DLT is defined as any Trial Drug related Grade 3 or higher adverse event (AE), considered to be possibly, probably, or definitely related to the Trial Drug.

Enrolled subjects in the Phase 1 stage who do not receive at least one dose of Trial Drug is replaced by an additional subject in the appropriate dose group. Similarly, if an enrolled subject is discovered to be ineligible, such a subject is replaced by an additional subject in the appropriate dose group.

1.3.1 Criteria for Escalation after the Initial Three Subjects

A review for DLTs in the initial three subjects in each dose group occurs once all three subjects have reached a minimum of 4 weeks of continuous dosing Real-time data are collected by electronic case report forms (eCRFs) and review includes all available data. Data are not required to be source verified to be included in this review. A DLT is defined as any Trial Drug related Grade 3 or higher AE, considered to be possibly, probably, or definitely related to the Trial Drug.

If, following the data review of the initial three subjects:
0/3 subjects experience DLTs, escalation to the next dose group can occur.
1/3 subjects experience DLTs, three additional subjects should be enrolled at this dose prior to escalation to the next dose group.
2/3 or 3/3 subjects experience DLTs, dosing is stopped at this dose group and Phase 1 dose de-escalation occurs.

Within the DLT review period any Grade 2 hepatic toxicity related event (HTRE) that is considered possibly, probably, or definitely related to the Trial Drug, can limit escalation to the next dose group to a maximum of 50%.

1.3.2 Criteria for Escalation when Expansion to the Full Six Subjects is Required If three additional subjects must be added to a dose group prior to escalation, review for DLTs in all six subjects occurs once the additional three have reached a minimum of 4 weeks of continuous dosing.

If, following expansion:
≤2/6 subjects experience DLTs, escalation to the next dose group can occur.
≤3/6 subjects experience DLTs, dosing is stopped at this dose group and Phase 1 dose de-escalation occurs.

1.3.3 Phase 1 Dose De-escalation

If de-escalation is required, subjects are de-escalated 1) to the next lower dose group or 2) if feasible, to a new intermediate dose between the dose at which the DLTs occurred and the next lower dose group. For example, if three or more subjects have DLTs in the 1300 mg group, subjects could be reassigned to a dose between 1300 mg and 650 mg. If de-escalation from the starting dose group (650 mg) is required, an additional group of three subjects can be enrolled at 325 mg.

If de-escalation occurs, escalation back to the dose from which de-escalation occurred may be considered following a review of the subjects enrolled at both doses.

1.3.4 Phase 1 Data Review

A Phase 1 data review is completed prior to initiation of Phase 2. Up to 12 weeks of data supporting safety and biological signal is utilized to select the dose(s) for the Phase 2. Only doses reviewed in Phase 1 and determined to have an acceptable DLT profile, or new doses below those with an acceptable DLT profile are considered for Phase 2 testing.

3.1.5 Dose Delay/Dose Modification

Subjects are monitored for toxicity, and the dose may be adjusted according to individual subject tolerance.

Dose reduction by 1 dose level may be required depending on the type and severity of toxicity encountered. The minimum dose is 325 mg daily. Dose reduction guidance is provided in Table 3.

Subjects completing 4 weeks of treatment with minimal treatment-related effects, as described in Table 2, may continue dosing at their assigned level per protocol.

TABLE 3

Dose Delay/Modifications for Toxicity Attributed to Trial Drug.

| Toxicity | Dose Delay/Modification | |
|---|---|---|
|   | Non-hematologic | Hematologic |
| Grade 0-1 | Continue at the same dose level. | Continue at the same dose level. |
| Grade 2 | Continue at the same dose level. | Continue at the same dose level. |
| Grade 3 | Withhold dose until toxicity is Grade 1 or has returned to subject's pre-event baseline, then resume treatment at the same dose level or reduce the dose by 1 level following discussion with Investigator, Medical Advisor, and Medical Monitor. | Withhold dose until toxicity is Grade 2 or has returned to subject's pre-event baseline, then resume treatment at the same dose level or reduce the dose by 1 level, following discussion with Investigator, Medical Advisor, and Medical Monitor. |
| Grade 4 | Withhold dose until toxicity is Grade 1 or has returned to subject's pre-event baseline, then reduce the dose by 1 level and resume treatment, or discontinue following discussion with | Withhold dose until toxicity is Grade 2 or has returned to subject's pre-event baseline, then reduce the dose by 1 level and resume treatment, or discontinue following discussion with |

TABLE 3-continued

Dose Delay/Modifications for Toxicity Attributed to Trial Drug.

| Toxicity | Dose Delay/Modification | |
|---|---|---|
| | Non-hematologic | Hematologic |
| | Investigator, Medical Advisor, and Medical Monitor. | Investigator, Medical Advisor, and Medical Monitor. |

Note:
Subjects who develop signs of AME may continue study treatment without interruption, as long as they respond to recommended AME treatment. If subjects are suspected to have AME, treatment with eplerenone, per label, and/or electrolyte repletion are recommended. Any other treatments for AME should be discussed with a Tokai Medical Advisor (or designee) and the Medical Monitor in advance when medically feasible.

The subject is discontinued from the study if the current dose is 325 mg and toxicity guidelines indicate a further dose reduction is necessary. Subjects requiring >4 weeks of dose interruption is considered for discontinuation from the study.

1.4 Phase 2 Design and Plan: Description

The objectives of Phase 2 are to assess biological signal and confirm an acceptable safety profile for each of the dose(s) that are carried forward. Stopping rules are in place so that enrollment to a particular dose is halted should reasonably convincing evidence exist to suggest that the true DLT rate exceeds 35%.

Twenty new subjects are enrolled in each arm taken forward from Phase 1. If two arms are taken forward, subjects are randomized to the two arms (a maximum of 40 subjects). See the Statistical Methods section for a rationale for this sample size.

As for Phase 1, a DLT is defined as any Trial Drug related Grade 3 or higher AE, considered to be possibly, probably, or definitely related to the Trial Drug.

As for Phase 1, only subjects who receive at least one dose of Trial Drug are considered in Phase 2. The proportion of subjects who do not receive at least one dose of Trial Drug and the reasons that the Trial Drug was not administered are recorded. This should occur at a very low frequency and that the reasons are normally administrative.

1.4.1 Phase 2 Dose Selection

Up to two doses are chosen for study in Phase 2. The Phase 1 data review is utilized as the basis for determining the dose(s). Selection of dose(s) is determined following IMC review of safety and biological effect data from Phase 1.

Possible scenarios that could lead to the exploration in Phase 2 of a single dose include the following:
If the observed DLT rate exceeds the 35% threshold at a dose in Phase 1, the dose group below which this occurred may be explored alone.
If all doses explored in Phase 1 show acceptable DLT profiles, the top dose explored in Phase 1, 1950 mg, may be explored alone.

Possible scenarios that could lead to the exploration of two doses in Phase 2 include the following:
If the observed DLT rate exceeds the 35% threshold in Phase 1, the dose group below which this occurred, and a lower dose may be selected. The lower dose may be the next lower dose or an intermediate dose between the dose below which the 35% DLT rate was exceeded and the next lower dose.
If all doses explored in Phase 1 show <35% DLT rate, the top dose explored in Phase 1, 1950 mg, and a second dose may be selected. The second dose may be the 1300 mg dose or an intermediate dose between 1950 mg and 1300 mg.

A high dose/low dose scenario may be considered if more than one dose explored in
Phase 1 shows <35% DLT rate.

1.4.2 Phase 2 Stopping Rules

Phase 2 data are reviewed for DLTs on an ongoing basis. Data are not required to be source verified to be included in this review.

If incidence of related DLTs exceeds 35%, then the IMC reviews the data and determine if revision to the dose needs to occur.

1.4.3 Phase 2 Dose Revision

If a dose is stopped in Phase 2, as per Phase 2 stopping rules, dosing of subjects is revised following a data review as follows:
If two doses were running in Phase 2, enrollment continues in the arm that was not stopped until 20 subjects are enrolled. If the arm stopped is the higher of the two dose groups, the IMC is called upon to recommend what dose should be used to proceed. Subjects in the arm of the trial that was stopped are treated at the continuing dose and complete their 12-week follow-up schedule.
If one dose was running in Phase 2, subsequent subjects should be dosed in (or switched to) 1) the next lower dose group seen in Phase 1 to have an acceptable DLT profile, or 2) if feasible, to a new intermediate dose between the dose where the DLTs occurred and the next lower dose seen in Phase 1 to have an acceptable DLT profile. This reduction in dosing takes place until 20 subjects have been enrolled at the lower dose. If stopping rules are met at this lower dose, no further dose reductions are made.

1.5 Extension Design and Plan: Description

Extended dosing may be offered to subjects following completion of 12 weeks in the Phase 1 or Phase 2 stage of the trial. Initial eligibility is determined at the 12 week visit on the basis of an acceptable risk/benefit ratio and the absence of signs of biochemical progression through Week 10 in the study. Continued eligibility is assessed throughout the Extension on the basis of a continued acceptable risk/benefit ratio and no signs of biochemical progression.

Acceptable risk/benefit ratio is determined by the Principal Investigator (PI) with confirmation by the Medical Monitor and/or Medical Advisor.

Biochemical progression is defined as per the Prostate Cancer Working Group 2 (Scher et al., 2008) as a) PSA increase ≥25% and ≥2 ng/mL above the nadir (if a decline from baseline occurs) or b) PSA increase ≥25% and ≥2 ng/mL from baseline (if no decline from baseline occurs).

Doses for extension are:
During Phase 1: Extension occurs at the assigned Phase 1 doses.
During Phase 2: Extension is at the dose(s) explored in Phase 2. Phase 1 subjects initially dosed at doses not used in Phase 2 are to be reassigned to a Phase 2 dose.
Following completion of Phase 2: Dose(s) are determined following review of data from Phases 1 and 2.

During the extension, subjects are followed for safety [by periodic review by the IMC of AEs, physical examinations, vital signs, 12-lead electrocardiograms (ECGs), clinical laboratory assessments], treatment compliance, and efficacy as shown by percent of subjects with 50% or greater decrease in PSA from baseline to 12 weeks, or PSA nadir (whichever comes first), changes in computed tomography (CT)/magnetic resonance imaging (MRI) and bone scans, progression by Response Evaluation Criteria in Solid Tumors (RECIST; v. 1.1), changes in special laboratories, and time to progression (TTP), progression-free survival (PFS), and overall survival (OS).

Treatment may continue until disease progression, subject withdrawal, unacceptable toxicity, or at the Investigator's discretion.

3.1.5 Internal Monitoring Committee

An external data safety monitoring committee is not established for this trial. A formally chartered in-house IMC including Investigators, the Medical Monitor, and the Medical Advisor are established. For the purpose of this protocol the in-house IMC reviews summary data collected in the serious adverse event (SAE) and clinical databases minimally, at the end of each 4-week period after the last subject in each dose group enrolls, and before starting a new dose level in Phase 1, and as needed in Phase 2. The IMC follows the guidance provided within the protocol, but retain the right to reassess reported DLTs, further expand dose groups, or dosing plans at their discretion. Findings of the meetings are documented in the project files and action taken as appropriate. Findings having immediate implication for the management of subjects in the trial are communicated to all PIs in the timeframe associated with unexpected and drug-related SAEs.

1.6 Endpoints

1.6.1 Phase 1 Endpoints
1.6.1.1 Primary Endpoints
Incidence of AEs.
Change from baseline in the following additional safety parameters: clinical laboratory assessments, physical examination, vital signs, and 12-lead ECG.

1.6.1.2 Secondary Endpoints
Percent of subjects with 50% or greater decrease in PSA from baseline to 12 weeks, or PSA nadir (whichever comes first).
Change from baseline in CT/MRI and bone scans.
Progression by RECIST criteria.
Changes from baseline in additional special laboratories.
Change from baseline in intratumoral AR protein, testosterone, and dihydrotestosterone (DHT) (in biopsy subset).

1.6.2 Phase 2 Endpoints
1.6.2.1 Primary Endpoints
Percent of subjects with 50% or greater decrease in PSA from baseline to 12 weeks, or PSA nadir (whichever comes first).

1.6.2.2 Secondary Endpoints
Incidence of AEs.
Change from baseline in the following additional safety parameters: clinical laboratory assessments, physical examination, vital signs, and 12-lead ECG.
Change from baseline in CT/MRI and bone scans.
Progression by RECIST criteria.
Changes from baseline in additional special laboratories.
Change from baseline in intratumoral AR protein, testosterone, and DHT (in biopsy subset).

1.6.3 Extension-specific Endpoints
Extension endpoints are as for Phase 2, with the addition of the following secondary endpoints: time to progression (TTP), progression-free survival (PFS), and overall survival (OS).

FIG. 12 (Table 5) describes the schedule of procedures used in the phases of the study. The following annotations correspond to FIG. 12.

ET: Early Termination; ICF: informed consent form; ECG: electrocardiogram; CT: computed tomography; MRI: magnetic resonance imaging; PCF: Prostate Cancer Foundation; PSA: prostate specific antigen; CBC: complete blood count; PSA: prostate specific antigen; AME: apparent mineralocorticoid excess; PK: pharmacokinetics.

1: Subjects are required to have CBC and chemistry run weekly during Phase 1 and 2. For those subjects not close enough to have this done in the laboratory at the clinical site, a local laboratory may be utilized for these off-week labs.

2: If this is the Early Termination visit, the Investigator must make every effort to perform the safety evaluations described for the Trial Conclusion visit.

3: Day 1 is the first dose of Trial Drug (to be taken with a meal between 10:00 and 14:00).

4: 12-lead ECG to be performed 0 hours (predose) and 4 hours (±15 mins) post dose (before PK sample).

5: For baseline, results of CT/MRI and bone scans used must be dated within 4 weeks of Day 1 [in an effort to avoid scans being repeated for the purpose of trial inclusion, exception can be granted by the Medical Monitor, in consultation with the Tokai Medical Advisor (or designee), regarding use of screening CT/MRI or bone scans for the inclusion to the next open dose outside of the 4-week window noted; For repeat, scans should occur at Phase 1 or 2 Conclusion Visit or at PSA nadir (whichever comes first). During extension dosing, CT/MRI and bone scans occur every 12 weeks. The use of MRI instead of CT scan is acceptable, provided that the same modality used at baseline is continuously employed for all later evaluations in the trial. Should unexpected events occur, and in the judgment of the treating physician it is in the subject's interest to have any other form of scan, this should be discussed with the Medical Monitor and Medical Advisor.

6: Biopsies for the assessment of androgen receptor protein, testosterone, and dihydrotestosterone is offered in a subset of subjects (PCF grant) under a separate institution generated ICF. Repeat biopsies should occur at Phase 1 or Phase 2 conclusion visit or at PSA nadir (whichever comes first).

7: If subjects are suspected to have AME, treatment with eplerenone, per label, and/or electrolyte repletion are recommended. Any other treatments for AME should be discussed with a Tokai medical representative and the Medical Monitor in advance when medically feasible.

8: If safety laboratory assessments are recorded >7 days before Day 1, they should be repeated and confirmed before dosing.

9: Safety laboratories only on off-week visits (no urinalysis).

10: Tests to be taken predose.

11: Only 11-deoxycortisol, corticosterone, cortisol, and testosterone are run. The following tests are not run: pregnenolone, 17α-hydroxyprogesterone, dehydroepiandrosterone, deoxycorticosterone, and androstenedione.

12: All Phase 1 and 2 subjects have PK draws on Day 1 at 0 hours (predose) and 4 hours (±15 mins) post dose (dosing to be between 10:00 and 14:00). At remaining visits: single PK samples are drawn with record of time since last dose (as calculated from the subject diary).

13: If continuing into the Extension.

14: Reporting begins at Screening.

| Laboratory Collection Details | | |
|---|---|---|
| Assessment | Volume | Type |
| Standard Clinical Labs | | |
| Serum Chemistry | 1.0 mL (3.0 mL whole blood) | Serum |
| Creatinine, glucose, triglycerides, urea, uric acid, bilirubin, cholesterol sodium, potassium, alkaline phosphatase, aspartate aminotransferase (AST), alanine aminotransferase (ALT), gamma glutamyl transferase (GGT), chloride, bicarbonate, total protein, albumin, direct and indirect bilirubin, calcium | | |
| CBC with differential | 2.0 mL | Whole Blood (EDTA) |
| Erythrocytes, mean corpuscular volume (MCV), mean corpuscular hemoglobin (MCH), neutrophils, eosinophils, basophils, lymphocytes, monocytes, platelets, leukocytes, hemoglobin, hematocrit | | |
| Urinalysis | 20 mL | Urine |
| pH, protein, glucose, ketone, bilirubin, blood, nitrite | | |
| Specialty Labs[1] | | |
| Pregnenolone | 0.5 mL | Serum |
| 17α-hydroxyprogesterone | 1.0 mL | Serum |
| Deoxycorticosterone | 3.0 mL | Serum/Plasma |
| 11-Deoxycortisol | 1.0 mL | Serum |
| Corticosterone | 1.0 mL | Serum |
| Cortisol | 1.0 mL | Serum |
| Dehydroepiandrosterone | 0.5 mL | Serum |
| Androstenedione | 1.0 mL (min 0.25) | Serum |
| Testosterone | 0.5 mL | Serum |
| Other Labs | | |
|  | 3.0 mL (draw) for 1 mL (plasma) | Plasma (K$_2$EDTA) |
| Prostate Specific Antigen | 1.0 mL | Serum |
| Intratumoral[2] Androgen receptor; Protein; Testosterone; Dihydrotestosterone | For participating sites only | Tissue |

CBC: complete blood count;
EDTA: ethylenediaminetetraacetic acid;
K$_2$EDTA: dipotassium ethylenediaminetetraacetic acid.
[1]To be run at central laboratory.
[2]Pharmacokinetics samples are collected in K$_2$EDTA tubes provided, put on ice immediately and centrifuged for plasma separation. Samples are frozen within 8 hours of plasma separation.
3: Done only in the subset of subjects who have biopsises completed with Prostate Cancer Foundation (PCF) grant.

2. Selection and Withdrawal of Subjects

The trial population consists of subjects with CRPC. To be eligible for this trial, subjects must be able to provide written consent and meet all the inclusion criteria and none of the exclusion criteria.

2.1 Subject Inclusion Criteria

Subjects must meet all of the following inclusion criteria prior to enrollment to be eligible for the trial:

1. Signed informed consent form (ICF) providing agreement to adhere to the dosing schedule, report for all trial visits and authorization, use, and release of health and research trial information.
2. Male age≥18 years.
3. Histologically or cytologically confirmed adenocarcinoma of the prostate (excluding neuroendocrine differentiation or small cell histology).
4. Progressing disease in spite of androgen ablation therapy, defined as PSA levels which have risen on at least two successive occasions, at least 1 week apart, with the most recent PSA level≥5 ng/mL.
5. Ongoing gonadal androgen deprivation therapy with GnRH analogues or orchiectomy. Subjects who have not had an orchiectomy must be maintained on effective GnRH analogue therapy.
6. Eastern Cooperative Oncology Group (ECOG) Performance Status 0 or 1.
7. Life expectancy of >12 weeks.
8. Able to swallow multiple capsules.

2.2 Subject Exclusion Criteria

Subjects who meet any of the following exclusion criteria prior to enrollment are not eligible to participate in the trial:

1. Participation in another clinical trial involving experimental therapy<4 weeks prior to enrollment.
2. Metastatic subjects with one or more of the following: 1) Hepatic involvement; and 2) Bone pain associated with confirmed radiological evidence of metastases that requires active pain management.
3. The following medications: 1) Prior treatment with MDV3100, abiraterone, or TAK-700; 2) Prior treatment with ketoconazole; 3) Prior treatment with chemotherapy; 4) Prior radiation therapy completed ≤4 weeks prior to enrollment; 5) Treatment with other therapies known to decrease PSA levels≤4 weeks prior to enrollment [includes any dose of Megace® (megestrol acetate), Proscar® (finasteride), Propecia® (finasteride), Avodart® (dutasteride), Eulexin® (flutamide), Casodex® (bicalutamide), Nilandron® (nilutamide), Aldactone® (spironolactone), Cytadren® (aminoglutethimide), estrogen, any herbal product known to decrease PSA levels (e.g., Saw Palmetto, etc), or any systemic corticosteroid (at Chief Medical Officer and Medical Monitor discretion)]; 6) Treatment with anti-arrhythmia therapy for ventricular arrhythmia≤4 weeks prior to enrollment; 7) Treatment with Coumadin® (warfarin sodium) therapy≤4 weeks prior to enrollment; 8) Treatment with Lasix® (furosemide) or Zaroxolyn® (metolazone)≤1 week prior to enrollment; 9) Treatment with statins≤1 week prior to enrollment [Note: Zetia™ (ezetimibe) is not excluded]; or 10) Treatment with tricyclic antidepressants (TCAs)≤4 weeks prior to enrollment.
4. The following laboratory findings: 1) Testosterone>50 ng/dL; 2) Serum creatinine>1.5× the upper limit of normal (ULN); 3) Bilirubin>1.5×ULN (Note: Subjects with elevated bilirubin due to Gilbert's syndrome are not excluded); 4) Aspartate aminotransferase (AST) and alanine aminotransferase (ALT)≥1.5× the ULN; 5)

Hemoglobin≤9.0 g/dL; 6) Absolute neutrophil count (ANC)≤1.5×109/L; 7) Platelets≤100×109/L; 8) Serum K$^+$<3.5 mmol/L.
5. The following medical conditions: 1) New York Heart Association Class III or IV Congestive Heart Failure; 2) Myocardial infarction (within the 6 months prior to enrollment); 3) Active angina pectoris; 4) History of Hepatitis B or Hepatitis C; 5) Known human immunodeficiency virus (HIV) infection; 6) hypertension (defined as systolic blood pressure>150 mmHg or diastolic blood pressure of >95 mmHg measured on at least two occasions) 7) History of adrenal insufficiency or hyperaldosteronism; 8) History of AME or history of black licorice hypersensitivity; 9) Gastrointestinal; 10) disorders or gastric bypass surgery that could interfere with the absorption of Compound 1; 11) Serious active infections requiring systemic treatment or nonmalignant medical illnesses that are uncontrolled; 12) Any history of (in the past 5 years) second malignancy, other than treated non-melanoma skin cancer; 13) Active or uncontrolled autoimmune disease; or 14) Active biliary disorders.
6. Any physical or mental condition, or social situation that in the opinion of the Investigator may interfere with the subject's ability to comply with the trial procedures.
7. Men who are unwilling to use an adequate method of birth control if engaging in sexual contact with women of child bearing potential.

2.3 Subject Withdrawal Criteria

Subjects may withdraw from the trial at any time without penalty and for any reason without prejudice to his future medical care.

Subjects must be withdrawn under the following circumstances:

The subject withdraws consent.

Additionally, subjects may be required to withdraw for the following reasons:

Adverse event(s) (AEs).

Disease progression as assessed by clinical, radiological, and tumor marker (PSA) progression.

If, in the opinion of the Investigator, the subject is no longer believed to be able to fulfill the requirements of the protocol.

Violation of eligibility criteria.

Deviation from the treatment plan specified in the protocol (e.g., incorrect administration of the Trial Drug, failure to attend trial visits).

In all cases, the primary reason for withdrawal must be recorded on the eCRF. If a subject is prematurely withdrawn (prior to the 12-week visit) for any reason, the Investigator must make every effort to perform the safety evaluations described for the Trial Conclusion Visit (12-week visit).

2.4 Premature Termination of the Trial

If the Investigator or the Medical Monitor becomes aware of conditions or events that suggest a possible hazard to subjects if the trial continues, the trial may be terminated after appropriate consultation between the relevant parties.

Conditions that may warrant termination include, but are not limited to the discovery of an unexpected, significant, or unacceptable risk to the subjects enrolled in the trial or failure to enroll subjects at an acceptable rate.

3. Treatment of Subjects 3.1 Description of Trial Drug

Trial Drug for Phase 1 consists of Compound 1 at three dose groups: (1) 650 mg Compound 1 (two 325 mg capsules); (2) 1300 mg Compound 1 (four 325 mg capsules); (3) 1950 mg Compound 1 (six 325 mg capsules). Additional interim doses may be explored.

Dose(s) for Phase 2 are determined based on results obtained in Phase 1, but can be expected to include one or two of the doses explored in Phase 1.

Doses for extension are determined based on results obtained in Phases 1 and 2.

On the first day of dosing (Day 1), subjects are required to take Trial Drug orally with a meal (between 10:00 and 14:00). Subjects are given a supply of Trial Drug at this visit and at visits every 2 weeks (starting at Day 8; Visit 3), and are instructed to take Trial Drug orally, once daily with dinner (between 17:00 and 21:00) from Day 2 onwards. Subjects take Trial Drug for 12 weeks in Phase 1 and 2. Subjects who tolerate Trial Drug and show no signs of progression may be eligible for continued dosing in the extension arm of the trial. The duration of dosing in the extension arm is at least 12 weeks.

Trial Drug is dispensed at enrollment and every 2 weeks during the initial 12 weeks (Visits 2, 4, 6, 8, 10, and 12), then every 4 weeks starting with the Trial Conclusion Visit (if continuing into the extension).

3.2 Concomitant Medications

Subjects should not receive unapproved concomitant treatment on entry to the trial, nor should treatments for CRPC other than the Compound 1 be given during the trial. Subjects who have not had an orchiectomy must be maintained on effective GnRH analogue therapy.

If the administration of any concomitant treatment is deemed necessary by the PI, it must be reported in the eCRF and in the subject's medical records.

All additional treatments taken by the subjects upon entry to the trial or at any time during the trial are regarded as concomitant medications and must be documented in the eCRF.

The following information must be recorded in the eCRF for each concomitant medication: generic name, route of administration, start date, stop date, dosage, and indication. Any changes in the dosage or regimen of a concomitant medication must be recorded in the eCRF.

At the Screening Visit, subjects are asked what medications they have taken during the last 30 days. At each subsequent trial visit, subjects are asked what concomitant medications they are currently taking. Prohibited concomitant medications include: Megace® (megestrol acetate); Proscar® (finasteride); Propecia® (finasteride); Avodart® (dutasteride); Eulexin® (flutamide); Casodex® (bicalutamide); Nilandron® (nilutamide); Aldactone® (spironolactone); Cytadren® (aminoglutethimide); Estrogens; Any herbal product known to decrease PSA levels (e.g., Saw Palmetto and PC-SPES etc.); Any systemic corticosteroid; Coumadin® (warfarin sodium); Lasix® (furosemide) and other potassium depleting diuretics; Zaroxolyn® (metolazone); Statins [Note: Zetia (ezetimibe) is not excluded]; Any anti-arrhythmic drugs for ventricular arrhythmia; and TCAs.

All other prescription and non-prescription medications, including non-narcotic and narcotic analgesics, may be used as appropriate. All concomitant medication usage shall be verbally assessed at each study visit and recorded in the eCRFs.

Note: regarding systemic corticosteroids: if a subject with moderate chronic obstructive pulmonary disease (COPD), controlled asthma, or other chronic condition requiring steroids meets the enrollment criteria, but they need short time pulsed medium dose steroids during the study (e.g., during a COPD exacerbation etc.), this can be acceptable with approval by the Medical Monitor responsible for the trial.

3.3 Treatment Compliance

Subjects are instructed to return any unused supplies at each subsequent visit. At each visit, the subject is questioned regarding treatment compliance and the returned pills are counted and documented to verify subject compliance and drug accountability.

Diary cards are dispensed at the Screening Visit, and every 2 weeks thereafter (every 4 weeks during the Extension Phase); completed cards are collected throughout the trial. Subjects record the time of dosing and number of pills taken each day on their diary cards to allow monitoring of drug accountability and treatment compliance.

If dosing compliance is not maintained at between 80 and 120%, the subject may be withdrawn from the trial. Subjects are instructed that any missed doses are not rescheduled.

3.4 Randomization and Blinding

Randomization is used for assignment to dose groups in Phase 2. There is no blinding of Trial Drug; assignment is known to the subjects and Investigators. For the randomization of subjects in Phase 2 (if more than 1 dose group explored), the Investigator uses an Interactive Web Response System (IWRS). The IWRS assigns subjects to a dose group based on a pre-defined randomization list. Further details can be found in the Trial Master File (TMF).

4. Trial Drug Materials and Management

4.1 Trial Drug

4.1.1 Quantitative Composition

Compound 1 is a 17-heteroaryl substituted semi-synthetic steroid. The A, B, and C rings are structurally-analogous to those of dehydroepiandrosterone (DHEA) and pregnenolone. The Compound 1 benzimidazole functionality is appended via a sp2 carbon (A-16, 17 olefin) to the D-ring.

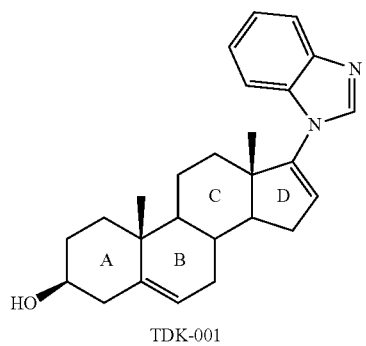

TDK-001

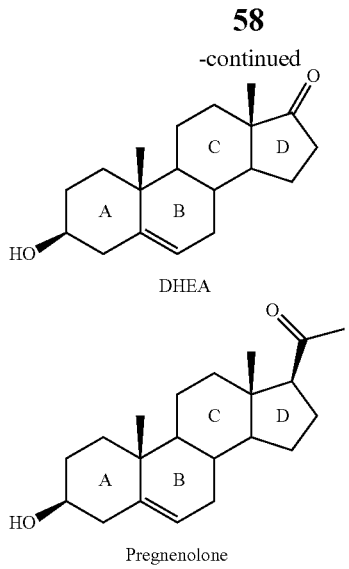

DHEA

Pregnenolone

4.1.2 Dose Selection

To predict a safe and potentially therapeutic range of doses for this trial the following information was considered: CYP17 inhibition; Receptor binding data; Concentration of AR protein in target tissue; Accumulation in tumor tissue; and Animal safety, efficacy, pharmacokinetic (PK), and toxicokinetic data.

Evaluation of all of the nonclinical data shows that Compound 1 has biological properties consistent with those required to treat CRPC. For example, this drug possesses biological activity in biochemical, cell based, and animal models of prostate cancer. In vitro safety testing has shown that Compound 1 does not have genotoxicity, does not interfere with the activity of cytochrome P450 systems known to metabolize many drugs, and interacts with off-target receptors only at high micromolar concentrations. The compound is orally bioavailable and, when administered chronically to rats, fails to elicit toxic responses. At doses below 300 mg/kg in dogs, Compound 1 has been shown to have no toxic effects. Similar maximal blood levels of drug were achieved in the rat and dog models when doses were administered on a mg/kg body weight basis.

At the no-observable-adverse-effect-level (NOAEL) in dogs (150 mg/kg) the exposure to Compound 1 [maximum concentration (Cmax) and area under the curve (AUC)] was calculated and similar exposure indices were predicted at the starting dose in humans (9 mg/kg for 70 kg man). On an AUC basis the human starting dose is predicted to be 16 times lower than the NOAEL dose in dogs.

Consolidation of the results of these studies supports the selection of the first-in-man trial dose of 650 mg/day. This dose is 18-fold lower than the dose in dogs where the safety signal was seen and is expected to be potentially biologically effective in the inhibition of the lyase enzyme expressed in steroidogenic tissue, inhibition of binding of androgenic steroids to the AR, and destabilization of the AR protein in androgen responsive tissue. Further, at levels corresponding to human subcutaneous doses of 140, 280, and 560 mg a dramatic reduction was shown in the size of androgen dependent human prostate tumors in SCID mouse models.

4.2 Trial Drug Supply

Drug product is a micronized powder-in-capsule. Composition of the drug product consists of micronized Compound 1 and size "00" Capsugel Coni-Snap® Capsules. In some embodiments, a capsule contains 325 mg of the compound.

4.3 Trial Drug Packaging and Labeling

Drug product is bulk packaged in 950-cc white opaque high density polyethylene (HDPE) tamper-evident foil sealed round jars and shipped to each clinical site pharmacy. The 325 mg, size "00" capsules are packaged 400 per bottle. For clinical use, the clinical site pharmacy repackages and dispenses capsules into HDPE bottles for individual subject use that are labeled with the following information: Subject Identification; Compound 1 New Drug for Investigational Use Only; Manufacture date and lot number; Clinical Site; Contact Number.

4.4 Trial Drug Storage

Trial Drug should be stored at ambient temperatures (15-30° C. (59-86° F.)), protected from high heat and humidity using standard control heating, ventilation, and air conditioning (HVAC) systems.

4.5 Randomization

If two doses are carried forward into Phase 2, a 1:1 randomization schedule is prepared.

4.6 Administration

Trial Drug is taken orally and should be taken with a meal. The first dose of Trial Drug is administered by the subject in the clinical site, between 10:00 and 14:00. Receipt of the first dose (Day 1) is considered enrollment. Subjects then receive Trial Drug from the pharmacy consistent with the labeling requirements detailed above, and are to take their dose daily, between 17:00 and 21:00. Subjects are instructed that any missed doses are not rescheduled. Trial Drug is dispensed at enrollment and every 2 weeks during the initial 12 weeks (Visits 2, 4, 6, 8, 10, and 12), then every 4 weeks starting with the Trial Conclusion Visit (if continuing into the extension).
3.1.5 Pharmacy Accountability Upon receipt of Trial Drug, an inventory must be performed and the Accountability Log filled out and signed by a designated staff member. It is important that the designated staff member counts and verifies that the shipment contains all the items noted in the shipment inventory. Any missing, damaged, or unusable Trial Drug in a given shipment must be documented. Furthermore, the PI and/or responsible site personnel must notify Pharm-Olam of issues noted during accountability of the shipment. In addition to the time of a receipt of a shipment, the Accountability Log must be completed each time drug is dispensed to a subject.
8.3.2 Trial Drug Handling and Disposal The Investigator is responsible for maintaining accurate Trial Drug accountability records throughout the trial. Each dispensing of Trial Drug is documented in the eCRF. All unused Trial Drug dispensed by the site pharmacy must be returned to the clinical site, and destroyed in an appropriate manner according to the standard practice at each clinical site. This includes Trial Drug bottles—both empty bottles and bottles containing unused Trial Drug. Destruction of such supplies is documented in the Accountability Log and a representative verifies disposition records.

5. Assessment of Efficacy

Disease progression and biological signals are explored in the present study, as detailed in this section.

5.1 Disease Progression

Disease progression is evaluated by conducting the following assessments.
5.1.1 Clinical Assessments Clinical assessments with regard to disease progression (e.g., pain) are presented as safety data.
5.1.2 Biomarkers
5.1.2.1 Prostate Specific Antigen Prostate specific antigen is determined in accordance with the Schedule of Procedures.
5.1.3 Radiological Assessments
5.1.3.1 Response Evaluation Criteria in Solid Tumors (RECIST)

The Response Evaluation Criteria in Solid Tumors (RECIST) are unified, easily applicable criteria for measuring tumor response using X-ray, CT, and magnetic resonance imaging (MRI). The technique is recommended for National Cancer Institute (NCI)-sponsored trials and involves formalized rules for measurement of tumor target lesions. RECIST criteria are a voluntary, international standard, and are not an NCI standard. They are based on a simplification of former methods [World Health Organization (WHO), ECOG] and based on measurable disease, (i.e., the presence of at least one measurable lesion). RECIST criteria offer a simplified, conservative, extraction of imaging data for wide application in clinical trials. RECIST (Eisenhauer et al., 2009, incorporated by reference herein) is used in this trial.
5.1.3.2 MRI and Bone Scan CT/MRI and bone scans are expected to be done as part of the standard of care, and are performed in accordance with the Schedule of Procedures (Table 5). The use of MRI instead of CT scans is acceptable, provided that the same modality used at baseline is continuously employed for all later evaluations in the trial. Should unexpected events occur, and in the judgment of the treating physician it is in the subject's interest to have any other form of scan, this should be discussed with the Medical Monitor and Medical Advisor.

In an effort to avoid scans being repeated for the purpose of trial inclusion, exception can be granted by the Medical Monitor (in consultation with the Tokai Medical Advisor or designee) regarding use of screening scans (CT/MRI or bone) for the inclusion to the next open dose outside of the 4-week window noted. However, this exception is based on the following criteria: The subject must have missed recruitment in a previous Phase 1 dose due to competitive screening; All other screening tests must be repeated and must confirm the subject remains eligible; No scans are accepted beyond 6 weeks prior to the first dose of Trial Drug; and Statement must be received that, in the PI's medical opinion, the subject is not suspected to have radiological progression and there are no clinical indications for repeat scan.

Allowance of this exception lessens unnecessary risk to the subject of repeating scans at an increased frequency above standard of care (every 3 to 6 months).
5.1.3.3 Time to Progression (TTP), Progression-Free Survival (PFS) and Overall Survival (OS).

Subjects are followed throughout the trial for the capture of survival data.

5.2 Special Laboratories

Special laboratories are determined in accordance with the Schedule of Procedures (Table 5).

Special laboratories include the following: pregnenolone, 17-hydroxyprogesterone, deoxycorticosterone, 11-deoxycortisol, corticosterone, cortisol, DHEA, androstenedione, and testosterone.

5.3 Intratumoral AR Protein, Testosterone and Dihydrotestosterone

Biopsies for the analysis of intratumoral parameters (AR protein, testosterone, and DHT) are offered in a subset of subjects under a separate institution generated ICF. Repeat biopsies should occur at the Phase 1 or 2 Trial Conclusion Visit or at PSA nadir (whichever comes first).

5.4 Intratumoral parameters are determined in accordance with the Schedule of Procedures. Concentration of Compound 1

PK samples are collected in accordance with the Schedule of Procedures (Table 5).

Samples are collected in dipotassium ethylenediaminetetraacetic acid (K2EDTA) tubes provided, put on ice immediately, and centrifuged for plasma separation. Samples are frozen within 8 hours of plasma separation.

6. Assessment of Safety

6.1 Safety Parameters 6.1.1 Laboratory Parameters

Central laboratory: Laboratory assessments are performed by a central laboratory, as identified in the Contact List.

Local laboratories: Laboratory assessments are performed locally at each site's laboratory by means of their established methods.

Refer to the Clinical Laboratory Improvement Amendments (CLIA) for further details.

The safety laboratory parameters are determined in accordance with the Schedule of Procedures and the instructions set out in the laboratory manual.

Laboratory abnormalities are recorded at the judgment of the Investigator as either clinically significant or not clinically significant.

6.1.2 Vital Signs

The following vital signs are assessed in accordance with the Schedule of Procedures: Blood pressure (systolic and diastolic; mmHg); Heart rate (beats per minute); Body temperature (° C.), oral; Respiration rate (breaths per minute); Weight; and Height (baseline only). Vital signs are taken when the subject has been sitting down for at least 10 minutes.

6.1.3 Electrocardiograms

Twelve-lead ECGs are performed in accordance with the Schedule of Procedures. All 12-lead ECGs are conducted after the subject has been supine for 3 minutes. The 12-lead ECG monitors are calibrated and standardized according to the clinical site's standard operating procedures. All clinically-significant ECGs (except for pre-existing abnormalities) are reviewed by a cardiologist.

6.1.4 Physical Examinations

Physical examinations are performed in accordance with the Schedule of Procedures. The physical examination includes the following body systems: general appearance, HEENT (head, ears, eyes, nose, and throat), respiratory, abdomen, renal (urological), genitalia, musculoskeletal, neurological, lymph nodes, skin, and other. ECOG performance status is recorded. The ECOG scales and criteria are used by doctors and researchers to assess how a subject's disease is progressing, assess how the disease affects the daily living abilities of the subject, and determine appropriate treatment and prognosis.

TABLE 1

| | ECOG Performance Status |
|---|---|
| Grade | ECOG |
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all self-care but unable to carry out any work activities. Up and about more than 50% of waking hours |
| 3 | Capable of only limited self-care, confined to bed or chair more than 50% of waking hours |
| 4 | Completely disabled. Cannot carry on any self-care. Totally confined to bed or chair |
| 5 | Dead |

6.1.5 Adverse Events (AE)

An Adverse Event (AE) is any untoward medical event that occurs in a subject who has received an investigational product, and does not necessarily have a causal relationship with this treatment. An AE can therefore be any unfavorable and unintended sign (including abnormal laboratory finding), symptom, or disease temporally associated with the use of an investigational product, whether or not related to the product. All AEs recorded during the course of the clinical trial are coded according to the Medical Dictionary of Regulatory Activities (MedDRA) system and assigned to a system organ class.

A treatment-emergent AE (TEAE) is defined as an AE that begins or that worsens in severity and/or frequency, or changes in nature after at least one dose of Trial Drug has been administered. All AEs, including intercurrent illnesses, occurring during the trial are documented in the eCRF. Concomitant illnesses, which existed prior to entry into the trial, is not considered AEs unless they worsen during the treatment period. Pre-existing conditions are recorded in the eCRF.

A DLT is defined as any Trial Drug related Grade 3 or higher AE, considered to be possibly, probably, or definitely related to the Trial Drug. It is possible that an AE can be considered a DLT even though it is not deemed as serious.

6.2 Relationship to Trial Drug

6.2.1 Assessment of Adverse Event

Each AE is assessed by the Investigator with regard to the following categories.

6.2.1.1 Seriousness

A serious AE (SAE) is defined as any untoward medical occurrence that at any dose: results in death; or is life-threatening. Classification as an AE requires that the subject is at immediate risk of death at the time of the event; it does not mean that the event hypothetically might have caused death if it were more severe. An AE is additionally characterized by one or more of: requiring or prolonging subject hospitalization; resulting in persistent or significant disability or incapacity; being a congenital anomaly or birth defect; being an important medical event(s) that may not be immediately life-threatening or result in death or hospitalization but that may jeopardize the subject or require intervention to prevent one of the above outcomes.

Medical and scientific judgment are exercised in deciding whether a case is serious and whether expedited reporting of the event to Institutional Review Boards (IRBs) and regulatory agencies is appropriate.

6.2.1.2 Severity

The severity of each AE must be assessed by the Investigator using the NCI Common Terminology Criteria for AEs (CTCAE) v4.0, and recorded in the eCRF.

The severity of an AE is graded according to the following clinical descriptions:

- Grade 1: Mild; asymptomatic or mild symptoms; clinical or diagnostic observations only; intervention not indicated;
- Grade 2: Moderate; minimal, local or noninvasive intervention indicated; limiting age-appropriate instrumental activities of daily living (ADL)*;
- Grade 3: Severe or medically significant but not immediately life-threatening; hospitalization or prolongation of hospitalization indicated; disabling; limiting self care ADL**;
- Grade 4: Life-threatening consequences; urgent intervention indicated; and
- Grade 5: Death related to AE.

* Instrumental ADL refers to preparing meals, shopping for groceries or clothes, using the telephone, managing money, etc.
  ** Self care ADL refers to bathing, dressing and undressing, feeding self, using the toilet, taking medications, and not bedridden.

6.2.1.3 Causality

The Investigator assesses the causality/relationship between the Trial Drug and the AE and records that assessment in the eCRF. Causality is shown as: definitely related; probably related; possibly related; unlikely related; or not related.

6.3 Recording Adverse Events

Adverse event reporting extends from Screening until 30 days after the last dose of Trial Drug or until the event has resolved/stabilized. Adverse events occurring after the end of the trial are reported if the Investigator considers there is a causal relationship with the Trial Drug.

All AEs, regardless of the relationship to Trial Drug, are recorded in the eCRF.

All AE reports contain a brief description of the event, date and time of onset, date and time of resolution, intensity, treatment required, relationship to Trial Drug, action taken with the Trial Drug, outcome, and whether the event is classified as serious.

6.3.1 Follow-Up of Adverse Events

All AEs experienced by a subject, irrespective of the suspected causality, are monitored until the event has resolved/stabilized, any abnormal laboratory values have returned to baseline or stabilized at a level acceptable to the Investigator and Medical Monitor, until there is a satisfactory explanation for the changes observed, or until the subject is lost to follow-up.

8.3.2 Reporting Adverse Events

The Investigator reports any SAEs to the Pharm-Olam Pharmacovigilance Unit within 24 hours of discovering the event. When calling to report an SAE, an SAE term, the Investigator's name, the reporter's name, the telephone number where the reporter can be reached, and the protocol number and title are given. Any SAE occurring within 30 days after the final dose and considered to be at least possibly related to the Trial Drug, and therefore a possible adverse drug reaction, is reported. Based on the assessment of the event, a decision is made concerning the need for further action including regulatory reporting.

7. Observations by Visit

Visits during the treatment period occur within ±3 days of the scheduled visit. If a subject misses a visit they do not make up that visit but attend the next regularly scheduled visit. All times are recorded using the 24 hour clock (e.g., 23:20, not 11:20 pm).

7.1 Screening (Visit 1)

The Screening Visit occurs within 28 days of the first dose (Day 1). At Screening, the following assessments are performed and measurements recorded: Obtain written informed consent (signed ICF); Verify eligibility criteria; Record medical/oncological history; Demographic details; Physical examination; Vital signs; 12-lead ECG; CT/MRI and bone scans—results of CT/MRI and bone scans used must be dated within 4 weeks of Day 1; Biopsy (a subset of subjects; covered by a separate ICF); Laboratory safety tests (hematology, serum chemistry, urinalysis)—if safety laboratory assessments are recorded>7 days before Day 1, they should be repeated and confirmed before dosing; Record concomitant medications. AEs are recorded from this visit.

7.2 Enrollment (Visit 2)

At the Enrollment Visit (Day 1, Visit 2), the following assessments are performed and measurements recorded: 12-lead ECG (predose); Special laboratory tests; PSA; PK sample (predose); Concomitant medications; AEs.

Trial Drug is administered at the clinical site, with food, between 10:00 and 14:00. 12-lead ECG is performed 4 hours (±15 mins) post dose (before PK sample). PK sample is collected 4 hours (±15 mins) post dose (after ECG). Trial Drug is dispensed and subjects are trained on the use of Trial Drug. Compliance diary is issued and subjects are trained on its use. Subjects are required to continue treatment once daily with dinner (between 17:00 and 21:00) from Day 2 until the next visit.

7.3 Off-Week Visits (Visits 3, 5, 7, 9, and 11)

Subjects return to the clinical site on Day 8 (±3 days), 1 week after Visit 2, and every 2 weeks thereafter for off-week laboratory tests. For those subjects geographically distant from the clinical site, a local laboratory may be utilized. At these visits laboratory safety tests (hematology and serum chemistry only) are performed.

7.4 Bi-Weekly Visits Every 2 Weeks (Visits 4, 6, 8, and 10)

Subjects return to the clinical site on Day 15 (±3 days), 1 week after Visit 3, and every 2 weeks thereafter. At these visits the following assessments are performed and measurements recorded: Physical examination; Vital signs; 12-lead ECG; Laboratory safety tests (hematology, serum chemistry, urinalysis); Special laboratory tests; PSA; PK sample (predose); Concomitant medications; AEs; Compliance diary collection; new compliance diary issued; Accountability procedures; and Trial Drug dispensed. Subjects are required to continue treatment once daily with dinner (between 17:00 and 21:00) until the visit 2 weeks later.

7.5 Trial Conclusion Visit

The Trial Conclusion Visit occurs on Day 85 (±5 days), 12 weeks after the first dose. The following details and assessments are performed and measurements recorded: Physical examination; Vital signs; 12-lead ECG; CT/MRI and bone scans—this is to be performed at the PSA nadir if it occurs before the Trial Conclusion Visit; Biopsy (a subset of subjects; covered by a separate ICF)—this is to be performed at the PSA nadir if it occurs before the Trial Conclusion Visit; Laboratory safety tests (hematology, serum chemistry, urinalysis); Special laboratory tests; PSA; PK sample (predose); Concomitant medications; AEs; Compliance diary collection; new compliance diary issued (if continuing into Extension); Accountability procedures; and Trial Drug dispensed (if continuing into the Extension).

7.6 Extension Phase

If a subject is eligible to continue into the Extension Phase, the subject returns to the clinical site every 4 weeks, where following assessments are performed, and measurements recorded: Physical examination; Vital signs; CT/MRI and bone scans (every 12 weeks); Laboratory safety tests (hematology, serum chemistry, urinalysis); Special laboratory tests; PSA; Concomitant medications; AEs; Compliance diary collection; new compliance diary issued; Accountability procedures; and Trial Drug dispensed.

7.7 Early Termination Visit

Subjects who discontinue early from the trial should, if possible, have an Early Termination Visit. This visit takes place as soon as possible after the subject stops taking Trial Drug. If a subject is prematurely withdrawn (prior to the 12-week visit) for any reason, the Investigator makes every effort to perform the safety evaluations described for the Trial Conclusion Visit (12-week visit).

8. Statistics

One aim of the Phase 1 stage of this trial is to find the dose(s) at which TOK-001 provides an acceptable safety profile. An acceptable safety profile is defined as a dose with a true DLT rate of ≤35%. The aims of the Phase 2 stage are to confirm an acceptable safety profile as well as assessing the biological signal for each of the dose(s) that are carried forward.

The following three dose groups are planned for Phase 1: (1) 650 mg Compound 1; (2) 1300 mg Compound 1; (3) 1950 mg Compound 1.

The possibility of visiting an intermediate dose aside, calculations of the probability of identifying each dose as the dose with an acceptable toxicity profile can be made according to the dose escalation and de-escalation rules described herein. Shown in Table 6 are three assumed-true DLT rates for each of the three doses, along with the probability that each is named the top dose (defined as the dose that emerges from the Phase 1 stage).

TABLE 6

Assumed Dose Limiting Toxicity Rates for three Doses of Compound 1

| True DLT rate at 650 mg | True DLT rate at 1300 mg | True DLT rate at 1950 mg | Prob that Top dose is 650 mg | Prob that Top dose is 1300 mg | Prob that Top dose is 1950 mg |
|---|---|---|---|---|---|
| .05 | .15 | .25 | .08 | .20 | .71 |
| .05 | .20 | .55 | .14 | .65 | .20 |
| .05 | .25 | .65 | .22 | .69 | .08 |

The probability that 650 mg Compound 1 is "too toxic" is 0.008 for each scenario above.

At the completion of the Phase 1 stage of the trial, up to two doses are chosen to move forward to the Phase 2 stage of the trial.

Since the safety of the doses that are moved forward to Phase 2 are assessed in a relatively small number of subjects (up to six, and no less than three) in Phase 1, stopping rules are in place so that enrollment to a particular dose can be stopped if there is reasonably convincing evidence to suggest that the true DLT rate at that dose is >35%. These limits are calculated after every fifth subject is evaluable for DLT. Operationally, any of the following would lead to such a limit, expresses in number of DLTs per numbers of subjects: 4 of 5 (or fewer), 6 of 10 (or fewer), 7 of 15 (or fewer), or 9 of 20 (or fewer).

If the true probability of DLT is 20% or 50%, the probability of stopping the trial due to excessive DLT is approximately 0.03 and 0.81, respectively (estimated from 5,000 simulations). If dosing is halted in an arm, Phase 2 dose revision occurs.

8.1 General Considerations and Baselines

Unless otherwise stated, all statistical tests are performed using 2-sided tests at the 5% significance level. Multiple comparison adjustments for multiple endpoints and visits are not performed at the final analysis because this is a Phase 1/2 trial; analyses are primarily descriptive in nature. Baseline is defined as the last observation before the first dose, unless otherwise specified. All inferential tests involve the direct comparison of the treatments using a 2-tailed test. Trial variables are summarized by descriptive statistics [N, mean, standard deviation (SD), median, minimum, and maximum for continuous variables and frequency and percentage for categorical variables].

8.2 Disposition of Subjects

The number and percentage of subjects entering and completing each phase of the trial are presented, stratified by treatment.

8.3 Analysis Populations

The primary efficacy analysis is based on the Intent-to-treat (ITT) Population, although a secondary analysis is also performed based upon the Per Protocol (PP) Population to assess the sensitivity of the analysis to the choice of analysis population. All safety analyses are based upon the Safety Population.

If a dose is stopped in Phase 2, subjects in the arm of the trial that is stopped are treated at the continuing dose and complete their 12-week follow-up schedule, but are not included in the efficacy analyses for the continuing dose.

8.3.1 Safety Population

All subjects who receive at least one dose of Trial Drug are included in the Safety Population.

8.3.2 Intent-to-Treat Population

All subjects who complete screening and are scheduled for treatment with Trial Drug are included in the ITT Population.

8.3.3 Per Protocol Population

The PP Population includes subjects who meet both of the following criteria: 1) receive at least one dose of Trial Drug; and 2) do not have any major protocol violations.

8.4 Protocol Deviations

Deviations from the protocol including violations of inclusion/exclusion criteria are assessed as "minor" or "major." Major deviations from the protocol lead to the exclusion of a subject from the PP Population.

8.5 Demographics and Baseline Characteristics

Continuous demographic parameters, such as age at the time of enrollment, are summarized for the Safety Population using descriptive statistics (N, mean, median, SD, minimum, and maximum value). Categorical demographic parameters, such as gender, are summarized as a frequency and proportion of the Safety Population.

8.6 Concomitant Medication

Concomitant medications are coded using the WHO Drug Dictionary version 12.0 or above. Data are summarized using descriptive statistics.

8.7 Treatment Exposure and Treatment Compliance

Treatment exposure and treatment compliance are summarized by frequency and percentage, stratified by treatment.

8.8 Safety Analyses

Safety analyses are carried out using the Safety Population. The safety endpoints of the trial include: incidence of AEs; changes in vital signs and 12-lead ECG; changes in physical examination; changes in laboratory assessments (serum chemistry, hematology, and urinalysis)

8.8.1 Adverse Events

All AEs recorded during the course of the clinical trial are coded according to the MedDRA system and assigned to a system organ class. TEAEs are defined as AEs that have first occurred or worsened in severity and/or frequency after initiation of therapy. Any event with an onset on the day of the first dose of Trial Drug, where the time of onset is missing, is assumed to be treatment-emergent.

The frequency of subjects experiencing any AEs by body system, relatedness, and severity are summarized in each treatment group using counts and percentages. For any given MedDRA preferred term, a subject contributes only a single count to the incidence, even if the subject had multiple occurrences over multiple courses of treatment. Relationship to Trial Drug is classified as related (definitely, probably, or possible) and unrelated (unlikely, unrelated). If multiple records exist for one subject, only maximum severity and strongest relationship to Trial Drug is counted for calculating percentage. Serious AEs are summarized overall and by body system and preferred term.

8.8.2 Laboratory Evaluations, Electrocardiogram, Vital Signs, and Physical Examination Changes from baseline in clinical laboratory, ECG, and vital sign parameters are calculated by treatment groups and visits. Descriptive statistics (N, mean, SD, median, minimum, and maximum) for changes from baseline are tabulated. Shift tables from baseline to post-baseline are generated by treatment group and visit for clinical laboratory and ECG parameters and physical examination. Frequencies and percentages are presented in the shift tables. Clinically significant abnormalities in laboratory assessments are noted in the data listings.

8.9 Efficacy Analyses

The ITT Population is used for all efficacy analyses.

8.9.1 Primary Efficacy Analysis

The primary efficacy endpoint is the percent of subjects with 50% or greater decrease in PSA from baseline to 12 weeks, or PSA nadir (whichever comes first). Frequency and percentage are calculated for each treatment group. The primary analysis is also repeated using the PP Population.

8.9.2 Secondary Efficacy Analyses

Descriptive statistics are tabulated and presented for each of the secondary efficacy parameters. All secondary efficacy analyses are performed using the ITT Population.

8.9.2.1 Progression by Response Evaluation Criteria in Solid Tumor (RECIST)

Response rates includes overall response rate (ORR). ORR is defined as:

$$ORR = (CR+PR)/Nr$$

where CR is the number of subjects with complete response, PR is the number of subjects with partial response, and Nr is the number of subjects that are included in the ITT Population.

Tumor response evaluation is performed using the following RECIST definitions.

| Response Evaluation Criteria in Solid Tumor (RECIST v 1.1) Definitions | | |
|---|---|---|
| Response Criteria | Target Lesion Evaluation Criteria | Non-target Lesion Evaluation Criteria |
| Complete Response (CR) | Disappearance of all target lesions. Any pathological lymph nodes (whether target or non-target) must have reduction in short axis to <10 mm. | Disappearance of all non-target lesions and normalization of tumor marker level. All lymph nodes must be non-pathological in size (<10 mm short axis). |

-continued

| Response Evaluation Criteria in Solid Tumor (RECIST v 1.1) Definitions | | |
|---|---|---|
| Response Criteria | Target Lesion Evaluation Criteria | Non-target Lesion Evaluation Criteria |
| Partial Response (PR) | At least a 30% decrease in the sum of the diameters of target lesions, taking as reference the baseline sum diameters. | N/A |
| Progressive Disease (PD) | At least a 20% increase in the sum of diameters of target lesions, taking as reference the smallest sum on study (this includes baseline sum if that is the smallest on study). In addition to the relative increase of 20%, the sum must also demonstrate an absolute increase of at least 5 mm. (Note: the appearance of one or more new lesions is also considered progression). | Unequivocal progression of existing non-target lesions. (Note: the appearance of one or more new lesions is also considered progression). |
| Stable Disease (SD) - Target Lesions Non-CR/Non-PD - Non-target Lesions | Neither sufficient shrinkage to qualify for PR nor sufficient increase to qualify for PD, taking as reference the smallest sum diameters while on study. | Persistence of one or more non-target lesions and/or maintenance of tumor marker level above normal limits. |

The subject response is the best response recorded from the start of treatment until disease progression/recurrence as outlined in Table 8.

TABLE 8

Subject Response

| Target Lesions | Non-target Lesions | New Lesions | Subject Response |
|---|---|---|---|
| CR | CR | No | CR |
| CR | Non-CR/non-PD | No | PR |
| CR | Not evaluated | No | PR |
| PR | Non-PD or not all evaluated | No | PR |
| SD | Non-PD or not all evaluated | No | SD |
| Not all evaluated | Non-PD | No | NE (not evaluated) |
| PD | Any | Yes or No | PD |
| Any | PD | Yes or No | PD |
| Any | Any | Yes | PD |

8.9.2.2 Change from Baseline in CT/MRI and bone Scans, Additional Special Laboratories, and Parameters in the Biopsy Subset Changes from baseline in CT/MRI and bone scans, additional special laboratories, and intratumoral parameters (intratumoral AR protein, testosterone, and DHT) in the biopsy subset are calculated by treatment group and visit. Descriptive statistics (N, mean, SD, median, minimum, and maximum) for changes from baseline are tabulated by treatment group.

8.9.2.3 Time to Progression, Progression-Free Survival and Overall Survival

TTP, PFS, and OS are Extension Phase specific endpoints.

Time-to-progression (TTP) is defined as the time from first dose of Trial Drug to first documented PI evaluation of the disease becoming worse, based on clinical course, radiological evidence, and biochemical markers (PSA) results.

Progression-free survival (PFS) is the length of time during and after treatment in the trial in which a subject is living with the disease (CRPC) that does not worsen.

Overall Survival (OS) is defined as the time from first dose of Trial Drug to first documentation of death due to any cause. For the purpose of this trial OS is reported as percentage of survived subjects 5 years after receiving the first dose of Trial Drug.

The analysis of TTP, PFS, and OS uses the log-rank tests for the comparison between Compound 1 dose groups using the ITT Population. Kaplan-Meier estimates are plotted by treatment group. Median time to events with 95% confidence interval, if estimable, are also be tabulated by treatment group.

Subjects who have not experienced events at the cut-off date are censored from the analysis using the cut-off date as the date of censoring. Subjects who withdraw early are censored from the analysis using the last contact date as the date of censoring.

8.9.2.4 Exploratory Endpoints

The following analyses are possible exploratory endpoints for the Phase 2 stage of the trial: 1) PSA changes over 12 weeks (starting from the first dose and covering the 12 weeks of treatment); and/or PSA nadir and time to PSA nadir (nadir is the lowest PSA value observed during the Compound 1 dosing period).

Descriptive statistics (N, mean, SD, median, minimum, and maximum) are tabulated by treatment group.

8.10 Concentration of Compound 1

Plasma concentration of Compound 1 is determined at 0 hours ($C_{0hrs}$) and 4 hours ($C_{4hrs}$) on Day 1, and for available timepoints at subsequent visits.

8.11 Determination of Phase 2 Sample Size

If two doses have been chosen from Phase 1, then 40 subjects are randomized in a 1:1 ratio between the two doses. If only one dose is carried forward, 20 subjects are assigned to this dose and no randomization occurs. This section describes the justification of the choice of a sample size of 20 subjects per arm.

The initial dose, 650 mg Compound 1, is thought to be well-tolerated and the intent of the study is that 12 to 15 subjects are enrolled in Phase 1 [including some treated at the Phase 2 dose(s)]. While the subjects treated on Phase 1 at the doses used in Phase 2 are not randomized, they undergo consistent treatment and follow-up schedule. Therefore, they are included when examining the potential of biological effect in the Phase 2 stage of the trial and it is expected that at least 23 subjects (up to 26) at a particular dose can be available for analysis of biological signal in Phase 2. If two doses emerge from Phase 1, one of these doses is identified as the preferred dose. If this dose is deemed to have a significantly strong biological signal, this dose is taken forward to a future trial. The choice of 20 subjects per arm is based on the expectation of having at least 23 subjects (and as many as 26) treated at a particular dose in Phase 2. A set of twenty-three (23) subjects provides a 92% power to observe a statistically significantly improved "response rate" (reduction in PSA) relative to the fixed rate of 45% if the assumed-true rate is 75%.

The endpoint used for examination of biological effect is the percentage of subjects with a 50% or greater decrease in PSA from baseline to 12 weeks, or PSA nadir (whichever comes first). If two doses emerge from Phase 1, the dose that has the largest percentage of such subjects is identified as the preferred dose from Phase 2. The future of this preferred dose (or the single dose if only one is carried forward to Phase 2 for subsequent trials are governed by the following guidelines: 1) if the observed PSA response for the preferred dose is 30-45%, Compound 1 likely undergoes additional dose-finding work; 2) if the observed PSA response is 45-75%, Compound 1 is considered to have a potential biological effect and a larger Phase 2 or 2/3 trial is designed to confirm and more precisely estimate the PSA response, in addition to measures of efficacy such as overall survival and time to progression; and 3) if the observed PSA response exceeds 75%, strong consideration is given to taking this dose directly into a Phase 3 trial.

The probability of observing a PSA response of 45% or more among 23 or 26 subjects at a particular dose is summarized in Table 7 for various assumed-true response rates.

TABLE 7

Probability of Observing a Prostate Specific Antigen Response of 45% or More

| True Response Rate | Probability Observed Response ≥ 45% among 23 subjects | Probability Observed Response ≥ 45% among 26 subjects |
|---|---|---|
| .25 | .01 | .04 |
| .40 | .29 | .48 |
| .45 | .47 | .68 |
| .50 | .66 | .84 |
| .55 | .82 | .93 |
| .60 | .92 | .98 |

Moreover, if the true PSA response rate is 75%, then a set of 23 subjects provides 92% power to observe a statistically significantly improved response rate compared to the fixed rate of 45% (at the one-sided level of significance of 0.05). The same parameters with n=26 yield 94% power. A set of twenty-three subjects also provides 91% power if the benchmark response rate is 30% and the assumed-true response rate is 60%. These assumptions with n=26 yield 94%.

Statistically significant improvement in response rate relative to a specific benchmark is not required to move forward to a subsequent trial, but these power calculations provide some justification for the required observed rates that help determine the direction of the next trial, in addition to a rationale for the choice of 20 subjects per arm for the sample size in Phase 2. If two doses are brought forward to Phase 2, and the true response rates for the arms are 45% and 60%, then the arm with the true higher response rate are chosen, with a probability of approximately 0.88 with 23 subjects per arm (probability estimated from simulations); sample size of 23 comes from 20 randomized to each arm in Phase 2 plus at least three treated at each dose in Phase 1.

Example 7

Clinical Study Results for Treatment of Prostate Cancer with Compound (1)

A clinical study was performed according to the protocol of Example 6. Compound (1) was administered to four cohorts, each in a different amount. Each individual subject received the same amount of Compound (1) for the duration of the subject's involvement.

| Cohort | Dose Level (mg/day) | Number of Patients Treated | Percentage of Patients With a PSA Response (N) |
|---|---|---|---|
| 1 | 650 | 6 | 67% (4) |
| 2 | 975 | 6 | 67% (4) |
| 3 | 1300 | 6 | 83% (5) |
| 4 | 1950 | 7 | 71% (5) |

The results show that the majority of subjects in each group responded favorably to the therapy. Cohorts 3 and 4, receiving larger amounts of Compound (1), produced higher response rates.

Figure 13:
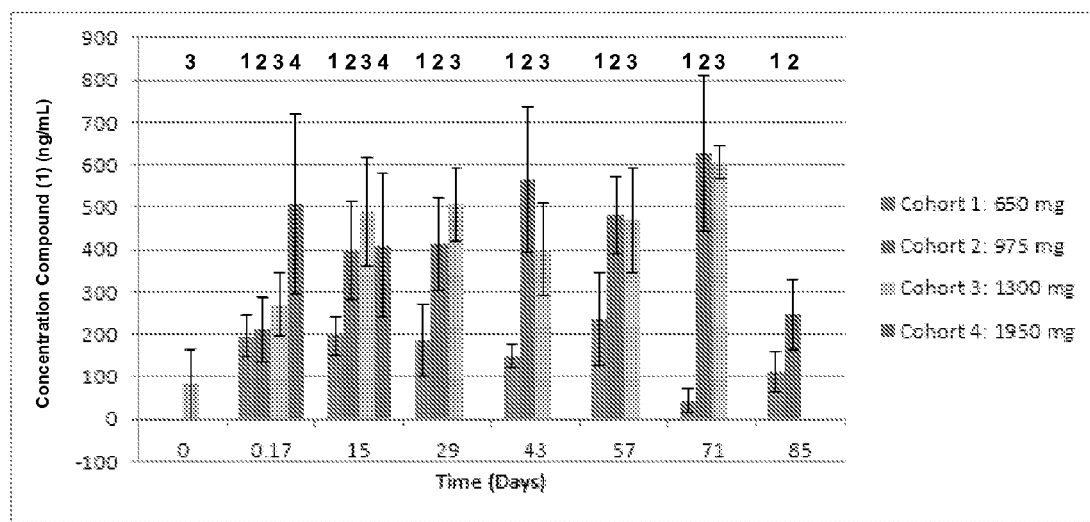
FIG. 13 illustrates the serum concentrations of Compound (1) in the subjects of a clinical trial over time. The cohort groups are listed across the top of the figure.

The serum concentration of Compound (1) was tracked in each subject for the duration of the subject's participation. The concentrations are illustrated in FIG. 13. Not all subjects followed the same schedule, nor did all cohorts follow the same schedule. Of note in FIG. 13 is that the serum concentration of Compound (1) found in subjects of cohorts 2 and 3 were frequently more than double the concentration found in cohort 1, although the subjects of cohorts 2 and 3 received less than double, and double the amounts that the subjects of cohort 1 received, respectively. These data indicate that higher dosages have a greater efficacy per unit effect, and that more productive and economical therapy is achievable with the higher dosages of Compound (1).

What is claimed is:

1. A pharmaceutical composition for use in the treatment of castration-resistant prostate cancer, wherein said pharmaceutical composition comprises 650-3500 mg of Compound (1):

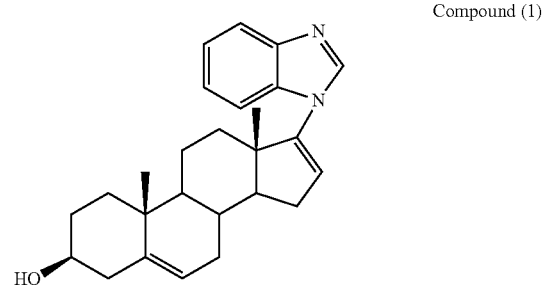 [SMILES: C[C@]12CC[C@H](O)CC1=CCC1C2CC[C@]2(C)C(n3cnc4ccccc43)=CCC12]

Compound (1)

as a micronized crystalline form,
wherein the crystalline form of Compound (1) is characterized by a powder X-ray diffraction pattern having characteristic peaks expressed in angle 2-theta at about 13.0°, 14.6°, 16.3°, 17.6° and 19.0±0.2°, and optionally characteristic peaks at about 11.8°, 20.2°, 22.9° and 25.4±0.2°.

2. The pharmaceutical composition of claim 1, wherein Compound (1) is present in an amount effective to inhibit androgen biosynthesis, inhibit androgen receptor signaling or decrease androgen receptor sensitivity in a subject.

3. The pharmaceutical composition of claim 2, wherein the compound is present in an amount effective to inhibit androgen receptor signaling or decreases androgen receptor sensitivity.

4. The pharmaceutical composition of claim 2, wherein the androgen biosynthesis inhibition comprises inhibiting the activity of cytochrome $C_{17\alpha}$-hydroxylase/C17,20-lyase (CYP17).

5. The pharmaceutical composition of claim 2, wherein the androgen receptor signaling inhibition comprises competitive inhibition of testosterone binding.

6. The pharmaceutical composition of claim 2, wherein the decrease in androgen receptor sensitivity comprises a reduction of the content of androgen receptor protein within the cell, and a diminished ability of the cell to be sustained by low levels of androgenic growth signals.

7. The pharmaceutical composition of claim 1, wherein the composition is formulated for administration to a subject parenterally, intravenously, intramuscularly, intradermally, subcutaneously, intraperitoneally, orally, buccally, sublingually, mucosally, rectally, transcutaneously, transdermally, ocularly, or by inhalation.

8. The pharmaceutical composition of claim 1, wherein the composition is formulated for administration to a subject as a tablet, a capsule, a cream, a lotion, an oil, an ointment, a gel, a paste, a powder, a suspension, an emulsion, or a solution.

9. The pharmaceutical composition of claim 1, wherein the composition is formulated for administration to a subject as a capsule.

10. The pharmaceutical composition of claim 1, wherein the composition is formulated for administration to a subject as a tablet.

11. The pharmaceutical composition of claim 1, wherein the composition is formulated for administration to a subject and comprises between about 25 mg/kg to about 50 mg/kg of Compound (1).

12. The pharmaceutical composition of claim 1, wherein the composition comprises about 1950 mgs of Compound (1).

13. The pharmaceutical composition of claim 1, wherein the composition comprises about 1300 mgs of Compound (1).

14. The pharmaceutical composition of claim 1, wherein the composition comprises about 650 mgs or about 975 mgs of Compound (1).

15. The pharmaceutical composition of claim 1, wherein the composition is formulated for administration to a subject, one, two, three, four, five, six, seven, eight, nine, or ten times per day.

16. The pharmaceutical composition claim 1, wherein the composition further comprises one or more pharmaceutically acceptable excipients.

17. The pharmaceutical composition of claim 16, wherein the pharmaceutically acceptable excipient comprises a filler, a disintegrant, a lubricant, a surfactant, a glidant, a binder, a sugar, a starch, a varnish, or a wax.

18. A method of treating castration-resistant prostate cancer in a subject in need of such treatment, the method comprising administering to the subject a pharmaceutical composition comprising a therapeutically-effective amount of Compound (1):

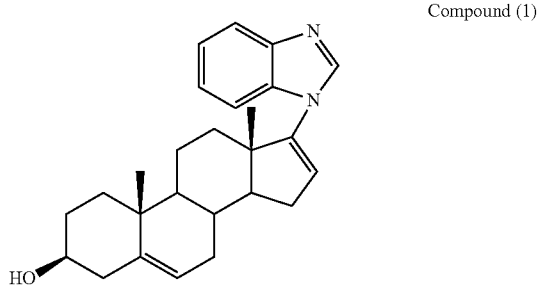 [SMILES: C[C@]12CC[C@H](O)CC1=CCC1C2CC[C@]2(C)C(n3cnc4ccccc43)=CCC12]

Compound (1)

as a micronized crystalline form,
wherein the crystalline form of Compound (1) is characterized by a powder X-ray diffraction pattern having characteristic peaks expressed in angle 2-theta at about 13.0°, 14.6°, 16.3°, 17.6° and 19.0±0.2°, and optionally characteristic peaks at about 11.8°, 20.2°, 22.9° and 25.4±0.2°.

19. The method of claim 18, wherein the subject is a human.

20. The method of claim 18, wherein the composition is administered to the subject in the form of a tablet or capsule.

21. The method of claim 18, wherein the composition comprises between about 25 mg/kg to about 50 mg/kg of Compound (1).

22. The method of claim 18, wherein the composition comprises about 650 mg to about 3500 mg of Compound (1).

23. The method of claim 18, wherein the composition comprises about 1950 mgs of Compound (1).

24. The method of claim 18, wherein the composition comprises about 1300 mgs of Compound (1).

25. The method of claim 18, wherein the composition comprises about 650 mgs or about 975 mgs of Compound (1).

26. The method of claim 18, wherein the composition comprises between 900 mgs and 1950 mgs of Compound (1).

* * * * *